United States Patent
Moullier et al.

(10) Patent No.: US 11,382,988 B2
(45) Date of Patent: Jul. 12, 2022

(54) MODIFIED ADENO-ASSOCIATED VIRUS VECTORS AND DELIVERY THEREOF INTO THE CENTRAL NERVOUS SYSTEM

(71) Applicant: Coave Therapeutics, Paris (FR)

(72) Inventors: Philippe Moullier, San Sebastian (ES); Willem Broekaert, Dilbeek (BE)

(73) Assignee: Coave Therapeutics, Paris (FR)

( * ) Notice: Subject to any disclaimer, the term of this patent is extended or adjusted under 35 U.S.C. 154(b) by 0 days.

(21) Appl. No.: 17/163,244

(22) Filed: Jan. 29, 2021

(65) Prior Publication Data
US 2021/0162072 A1    Jun. 3, 2021

Related U.S. Application Data

(63) Continuation of application No. PCT/EP2020/081396, filed on Nov. 6, 2020.

(30) Foreign Application Priority Data

Nov. 8, 2019 (EP) .................................... 19306450

(51) Int. Cl.
*A61K 48/00* (2006.01)
*C12N 15/86* (2006.01)

(52) U.S. Cl.
CPC ...... *A61K 48/0033* (2013.01); *A61K 48/0075* (2013.01); *C12N 15/86* (2013.01); *C12N 2750/14143* (2013.01); *C12N 2810/10* (2013.01)

(58) Field of Classification Search
CPC .................. C12N 15/86; C12N 15/861; C12N 2750/14143; C12N 2810/10
See application file for complete search history.

(56) References Cited

U.S. PATENT DOCUMENTS

| | | |
|---|---|---|
| 6,335,324 B1 | 1/2002 | Bisacchi et al. |
| 10,087,217 B2 | 10/2018 | Zhou et al. |
| 2004/0147502 A1 | 7/2004 | Bisacchi et al. |
| 2004/0180855 A1 | 9/2004 | Schumacher et al. |
| 2010/0098666 A1 | 4/2010 | Wright |
| 2014/0336245 A1 | 11/2014 | Mingozzi et al. |
| 2015/0017703 A1 | 1/2015 | Agnew |
| 2016/0297855 A1 | 10/2016 | Zhou et al. |
| 2017/0128594 A1 | 5/2017 | Wright |
| 2018/0201907 A1 | 7/2018 | Agnew |
| 2018/0371496 A1 | 12/2018 | Li et al. |
| 2019/0203227 A1 | 7/2019 | Ho et al. |
| 2019/0388557 A1 | 12/2019 | Mevel et al. |
| 2020/0157570 A1 | 5/2020 | Loiler |
| 2020/0172913 A1 | 6/2020 | Desai et al. |
| 2020/0224219 A1 | 7/2020 | Buning et al. |
| 2020/0325456 A1 | 10/2020 | Li et al. |
| 2020/0340012 A1 | 10/2020 | Mali et al. |
| 2020/0405639 A1 | 12/2020 | Zhang et al. |

FOREIGN PATENT DOCUMENTS

| | | |
|---|---|---|
| WO | WO-1999/67215 A1 | 12/1999 |
| WO | WO-2005/106046 A1 | 11/2005 |
| WO | WO-2008/128251 A1 | 10/2008 |
| WO | WO-2011/082285 A1 | 7/2011 |
| WO | WO-2013/078400 A1 | 5/2013 |
| WO | WO-2013/112778 A1 | 8/2013 |
| WO | WO-2015/048534 A1 | 4/2015 |
| WO | WO-2015/062516 A1 | 5/2015 |
| WO | WO-2017/053629 A2 | 3/2017 |
| WO | WO-2017/212019 A1 | 12/2017 |
| WO | WO-201 8/035503 A1 | 2/2018 |
| WO | WO-2018/191750 A2 | 10/2018 |
| WO | WO-201 8/226602 A1 | 12/2018 |
| WO | WO-201 9/03291 7 A1 | 2/2019 |
| WO | WO-2019/063747 A1 | 4/2019 |
| WO | WO-2019/126356 A1 | 6/2019 |
| WO | WO-2021/00521 0 A1 | 1/2021 |

OTHER PUBLICATIONS

Liguore et al.; AAV-PHP.B Administration Results in a Differential Pattern of CNS Biodistribution in Non-human Primates Compared with Mice; Molecular Therapy, vol. 27, No. 11, pp. 2018-2037, published online Aug. 5, 2019 (Year: 2019).*
Niethammer et al.; Long-term follow-up of a randomized AAV2-GAD gene therapy trial for Parkinson's disease; JCI Insight. 2017;2(7):e90133, pp. 1-10 (Year: 2017).*
Zuleta et al.; AAV-mediated delivery of the transcription factor XBP1s into the striatum reduces mutant Huntingtin aggregation in a mouse model of Huntington's disease; Biochemical and Biophysical Research Communications 420 (2012) 558-563 (Year: 2012).*
Hocquemiller et al.; Adeno-Associated Virus-Based Gene Therapy for CNS Diseases; Human Gene Therapy, vol. 27, No. 7, pp. 478-496, published online Jun. 7, 2016 (Year: 2016).*
Albright, B. H. et al., Mapping the structural determinants required for AAVrh.10 Transport across the BBB, Mol. Ther., 26(2):510-523 (2018).
Aschauer, D. F. et al., Analysis of Transduction Efficiency, Tropism and Axonal Transport of AAV Serotypes 1, 2, 5, 6, 8 and 9 in the Mouse Brain, PLoS One. 8(9):e76310 (2013).
Asokan, A. et al., Reengineering a receptor footprint of adeno-associated virus enables selective and systemic gene transfer to muscle, Nat. BiotechnoL, 28(1):79-82 (2010).
Bartel, M. A. et al., Directed evolution of novel adeno-associated viruses for therapeutic gene delivery, Gene Ther., 19(6):694-700 (2012).
Bevan, A. K. et al., Systemic Gene Delivery in Large Species for Targeting Spinal Cord, Brain, and Peripheral Tissues for Pediatric Disorders, Mol Ther., 19(11):1971-80 (2011).

(Continued)

*Primary Examiner* — Antonio Galisteo Gonzalez
(74) *Attorney, Agent, or Firm* — Choate, Hall & Stewart LLP; Nicholas J. Pace; Katherine T. Grasso

(57) ABSTRACT

The present invention relates to modified adeno-associated virus (AAV) vectors for use in transducing a cell in the central nervous system (CNS) of a subject, and for use in the prevention or treatment of a CNS disease. In particular, the modified AAV vectors according to the present invention comprise at least one surface-bound saccharide, and are to be administered directly to the CNS but not intracerebroventricularly.

26 Claims, 21 Drawing Sheets

(56) References Cited

OTHER PUBLICATIONS

Boutin, S. et al., Prevalence of Serum IgG and Neutralizing Factors Against Adeno-Associated Virus AAV Types 1, 2, 5, 6, 8, and 9 in the healthy population, Implications for Gene Therapy Using AAV Vectors, Hum. Gene Ther., 21(6):704-12 (2010).
Burger, C. et al., Recombinant AAV Viral Vectors Pseudotyped with Viral Capsids from Serotypes 1, 2, and 5 Display Differential Efficiency and Cell Tropism after Delivery to Different Regions of the Central Nervous System, Mol. Ther., 10(2):302-317 (2004).
Cearley, C. N. and Wolfe, J. H., Transduction Characteristics of Adeno-associated Virus Vectors Expressing Cap Serotypes 7, 8, 9, and Rh10 in the Mouse Brain, Mol. Ther., 13(3):528-37 (2006).
Cearley, C. N. et al., Expanded Repertoire of AAV Vector Serotypes Mediate Unique Patterns of Transduction in Mouse Brain, Mol. Ther., 16(10):1710-8 (2008).
Foust, K. D. et al., Intravascular AAV9 preferentially targets neonatal neurons and adult astrocytes, Nat. Biotechnol., 27(1):59-65 (2009).
Fu, H. et al., Differential Prevalence of Antibodies Against Adeno-Associated Virus in Healthy Children and Patients with Mucopolysaccharidosis III, Perspective for AAV-Mediated Gene Therapy, Hum. Gene Ther. Clin. Dev., 28:187-96 (2017).
Girod, A. et al., Genetic capsid modifications allow efficient re-targeting of adeno-associated virus type 2, Nat. Med., 5(9):1052-1056 (1999).
Gray, S. J. et al., Directed Evolution of a Novel Adeno-associated Virus AAV Vector That Crosses the Seizure-compromised Blood-Brain Barrier BBB, Mol. Ther., 18(3):570-8 (2010).
Gray, S. J. et al., Global CNS Gene Delivery and Evasion of Anti-AAV Neutralizing Antibodies by Intrathecal AAV Administration in Non-Human Primates, Gene Ther. 20(4):450-9 (2013).
Gray, S. J. et al., Preclinical Differences of Intravascular AAV9 Delivery to Neurons and Glia, A comparative Study of Adult Mice and Nonhuman Primates, Mol. Ther., 19(6):1058-69 (2011).
Hudry, E. et al., Exosome-associated AAV vector as a robust and convenient neuroscience tool, Gene Ther., 23:380-92 (2016).
Katrekar, D. et al., Oligonucleotide conjugated multifunctional adeno-associated viruses, Sci. Rep., 8(3589):1-8 (2018).
Koerber, J. T. et al., Construction of diverse adeno-associated viral libraries for directed evolution of enhanced gene delivery vehicles, Nat. Protoc., 1(2):701-6 (2006).
Kwon, I. and Schaffer, D., Designer Gene Delivery Vectors, Molecular Engineering and Evolution of Adeno-Associated Viral Vectors for Enhanced Gene Transfer, Pharm. Res., 25(3):489-99 (2008).
Kye-IL, J. et al., Enhanced Real-Time Monitoring of Adeno-Associated Virus Trafficking by Virus-Quantum Dot Conjugates, ACS NANO, 5(5):3523-3535 (2011).
Lee, G. K. et al., PEG Conjugation Moderately Protects Adeno-Associated Viral Vectors Against Antibody Neutralization, Biotechnol. Bioeng., 92:24-34 (2005).
Lykken, E. A. et al., Recent progress and considerations for AAV gene therapies targeting the central nervous system, J. Neurodev. Disord., 10(1):16 (2018).
Maguire, C. A. et al., Microvesicle-associated AAV Vector as a Novel Gene Delivery System, Mol. Ther., 20:960-71 (2012).
Maheshri, N. et al., Directed evolution of adeno-associated virus yields enhanced gene delivery vectors, Nat. Biotechnol., 24(2):198-204 (2006).
Marsic, D. and Zolotukhin, S Altering Tropism of rAAV by Directed Evolution, Methods Mole. Biol., 1382:151-173 (2016).
McPhee, S. W. J. et al., Immune responses to AAV in a phase I study for Canavan disease, J. Gene Med., 8:577-588 (2006).
Mevel, M. et al., Chemical modification of the adeno-associated virus capsid to improve gene delivery, Chem. Sci., 10 pages (2019).

Miyake, N. et al., Global gene transfer into the CNS across the BBB after neonatal systemic delivery of single-stranded AAV vectors, Brain Res., 1389:19-26 (2011).
Perabo, L. et al., Artificial Evolution with Adeno-Associated Viral Libraries, Comb. Chem. High Throu. Screen., 11:118-126 (2008).
Rabinowitz, J. E. et al., Insertional Mutagenesis of AAV2 Capsid and the Production of Recombinant Virus, Virology, 265(2):274-85 (1999).
Samaranch, L. et al., AAV9-mediated Expression of a Non-self Protein in Nonhuman Primate CNS Triggers Widespread Neuroinflammation Driven by Antigen-presenting Cell Transduction, Mol. Ther., 22(2):329-37 (2014).
Samaranch, L. et al., Adeno-Associated Virus Serotype 9 Transduction in the CNS of Nonhuman Primates, Hum. Gene Ther., 23(4):382-9 (2012).
Schaffer, D. V. and Maheshri, N. Directed Evolution of AAV Mutants for Enhanced Gene Delivery, 26th Annual International Conference of the IEEE EMBS, San Francisco, CA, 3520-3523 (Sep. 2004).
Shen, S. et al., Engraftment of a Galactose Receptor Footprint onto Adeno-associated Viral Capsids Improves Transduction Efficiency, J. Biol. Chem., 288(40):28814-23 (2013).
Sletten, E. M. and Bertozzi, C. R Bioorthogonal chemistry: fishing for selectivity in a sea of functionality, Angew. Chem. Int. Ed. Engl., 48(38):6974-98 (2009).
Taymans, J-M et al., Comparative analysis of adeno-associated viral vector serotypes 1, 2, 5, 7, and 8 in mouse brain, Hum. Gene Ther., 18(3):195-206 (2007).
Tse, L. V. et al., Structure-guided evolution of antigenically distinct AAV variants for immune evasion, Proc. Natl. Acad. Sci. USA, 114(24):E4812-E4821 (2017).
Vite, C. H. et al., Effective Gene Therapy for an Inherited CNS Disease in a Large Animal Model, Ann. Neurol., 57:355-364 (2005).
Watakabe, A. et al., Comparative analyses of AAV vector serotypes 1, 2, 5, 8 and 9 in marmoset, mouse and macaque cerebral cortex, Neurosci. Res., 93:144-57 (2015).
Wobus, C. E. et al., Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection, Jrnl. Viro., 74(19):9281-9293 (2000).
Ellinwood, M. N. et al., Safe, Efficient, and Reproducible Gene Therapy of the Brain in the Dog Models of Sanfilippo and Hurler Syndromes, Mol. Ther., 19(2):251-259 (2011).
Hinderer, C. et al.. Evaluation of Intrathecal Routes of Administration for Adeno-Associated Viral Vectors in Large Animals, Hum. Gene Thera., 29(1):15-24 (2018).
Hordeaux, J. et al., The Neurotropic Properties of AAV-PHP.B Are Limited to C57BL/6J Mice, Mol. Ther., 26(3):664-668 (2018).
International Search Report for PCT/EP2020/081396, 5 pages (dated Feb. 1, 2021).
McCurdy, V. J. et al., Sustained normalization of neurological disease after intracranial gene therapy in a feline model, Sci. Transl. Med., 6(231):1-24 (2014).
Mével, M. et al., Chemical modification of the adeno-associated virus capsid to improve gene delivery, Che,. Sci., 11:1122-1131 (2020).
Vite, C. H. et al., Effective Gene Therapy for an Inherited CNS Disease in a Large Animal Model, Annals Neuro., 57(3):355-364 (2005).
Asano, S. et al., Preparation and Activities of Macromolecule Conjugates of the CCR5 Antagonist Maraviroc, ACS Med. Chem. Lett., 5:133-137 (2014).
International Search Report for PCT/EP2021/080832, 9 pages (dated Feb. 21, 2022).
Raja, K. S. et al., Icosahedral Virus Particles as Polyvalent Carbohydrate Display Platforms, ChemBioChem, 4:1348-1351 (2003).
Sato, S. et al., Chemically Programmed Antibodies As HIV-1 Attachment Inhibitors, ACS Med. Chem. Lett., 4:460-465 (2013).

* cited by examiner

G1: Vehicle

G2: mann-AAV2-GFP

G3: AAV2-GFP

G1: Vehicle
G2: Mannose-AAV2-GFP
FIG.9A
FIG.9B
G3: AAV2-GFP
FIG.9C

G1: Vehicle

G2: Mannose-AAV2-GFP

G3: AAV2-GFP

G1 : Vehicle

G2: AAV2-GFP

G3: Mannose-AAV2-GFP    G4: Galactose-AAV2-GFP
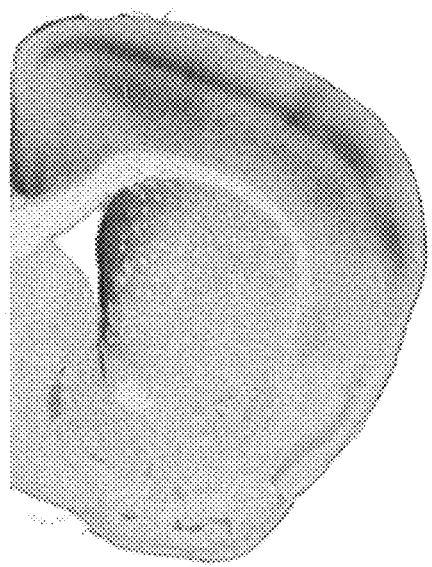
FIG.11C    FIG.11D
G5: N-acetyl-glucosamine-AAV2-GFP
FIG.11E G3: Mannose-AAV2-GFP G4: Galactose-AAV2-GFP G5: N-acetyl-
glucosamine-AAV2-GFP G1 : Vehicle

G3: Mannose-AAV2-GFP

G4: Galactose-AAV2-GFP

G5: N-acetyl-glucosamine-AAV2-GFP

2 : AAV2-GFP

3 : AAV5-GFP

4 : Mannose-AAV2-GFP

MODIFIED ADENO-ASSOCIATED VIRUS VECTORS AND DELIVERY THEREOF INTO THE CENTRAL NERVOUS SYSTEM

CROSS REFERENCE TO RELATED APPLICATIONS

This applications is a Continuation of International Application No. PCT/EP2020/081396, filed Nov. 6, 2020, which claims priority to European Patent Application Serial No. 19306450.8, filed Nov. 8, 2019; the entire contents of which are herein incorporated by reference.

FIELD OF INVENTION

The present invention relates to modified adeno-associated virus (AAV) vectors for use in transducing a cell in the central nervous system (CNS) of a subject, and for use in the prevention or treatment of a CNS disease. In particular, the modified AAV vectors according to the present invention comprise at least one surface-bound saccharide, and are to be administered directly to the CNS, but not intracerebroventricularly.

BACKGROUND OF INVENTION

Diseases affecting the central nervous system (CNS) have been particularly difficult to treat with traditional drugs, among other things because of low blood-brain barrier penetration abilities and high off-target effects.

The advent of gene therapy offers the potential for transformative therapies to slow down or stop disease progression in late-stage patients, and to prevent the appearance of clinical symptoms in early-stage, asymptomatic individuals (Lykken et al., 2018. *J Neurodev Disord.* 10(1):16).

Multiple vectors are currently available, including integrating lentivirus vectors and non-integrating adeno-associated virus (AAV) vectors. Over the past decade, AAVs have proven to be reliable, efficient, versatile, and safe tools to deliver, in a single administration, a transgene of interest to a variety of tissues, notably including the CNS.

CNS-directed gene therapy studies have been focused mainly on four AAV serotypes: AAV2, AAV5, AAV8 and AAV9 (Burger et al., 2004. *Mol Ther.* 10(2):302-17; Cearley & Wolfe, 2006. *Mol Ther.* 13(3):528-37; Taymans et al., 2007. *Hum Gene Ther.* 18(3):195-206; Cearley et al., 2008. *Mol Ther.* 16(10):1710-8; Foust et al., 2009. *Nat Biotechnol.* 27(1):59-65; Aschauer et al., 2013. *PLoS One.* 8(9):e76310; Watakabe et al., 2015. *Neurosci Res.* 93:144-57).

Typically, CNS-directed AAV delivery has been performed locally to the brain and/or spinal cord, since AAVs of all serotypes but AAV9 generally fail to cross the blood-brain barrier, and therefore cannot be administered non-invasively via the vascular system to reach target cells in the CNS (Miyake et al., 2011. *Brain Res.* 1389:19-26). AAV9 in particular, has been shown to be the most efficient at transducing neurons and astrocytes of the CNS after intracerebral or intrathecal administration (Cearley & Wolfe, 2006. *Mol Ther.* 13(3):528-37; Gray et al., 2013. *Gene Ther.* 20(4):450-9). Still, the need for an AAV vector with wider transduction properties remains, in particular to address diseases that involve cells scattered throughout the CNS.

Injections to multiple sites of the CNS have been performed to compensate for limited AAV spreading from the delivery site, and to provide more extensive tissue coverage. However, even where such strategies may have been applied successfully to preclinical animal models (Vite et al., 2005. *Ann Neurol.* 57(3):355-64), translation to humans has been hampered by the scaling-up of such invasive approaches. In this context, an AAV vector capable of achieving widespread transduction from a single, or very few, local administration point(s) in the CNS would be advantageous.

Intravascular delivery using AAV9 vectors has been proposed as an alternative approach for achieving non-invasive, widespread transduction in the CNS (Bevan et al., 2011. *Mol Ther.* 19(11):1971-80). However, while this route of administration is extremely effective in mice, transduction in the CNS of larger animals has been much more restricted (Gray et al., 2011. *Mol Ther.* 19(6):1058-69; Samaranch et al., 2012. *Hum Gene Ther.* 23(4):382-9). This approach is further limited by the extremely large doses required to achieve transduction in the brain and the resulting high off-target transduction of peripheral organs (Bevan et al., 2011. *Mol Ther.* 19(11):1971-80; Gray et al., 2011. *Mol Ther.* 19(6):1058-69). Lastly, pre-existing immunity against AAV9 due to earlier exposure to the wild-type virus precludes the use of the intravascular route in as many as 43% human adults, because neutralizing antibodies have been shown to clear viral particles out of the system before they can reach the CNS (Boutin et al., 2010. *Hum Gene Ther.* 21(6):704-12; Fu et al., 2017. *Hum Gene Ther Clin Dev.* 28:187-96).

Overall, immune response to AAVs remains an unresolved challenge to therapeutic efficacy, independent of the administration modality. Both adaptative and innate cellular immune responses can hinder AAV transduction efficiency, even in an immune-privileged organ such as the CNS (MacPhee et al. 2006. *J Gene Med.* 8:577-88; Samaranch et al. 2014. *Mol Ther.* 22(2):329-37). Therefore, an AAV vector capable of avoiding immune detection, while ensuring both cell-specific and widespread transduction in the CNS, would be highly desirable.

Efforts over the years have focused on improving AAVs, through modifications of either their capsid or their expression cassette, to evade the immune system and enhance AAV cell transduction and transgene expression properties.

Current strategies for the development of capsid-modified AAV vectors are based on three different approaches: (i) a rational design approach, based inter alia on the knowledge of AAV capsid binding to cellular receptors to redirect AAV vector tropism (Rabinowitz et al., 1999. *Virology.* 265(2): 274-85; Girod et al., 1999. *Nat Med.* 5(12):1438; Asokan et al., 2010. *Nat Biotechnol.* 28(1):79-82; Shen et al., 2013. *J Biol Chem.* 288(40):28814-23; Albright et al., 2017. *Mol Ther.* 26(2):510-523; Tse et al., 2017. *Proc Natl Acad Sci USA.* 114(24):E4812-E4821); (ii) a directed evolution approach, based on random mutagenesis, capsid shuffling and random peptide insertions (Schaffer & Maheshri, 2004. *Conf Proc IEEE Eng Med Biol Soc.* 5:3520-3; Koerber et al., 2006. *Nat Protoc.* 1(2):701-6; Maheshri et al., 2006. *Nat Biotechnol.* 24(2):198-204; Perabo et al., 2008. *Comb Chem High Throughput Screen.* 11(2):118-26; Kwon & Schaffer, 2008. *Pharm Res.* 25(3):489-99; Gray et al., 2010. *Mol Ther.* 18(3):570-8; Bartel et al., 2012. *Gene Ther.* 19(6):694-700; Marsic & Zolotukhin, 2016. *Methods Mol Biol.* 1382:151-73); and (iii) a chemical capsid modification approach, based on the tethering of chemical groups to the AAV surface (Lee et al., 2005. *Biotechnol Bioeng.* 92:24-34; Maguire et al., 2012. *Mol Ther.* 20:960-71; Hurdy et al., 2016. *Gene Ther.* 23:380-92; Katrekar et al., 2018. *Sci Rep.* 8).

Self-complementary AAVs (scAAVs), in which the expression cassette has been modified to facilitate and accelerate gene expression once in the target cells, have been shown to drive faster onset and higher levels of transgene expression in various tissues, as demonstrated for scAAV9 in the CNS (Foust et al., 2008. *Nat. Biotechnol.* 27:56-65; Gray et al., 2011. *Mol Ther.* 19(6):1058-69). However, the reduced packaging capacities of these vectors over traditional, single stranded AAVs (2.1 kb vs 4.6 kb) limits their usefulness for the treatment of CNS indications.

International patent publication WO2017212019 describes certain surface-modified AAV-derived vectors with improved virus-mediated gene transfer into specific cell types. However, WO2017212019 does not specifically address CNS delivery of these surface-modified AAV vectors.

Here, the Inventors have surprisingly demonstrated that an AAV vector comprising surface-bound saccharides could transduce cells in the CNS. Interestingly, they have shown that the transduction of CNS cells was not only based on the modification of the AAV capsid, but also dependent on the route of administration.

Combining these two criteria, the Inventors have been able to demonstrate widespread transduction of the brain hemisphere with a single injection of these modified AAV vectors directly to the CNS, but not intracerebroventricularly. Thus, among other things, the present disclosure provides particular routes and/or procedures that, when utilized to administer saccharide-conjugated AAVs (i.e., AAVs having surface-bound saccharide(s)) as described herein, can achieve effective and widespread CNS delivery, even from a single administration (e.g., injection).

These results offer a promising outlook for gene therapy in the future, in particular for the treatment of diseases affecting the CNS.

SUMMARY

The present invention relates to a modified adeno-associated virus (AAV) vector for use in transducing a cell in the central nervous system (CNS) of a subject, wherein said modified AAV vector comprises at least one surface-bound saccharide, wherein said modified AAV vector is to be administered directly to the CNS, and wherein said modified AAV vector is not to be administered intracerebroventricularly.

The present invention also relates to a method for transducing a cell in the central nervous system (CNS) of a subject, comprising administering a modified adeno-associated virus (AAV) vector to said subject, wherein said modified AAV vector comprises at least one surface-bound saccharide, wherein said modified AAV vector is administered directly to the CNS, and wherein said modified AAV vector is not administered intracerebroventricularly.

The present invention also relates to a modified adeno-associated virus (AAV) vector for use in the prevention or treatment of a central nervous system (CNS) disease, wherein said modified AAV vector comprises at least one surface-bound saccharide, wherein said modified AAV vector is to be administered directly to the CNS, and wherein said modified AAV vector is not to be administered intracerebroventricularly.

The present invention also includes methods of treating a CNS disease, for example by administering directly to a CNS site, other than by intracerebroventricular injection, an AAV vector that is a modified AAV vector in that it contains at least one surface-conjugated saccharide.

Moreover, the present invention provides improvements for administering an AAV vector to the CNS, including by utilizing an AAV vector that is a modified AAV vector in that it contains at least one surface-conjugated saccharide; and administering the modified AAV vector other than by intracerebroventricular injection. The present disclosure also provides improvements for delivering a transgene to the CNS, for example by including the transgene in an AAV vector that is a modified AAV vector in that it contains at least one surface-conjugated saccharide; and administering the modified AAV vector other than by intracerebroventricular injection.

In one embodiment, said CNS disease is a CNS infectious disease, a CNS degenerative disease, a CNS auto-immune disease, a CNS tumor disease, a cerebrovascular disease, a CNS injury or a CNS structural defect.

In one embodiment, said modified AAV vector is to be administered intrastriatally, intrathalamically or intracisternally.

In one embodiment, said modified AAV vector is selected from AAV1, AAV2, AAV3, AAV4, AAV5, AAV6, AAV7, AAV8, AAV9, AAV10, AAV11 and AAV12; or pseudotypes, chimeras, and variants thereof.

In one embodiment, said modified AAV vector is an AAV2 vector.

In one embodiment, the surface-bound saccharide is selected from the group comprising monosaccharides, oligosaccharides and polysaccharides.

In one embodiment, the surface-bound saccharide is a hexose, preferably a mannose, galactose or N-acetylglucosamine.

As noted above, WO2017212019 describes certain surface-modified AAV-derived vectors with improved virus-mediated gene transfer into specific cell types, which specifically are AAV that are surface modified with certain saccharide moieties. Among other things, the present disclosure expands these teachings, including by demonstrating effective delivery with a range of saccharides and moreover establishing specific utility for CNS delivery as described herein (e.g., particularly when administered other than intracerebroventricularly), including for delivery to a variety of tissues, even distant from a site of administration and/or even after only a single administration (e.g., injection). In one embodiment, the surface-bound saccharide is covalently bound to at least one capsid protein of the AAV vector, preferably to at least one surface-exposed amino acid residue of at least one capsid protein of the AAV vector.

In one embodiment, the surface-bound saccharide is covalently bound through a linker.

In one embodiment, said modified AAV vector comprises at least one transgene.

In one embodiment, said transgene comprises a cDNA, or a fragment thereof, from a gene selected from the group comprising 3R tau, 4R tau, AARS, ABCD1, ACOX1, ADGRV1, ADRA2B, AGA, AGER, ALDH7A1, ALG13, ALS2, ANG, ANXA11, APP, ARHGEF9, ARSA, ARSB, ARV1, ASAH1, ASPA, ATN1, ATP10A, ATP13A2, ATXN1, ATXN2, ATXN3, BAX, BCL-2, BDNF, BICD2, C9orf72, CACNA1A, CACNA1H, CACNB4, CASR, CCNF, CDKL5, CERS1, CFAP410, CHCHD10, CHD2, CHMP2B, CHRNA2, CHRNA4, CHRNA7, CHRNB2, CLCN2a, CLN1, CLN2, CLN3, CLN5, CLN6, CLN8, CNTN2, CPA6, CSTB, CTNS, CTSA, CTSD, DAO, DCTN1, DEPDC5, DMD, DNAJB2, DNM1, DOCK7, DRD2, DYNC1H1, EEF1A2, EFHC1, EGLN1, EPHA4, EPM2A, ERBB4, FGF12, FIG4, FRRS1L, FTL, FUCA1, FUS, FAXN, GAA, GABRA1, GABRB1, GABRB3, GABRD, GABRG2, GAL, GALC, GALNS, GBA, GFAP, GLA, GLB1, GLE1, GLT8D1, GNAO1, GNS, GOSR2, GPR98, GRIA1, GRIA2, GRIK1, GRIN, GRIN2A, GRIN2B, GRIN2D, GSTM1, GUF1, GUSB, HCN1, HGSNAT, HNRNPA1, HTT, HYAL1, IDS, IDUA, IGHMBP2, IL-1, IT15, ITPA, JPH3, KCNA2, KCNB1, KCNC1, KCNMA1, KCNQ2, KCNQ3, KCNT1, KCTD7, LAL, LAMP2, LGI1, LMNB2, LRRK2, MAN2B1, MAN2B2, MAN2C1, MANBA, MATR3, MBD5, MFSD8, NAGA, NAGLU, NECAP1, NEFH, NEK1, NEU1, NHLRC1, NPC1, NPC2, NR4A2, NTRK2, OCA2, OPTN, PARK2, PARK7, PCDH19, PEX1, PEX2, PEX3, PEX5, PEX6, PEX10, PEX11B, PEX12, PEX3, PEX14, PEX16, PEX19, PEX26, PFN1, PINK1, PLCB1, PNPO, PON1, PON2, PON3, PPARGC1A, PRDM8, PRICKLE1, PRKN, PRNP, PRPH, PRRT2, PSAP, S106β, SCARB2, SCN1A, SCN1B, SCN2A, SCN8A, SCN9A, SCN9Ab, SETX, SGSH, SIGMAR1, SIK1, SKP1, SLC1A1, SLC1A2, SLC2A1, SLC6A, SLC9A6, SLC12A5, SLC13A5, SLC25A2, SLC25A22, SLCA17A5, SMN1, SMPD1, SNCA, SNRPN, SOD1, SPG11, SPTAN1, SQSTM1, ST3GAL3, ST3GAL5, STX1B, STXBP1, SYP, SYT1, SZT2, TAF5, TARDBP, TBC1D24, TBCE, TBK1, TBP, TITF-1, TREM2, UBA5, UBE1, UBE3A, UBQLN2, UCH-L1, UNC13A, VAPB, VCP, VPS35, WWOX, and XBP1.

In one embodiment, said CNS disease is selected from the group comprising acid lipase disease, acid maltase deficiency, acid storage disease, acquired epileptiform aphasia, acute disseminated encephalomyelitis, attention deficit hyperactivity disorder (ADHD), Adie's pupil, Adie's syndrome, adrenoleukodystrophy, agnosia, Aicardi syndrome, Aicardi-Goutieres syndrome disorder, Alexander disease, Alpers' disease, alternating hemiplegia, Alzheimer's disease, amyotrophic lateral sclerosis (ALS), anencephaly, aneurysm, Angelman syndrome, angiomatosis, anoxia, antiphospholipid syndrome, aphasia, apraxia, arachnoiditis, Arnold-Chiari malformation, aromatic L-amino acid decarboxylase deficiency (AADC deficiency), aspartylglucosaminuria, Asperger syndrome, ataxia, ataxia telangiectasia (Louis-Bar syndrome), ataxias and cerebellar or spinocerebellar degeneration, attention deficit-hyperactivity disorder, autism, autonomic dysfunction, Barth syndrome, Batten disease, Becker's myotonia, Behcet's disease, Bell's palsy, Bernhardt-Roth syndrome, Binswanger's disease, Bloch-Sulzberger syndrome, Bradbury-Eggleston syndrome, Brown-Sequard syndrome, bulbospinal muscular atrophy, CADASIL, Canavan's disease, causalgia, cavernomas, cavernous angioma, central cervical cord syndrome, central cord syndrome, central pontine myelinolysis, ceramidase deficiency, cerebellar degeneration, cerebellar hypoplasia, cerebral beriberi, cerebral gigantism, cerebral palsy, cerebro-oculo-facio-skeletal syndrome (COFS), cholesterol ester storage disease, chorea, choreoacanthocytosis, chronic inflammatory demyelinating polyneuropathy (CIDP), chronic orthostatic intolerance, chronic pain, Cockayne syndrome type II, Coffin-Lowry syndrome, colpocephaly, congenital myasthenia, corticobasal degeneration, cranial arteritis, cree encephalitis, Creutzfeldt-Jakob disease, Cushing's syndrome, cystinosis, cytomegalic inclusion body disease, dancing eyes-dancing feet syndrome, Dandy-Walker syndrome, Danon disease, Dawson disease, De Morsier's syndrome, Dejerine-Klumpke palsy, dementia, dentate cerebellar ataxia, dentatorubral atrophy, dermatomyositis, developmental dyspraxia, Devic's syndrome, diffuse sclerosis, dysautonomia, dysgraphia, dyslexia, dysphagia, dyspraxia, dyssynergia cerebellaris myoclonica, dyssynergia cerebellaris progressiva, epilepsy (including Amish infantile epilepsy syndrome [AIES], benign familial infantile seizures [BFIS], benign familial neonatal seizures [BFNS], childhood absence epilepsy [CAE], childhood-onset epileptic encephalopathy [COEE], Dravet syndrome [DS], early infantile epileptic encephalopathy [EIEE], familial adult myoclonic epilepsy [FAME], familial febrile seizures [FFS], familial focal epilepsy with variable foci [FFEVF], familial infantile myoclonic epilepsy [FIME], familial temporal lobe epilepsy [FTLE], focal epilepsy and speech disorder [FESD] with or without mental retardation, generalized epilepsy and paroxysmal dyskinesia [GEPD], generalized epilepsy with febrile seizures plus [GEFS+], idiopathic generalized epilepsy [IGE], juvenile absence epilepsy [JAE], juvenile myoclonic epilepsy [JME], myoclonic-atonic epilepsy [MAE], nocturnal frontal lobe epilepsy [NFLE], progressive myoclonic epilepsy [PME], pyridoxamine 5'-phosphate oxidase deficiency [PNPOD], pyridoxine-dependent epilepsy [EPD] and severe myoclonic epilepsy of infancy [SMEI]), Fabry disease, Fahr's syndrome, familial dysautonomia, familial hemangioma, familial idiopathic basal ganglia calcification, familial periodic paralyses, familial spastic paralysis, Farber's disease, fibromuscular dysplasia, Fisher syndrome, floppy infant syndrome, Friedreich's ataxia, frontotemporal dementia, fucosidosis, galactosialidosis, Gaucher disease, generalized gangliosidosis, Gerstmann's syndrome, Gerstmann-Straussler-Scheinker disease, giant axonal neuropathy, giant cell arteritis, giant cell inclusion disease, globoid cell leukodystrophy, glossopharyngeal neuralgia, glycogen storage disease, GM1 gangliosidosis, GM2 gangliosidosis (Tay-Sachs disease), Guillain-Barre syndrome, Hallervorden-Spatz disease, hemicrania continua, hemiplegia alterans, hereditary spastic paraplegia, heredopathia atactica polyneuritiformis, Holmes-Adie syndrome, holoprosencephaly, Hughes syndrome, Huntington's disease, hydranencephaly, hydromyelia, hypercortisolism, immune-mediated encephalomyelitis, inclusion body myositis, incontinentia pigmenti, infantile hypotonia, infantile neuroaxonal dystrophy, iniencephaly, Isaac's syndrome, Joubert syndrome, Kearns-Sayre syndrome, Kennedy's disease, Kinsbourne syndrome, Kleine-Levin syndrome, Klippel-Feil syndrome, Klippel-Trenaunay syndrome (KTS), Kliiver-Bucy syndrome, Korsakoff's amnesic syndrome, Krabbe disease, Kugelberg-Welander disease, Lambert-Eaton myasthenic syndrome, Landau-Kleffner syndrome, lateral femoral cutaneous nerve entrapment, lateral medullary syndrome, Leigh's disease, Lennox-Gastaut syndrome, Lesch-Nyhan syndrome, Levine-Critchley syndrome, Lewy body dementia, lipoid proteinosis, lissencephaly, locked-in syndrome, Lou Gehrig's disease, lupus, Lyme disease, Machado-Joseph disease, macrencephaly, alpha-mannosidosis, beta-mannosidosis, Melkersson-Rosenthal syndrome, Menkes disease, meralgia paresthetica, metachromatic leukodystrophy, microcephaly, Miller Fisher syndrome, Moebius syndrome, mucopolysaccharidosis type I-H (Hurler syndrome), mucopolysaccharidosis type I-H/S (Hurler-Scheie syndrome), mucopolysaccharidosis type IS (Scheie syndrome), mucopolysaccharidosis type II (Hunter syndrome), mucopolysaccharidosis type III-A (Sanfilippo syndrome A), mucopolysaccharidosis type III-B (Sanfilippo syndrome B), mucopolysaccharidosis type III-C(Sanfilippo syndrome C), mucopolysaccharidosis type III-D (Sanfilippo syndrome D), mucopolysaccharidosis type IV-B (Morquio syndrome B), mucopolysaccharidosis type VI (Maroteaux-Lamy syndrome), mucopolysaccharidosis type VII (Sly syndrome), mucopolysaccharidosis type IX (Natowicz syndrome), multiple sclerosis, muscular dystrophy, myasthenia gravis, myelinoclastic diffuse sclerosis, narcolepsy, neuroacanthocytosis, neurofibromatosis, neuroleptic malignant syndrome, neurosarcoidosis, Niemann-Pick disease, Ohtahara syndrome, olivopontocerebellar atrophy, opsoclonus myoclonus, O'Sullivan-McLeod syndrome, pantothenate kinase-associated neurodegeneration, paraneoplastic syndromes, paresthesia, Parkinson's disease, paroxysmal choreoathetosis, paroxysmal hemicrania, Parry-Romberg syndrome, Pelizaeus-Merzbacher disease, Pena Shokeir II syndrome, periventricular leukomalacia, phytanic acid storage disease, Pick's disease, piriformis syndrome, polymyositis, Pompe disease, post-polio syndrome, posterior cortical atrophy, primary dentatum atrophy, primary lateral sclerosis, primary progressive aphasia, prion diseases, progressive hemifacial atrophy, progressive locomotor ataxia, progressive multifocal leukoencephalopathy, progressive sclerosing poliodystrophy, progressive supranuclear palsy, prosopagnosia, Ramsay Hunt syndrome I, Ramsay Hunt syndrome II, Rasmussen's encephalitis, Refsum disease, Rett syndrome, Reye's syndrome, Riley-Day syndrome, Sandhoff disease, Schilder's disease, Seitelberger disease, Shy-Drager syndrome, Sjogren's syndrome, spasticity, spina bifida, spinal muscular atrophy, spinocerebellar ataxia, spinocerebellar atrophy, spinocerebellar degeneration, Steele-Richardson-Olszewski syndrome, striatonigral degeneration, Sturge-Weber syndrome, tardive dyskinesia, tauopathy, Tay-Sachs disease, thoracic outlet syndrome, thyrotoxic myopathy, tic douloureux, Todd's paralysis, trigeminal neuralgia, tropical spastic paraparesis, Troyer syndrome, vascular dementia, Von Economo's disease, Von Hippel-Lindau disease (VHL), Von Recklinghausen's disease, Wallenberg's syndrome, Werdnig-Hoffman disease, Wernicke-Korsakoff syndrome, West syndrome, Whipple's disease, Williams syndrome, Wilson disease, Wolman's disease, X-linked spinal and bulbar muscular atrophy, and Zellweger syndrome.

In one embodiment, said transgene is under control of a CAG promoter.

The present invention relates to a modified adeno-associated virus (AAV) vector comprising at least one transgene, wherein said modified AAV comprises at least one surface-bound saccharide, and wherein said transgene comprises a cDNA, or a fragment thereof, from a gene selected from the group comprising 3R tau, 4R tau, AARS, ABCD1, ACOX1, ADGRV1, ADRA2B, AGA, AGER, ALDH7A1, ALG13, ALS2, ANG, ANXA11, APP, ARHGEF9, ARSA, ARSB, ARV1, ASAH1, ASPA, ATN1, ATP10A, ATP13A2, ATXN1, ATXN2, ATXN3, BAX, BCL-2, BDNF, BICD2, C9orf72, CACNA1A, CACNA1H, CACNB4, CASR, CCNF, CDKL5, CERS1, CFAP410, CHCHD10, CHD2, CHMP2B, CHRNA2, CHRNA4, CHRNA7, CHRNB2, CLCN2a, CLN1, CLN2, CLN3, CLN5, CLN6, CLN8, CNTN2, CPA6, CSTB, CTNS, CTSA, CTSD, DAO, DCTN1, DEPDC5, DMD, DNAJB2, DNM1, DOCK7, DRD2, DYNC1H1, EEF1A2, EFHC1, EGLN1, EPHA4, EPM2A, ERBB4, FGF12, FIG. 4, FRRS1L, FTL, FUCA1, FUS, FAXN, GAA, GABRA, GABRB1, GABRB3, GABRD, GABRG2, GAL, GALC, GALNS, GBA, GFAP, GLA, GLB1, GLE1, GLT8D1, GNAO1, GNS, GOSR2, GPR98, GRIA1, GRIA2, GRIK1, GRIN1, GRIN2A, GRIN2B, GRIN2D, GSTM1, GUF1, GUSB, HCN1, HGSNAT, HNRNPA1, HTT, HYAL1, IDS, IDUA, IGHMBP2, IL-1, IT15, ITPA, JPH3, KCNA2, KCNB1, KCNC1, KCNMA1, KCNQ2, KCNQ3, KCNT1, KCTD7, LAL, LAMP2, LGI1, LMNB2, LRRK2, MAN2B1, MAN2B2, MAN2C1, MANBA, MATR3, MBD5, MFSD8, NAGA, NAGLU, NECAP1, NEFH, NEK1, NEU1, NHLRC1, NPC1, NPC2, NR4A2, NTRK2, OCA2, OPTN, PARK2, PARK7, PCDH19, PEX, PEX2, PEX3, PEX5, PEX6, PEX10, PEX11B, PEX12, PEX3, PEX14, PEX16, PEX19, PEX26, PFN1, PINK1, PLCB1, PNPO, PON1, PON2, PON3, PPARGC1A, PRDM8, PRICKLE1, PRKN, PRNP, PRPH, PRRT2, PSAP, S106β, SCARB2, SCN1A, SCN1B, SCN2A, SCN8A, SCN9A, SCN9Ab, SETX, SGSH, SIGMAR1, SIK1, SKP1, SLC1A1, SLC1A2, SLC2A1, SLC6A, SLC9A6, SLC2A5, SLC13A5, SLC25A2, SLC25A22, SLCA17A5, SMN1, SMPD1, SNCA, SNRPN, SOD1, SPG11, SPTAN1, SQSTM1, ST3GAL3, ST3GAL5, STX1B, STXBP1, SYP, SYT1, SZT2, TAF5, TARDBP, TBC1D24, TBCE, TBK1, TBP, TITF-1, TREM2, UBA5, UBE1, UBE3A, UBQLN2, UCH-L1, UNC13A, VAPB, VCP, VPS35, WWOX, and XBP1; preferably under control of a promoter.

The present invention relates to a kit or kit-of-parts suitable for:
  transducing a cell in the central nervous system (CNS) of a subject; and/or
  delivering a transgene to the central nervous system (CNS) of a subject; and/or
  preventing and/or treating a central nervous system (CNS) disease in a subject,
  said kit comprising:
  (a) the modified AAV vector according to the present invention,
  (b) a device for CNS delivery of the modified AAV vectors, and
  (c) optionally, instructions for CNS delivery of the modified AAV vector.

DETAILED DESCRIPTION

Among other things, the present disclosure provides an insight that development of an AAV system with wider transduction properties could be particularly useful and could address the source of a problem with existing AAV strategies, especially in the context of CNS diseases that may involve cells scattered throughout the CNS.

Among other things, the present disclosure provides an insight that an AAV vector capable of achieving widespread transduction from a single, or very few, local administration point(s) in the CNS would be advantageous and would solve a source of a problem with certain existing AAV strategies which for example may require or typically involve injection to multiple sites in the CNS.

Among other things, the present disclosure provides an insight that an AAV vector capable of avoiding immune detection, while ensuring both cell-specific and widespread transduction in the CNS, would be advantageous and would solve a source of a problem with certain existing AAV strategies triggering immune responses.

The present invention relates to a modified adeno-associated virus (AAV) vector for use in transducing a cell in the central nervous system (CNS) of a subject,
  wherein said modified AAV vector comprises at least one surface-bound saccharide,
  wherein said modified AAV vector is to be administered directly to the CNS, and
  wherein said modified AAV vector is not to be administered intracerebroventricularly.

The present invention also relates to the use of a modified adeno-associated virus (AAV) vector for transducing a cell in the central nervous system (CNS) of a subject,
  wherein said modified AAV vector comprises at least one surface-bound saccharide,
  wherein said modified AAV vector is to be administered directly to the CNS, and wherein said modified AAV vector is not to be administered intracerebroventricularly.

The present invention also relates to a method of administering a modified adeno-associated virus (AAV) into a plurality of brain tissues in the central nervous system (CNS) of a subject, the method comprising administering a modified adeno-associated virus (AAV) vector comprising said transgene to said subject, wherein said modified AAV vector comprises at least one surface-bound saccharide, wherein said modified AAV vector is administered directly to a CNS site and at least one of the plurality of brain tissues is distant from the CNS site, and wherein said modified AAV vector is not administered intracerebroventricularly.

In some embodiments, the brain tissues may be or include the striatum, the thalamus, the substantia nigra, the parietal cortices, the hippocampus and/or the globus pallidus. In some embodiments, the CNS site may be in the striatum. In some embodiments, the CNS site may be in the thalamus. In some embodiments, the CNS site may be in the cisterna magna. In some embodiments, the administering may be to a single CNS site. In some embodiments, the administering may be to a plurality of CNS sites, selected from the group consisting of the striatum and thalamus, and combinations thereof, or from the group consisting of the striatum and thalamus and cisterna magna and combinations thereof. In some embodiments, the administering may be by a single injection.

The present invention also relates to a method for transducing a cell in the central nervous system (CNS) of a subject, comprising administering a modified adeno-associated virus (AAV) vector to said subject,
wherein said modified AAV vector comprises at least one surface-bound saccharide,
wherein said modified AAV vector is administered directly to the CNS, and
wherein said modified AAV vector is not administered intracerebroventricularly.

The present invention also relates to a method for delivering a transgene into a cell in the central nervous system (CNS) of a subject, comprising administering a modified adeno-associated virus (AAV) vector comprising said transgene to said subject,
wherein said modified AAV vector comprises at least one surface-bound saccharide,
wherein said modified AAV vector is administered directly to the CNS, and
wherein said modified AAV vector is not administered intracerebroventricularly.

The present invention also relates to a method for delivering a transgene into a plurality of brain tissues in the central nervous system (CNS) of a subject, the method comprising administering a modified adeno-associated virus (AAV) vector comprising said transgene to said subject,
wherein said modified AAV vector comprises at least one surface-bound saccharide,
wherein said modified AAV vector is administered directly to a CNS site and at least one of the plurality of brain tissues is distant from the CNS site, and
wherein said modified AAV vector is not administered intracerebroventricularly.

In some embodiments, the brain tissues may be or include the striatum, the thalamus, the substantia nigra, the parietal cortices, the hippocampus and/or the globus pallidus. In some embodiments, the CNS site may be in the striatum. In some embodiments, the CNS site may be in the thalamus. In some embodiments, the CNS site may be in the cisterna magna. In some embodiments, the administering may be to a single CNS site. In some embodiments, the administering may be to a plurality of CNS sites, selected from the group consisting of the striatum and thalamus, and combinations thereof, or from the group consisting of the striatum and thalamus and intra-cisterna magna and combinations thereof. In some embodiments, the administering may be by a single injection.

The present invention further relates to an in vitro method for transducing a neuronal cell, comprising contacting said neuronal cell with a modified adeno-associated virus (AAV) vector, wherein said modified AAV vector comprises at least one surface-bound saccharide.

As used herein, the term "central nervous system" or "CNS" refers to both the brain and the spinal cord and contrasts with the "peripheral nervous system" or "PNS" which excludes the brain and the spinal cord.

As used herein, the term "subject" refers to a mammal, preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease.

The term "mammal" refers here to any mammal, including humans, domestic and farm animals, and zoo, sports, or pet animals, such as dogs, cats, cattle, horses, sheep, pigs, goats, rabbits, etc. Preferably, the mammal is a primate, more preferably a human.

AAV vectors suitable in the present invention may comprise or be derived from any natural or recombinant AAV serotype.

In one embodiment, the AAV vector according to the present invention is selected from natural serotypes AAV1, AAV2, AAV3, AAV4, AAV5, AAV6, AAV7, AAV8, AAV9, AAV10, AAV11 and AAV12; or pseudotypes, chimeras, and variants thereof.

As used herein, the term "pseudotype" when referring to an AAV vector, or a "pseudotyped AAV vector", refers to an AAV vector which comprises the genome of one AAV serotype packaged in the capsid of another AAV serotype. These pseudotypes are denoted using a slash or a hyphen, so that "AAV2/5" or "AAV2-5" indicates an AAV vector comprising a serotype 2 genome, packaged into a serotype 5 capsid.

Examples of pseudotyped AAV vectors include, but are not limited to, AAV2/1, AAV2/2, AAV2/3, AAV2/4, AAV2/5, AAV2/6, AAV2/7, AAV2/8 and AAV2/9.

As used herein, the term "chimera" when referring to an AAV vector, or a "chimeric AAV vector", refers to an AAV vector which comprises a capsid containing VP1, VP2 and VP3 proteins from at least two different AAV serotypes; or alternatively, which comprises VP1, VP2 and VP3 proteins, at least one of which comprises at least a portion from another AAV serotype.

Examples of chimeric AAV vectors include, but are not limited to, AAV-DJ, AAV2G9, AAV2i8, AAV2i8G9, AAV8G9, and AAV9i1.

In one embodiment, the AAV vector according to the present invention is selected from the group comprising or consisting of AAV1, AAV2, AAV3, AAV4, AAV5, AAV6, AAV7, AAV8, AAV9, AAV10, AAV11, AAV12, AAV106.1/hu.37, AAV114.3/hu.40, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2i8, AAV2i8G9, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV2.5T, AAV27.3, AAV29.3/bb.1, AAV29.5/bb.2, AAV2G9, AAV3B, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/rh.64, AAV4-9/rh.54, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6.1, AAV6.1.2, AAV6.2, AAV7m8, AAV7.2, AAV7.3/hu.7, AAV-8b, AAV8G9, AAV-8h, AAV9i1, AAV9.11, AAV9.13, AAV9.16, AAV9.24, AAV9.45, AAV9.47, AAV9.61, AAV9.68, AAV9.84, AAV9.9, AAVcy.2, AAVcy.3, AAVcy.4, AAVcy.5, AAVcy.5R1, AAVcy.5R2, AAVcy.5R3, AAVcy.5R4, AAVcy.6, AAVhu.1, AAVhu.2, AAVhu.3, AAVhu.4, AAVhu.5, AAVhu.6, AAVhu.7, AAVhu.8, AAVhu.9, AAVhu.10, AAVhu.11, AAVhu.12, AAVhu.13, AAVhu.14/9, AAVhu.15, AAVhu.16, AAVhu.17, AAVhu.18, AAVhu.19, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.53, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVpi.1, AAVpi.2, AAVpi.3, AAVrh.2, AAVrh.2R, AAVrh.8, AAVrh.8R, AAVrh8R R533A mutant, AAVrh8R A586R mutant, AAVrh.10, AAVrh.12, AAVrh.13, AAVrh. 13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAV-PHP.B, AAV-PHP.A, AAV-G2B-26, AAV-G2B-13, AAV-TH1.1-32, AAV-TH1.1-35, AAV-PHP.B2, AAV-PHP.B3, AAV-PHP.N/PHP.B-DGT, AAV-PHP.B-EST, AAV-PHP.B-GGT, AAV-PHP.B-ATP, AAV-PHP.B-ATT-T, AAV-PHP.B-DGT-T, AAV-PHP.B-GGT-T, AAV-PHP.B-SGS, AAV-PHP.B-AQP, AAV-PHP.B-QQP, AAV-PHP.B-SNP(3), AAV-PHP.B-SNP, AAV-PHP.B-QGT, AAV-PHP.B-NQT, AAV-PHP.B-EGS, AAV-PHP.B-SGN, AAV-PHP.B-EGT, AAV-PHP.B-DST, AAV-PHP.B-DST, AAV-PHP.B-STP, AAV-PHP.B-PQP, AAV-PHP.B-SQP, AAV-PHP.B-QLP, AAV-PHP.B-TMP, AAV-PHP.B-TTP, AAV-PHP.S/G2A12, AAV-G2A15/G2A3, AAV-G2B4, AAV-G2B5, PHP.S, AAAV, AAV A3.3, AAV A3.4, AAV A3.5, AAV A3.7, AAV CBr-7.3, AAV CBr-7.1, AAV CBr-7.10, AAV CBr-7.2, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-N4, AAV CKd-N9, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-M9, AAV CLv-R6, AAV CLv-1, AAV CLv1-1, AAV CLv1-10, AAV CLv1-2, AAV CLv-12, AAV CLv1-3, AAV CLv-13, AAV CLv1-4, AAV CLv1-7, AAV CLv1-8, AAV CLv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-R1, AAV CLv-R2, AAV CLv-R3, AAV CLv-R4, AAV CLv-R5, AAV CLv-R7, AAV CLv-R8, AAV CLv-R9, AAV CSp-8.10, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV-LK08, AAV-LK15, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, AAV SM 10-8, AAV.VR-355, AAV-b, AAVC1, AAVC2, AAVC5, AAVCh.5, AAVCh.5R1, AAV-DJ, AAV-DJ8, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3, AAVF3/HSC3, AAVF4/HSC4, AAVF5, AAVF5/HSC5, AAVF6/HSC6, AAVF7/HSC7, AAVF8/HSC8, AAVF9/HSC9, AAV-h, AAVH-1/hu.1, AAVH2, AAVH-5/hu.3, AAVH6, AAVhE1.1, AAVhEr1.14, AAVhEr1.16, AAVhEr1.18, AAVhER1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVLG-10/rh.40, AAVLG-4/rh.38, AAVLG-9/hu.39, AAVLG-9/hu.39, AAV-LK01, AAV-LK02, AAV-LK03, AAV-LK03, AAV-LK04, AAV-LK05, AAV-LK06, AAV-LK07, AAV-LK09, AAV-LK10, AAV-LK11, AAV-LK12, AAV-LK13, AAV-LK14, AAV-LK16, AAV-LK17, AAV-LK18, AAV-LK19, AAVN721-8/rh.43, AAV-PAEC, AAV-PAEC 12, AAV-PAEC11, AAV-PAEC2, AAV-PAEC4, AAV-PAEC6, AAV-PAEC7, AAV-PAEC8, Anc80, Anc80L65, Anc81, Anc82, Anc83, Anc84, Anc94, Anc110, Anc113, Anc126, Anc127, BAAV, BNP61 AAV, BNP62 AAV, BNP63 AAV, bovine AAV, caprine AAV, Japanese AAV 10 serotype, UPENN AAV10, VOY101, and VOY201.

In one embodiment, AAV variants include vectors which have been genetically modified, e.g., by substitution, deletion or addition of one or several amino acid residues in one of the capsid proteins. Examples of such variants include, but are not limited to, AAV2 with any or several of Y444F, Y500F, Y730F and/or S662V mutations; AAV3 with any or several of Y705F, Y731F and/or T492V mutations; AAV6 with any or several of S663V and/or T492V mutations.

In one embodiment, the AAV vector according to the present invention is AAV2.

In one embodiment, the AAV vector according to the present invention is AAV5.

In one embodiment, the AAV vector according to the present invention is AAV6.

In one embodiment, the AAV vector according to the present invention is AAV8.

In one embodiment, the AAV vector according to the present invention is AAV9.

In one embodiment, the AAV vector according to the present invention is AAVrh.10.

In one embodiment, the AAV vector according to the present invention is Anc80L65.

According to the present invention, the modified AAV vector comprises at least one surface-bound saccharide or a derivative thereof.

As used herein, the term "surface-bound", when referring to the at least one saccharide, means that said at least one saccharide is bound to and exposed at the outer surface of the AAV vector.

Suitable examples of saccharides include, but are not limited to, monosaccharides, oligosaccharides, polysaccharides, and derivatives thereof.

As used herein, the term "derivatives" when referring to monosaccharides, oligosaccharides or polysaccharides, is meant to encompass saccharides containing one or more non-hydroxyl group(s). Examples of such non-hydroxyl groups include, but are not limited to, a hydrogen, an alkyl, an amino group (such as e.g. NH2, an alkyl amino, a dialkyl amino), an N-acetylamino group and/or a thiol group.

Monosaccharides, also called "simple sugar", are the simplest form of sugar and the most basic units of carbohydrates. Monosaccharides can be classified by the number x of carbon atoms they contain, from 3 (trioses), 4 (tetroses), 5 (pentoses), 6 (hexoses), 7 (heptoses), and so on.

Examples of monosaccharides include, but are not limited to, glycolaldehyde, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, and sedoheptulose.

Deoxymonosaccharides are common derivatives of monosaccharides encompassed in the present invention, i.e., monosaccharides that have had a hydroxyl group replaced with a hydrogen atom.

Examples of deoxymonosaccharides include, but are not limited to, deoxyribose, fucose, fuculose, rhamnose, quinovose, pneumose.

2-amino-2-deoxymonosaccharides are also common derivatives of monosaccharides encompassed in the present invention, i.e., monosaccharides that have had a hydroxyl group replaced with an amino group.

Examples of 2-amino-2-deoxymonosaccharides include, but are not limited to, glucosamine, galactosamine, and daunosamine, as well as their acetylated forms, including, but not limited to, N-acetylglucosamine, and N-acetylgalactosamine.

It is to be understood that the monosaccharides and derivatives thereof mentioned herein also encompass acyclic (open-chain) forms and cyclic forms.

It is also to be understood that the monosaccharides and derivatives thereof mentioned herein also encompass D-stereoisomers and L-stereoisomers, as well as racemic mixtures of D- and L-stereoisomers.

It is also to be understood that the monosaccharides and derivatives thereof mentioned herein also encompass α-anomers and β-anomers, as well as racemic mixtures of α- and β-anomers.

Oligosaccharides are saccharide polymers comprising a small number (typically from two to ten) of monosaccharides.

In one embodiment, the oligosaccharide according to the present invention comprises at least two, three, four, five, six, seven, eight, nine or ten monosaccharides chosen among the monosaccharides disclosed hereinabove, including their derivatives. Such oligosaccharide can be a homooligosaccharides (i.e., composed of the same monosaccharide units, including their derivatives) or heterooligosaccharides (i.e., composed of at least two different monosaccharides, including their derivatives).

Examples of oligosaccharides include, but are not limited to, disaccharides, trisaccharides, tetrasaccharides, pentasaccharides, hexasaccharides, heptasaccharides, octasaccharides, nonasaccharides and decasaccharides.

Specific examples of disaccharides include, but are not limited to, cellobiose, chitobiose, gentiobiose, gentiobiulose, isomaltose, kojibiose, lactose, lactulose, laminaribiose, maltose, maltulose, mannobiose, melibiose, melibiulose, nigerose, palatinose, rutinose, rutinulose, sophorose, sucrose, trehalose, turanose and xylobiose.

Specific examples of trisaccharides include, but are not limited to, kestose, maltotriose, maltotriulose, melezitose, nigerotriose and raffinose.

Specific examples of tetrasaccharides include, but are not limited to, lychnose, maltotetraose, nigerotetraose, nystose, sesamose and stachyose.

Other specific examples of oligosaccharides include, but are not limited to, acarbose, fructooligosaccharide, galactooligosaccharide, isomaltooligosaccharide and maltodextrin.

Polysaccharides are saccharide polymers comprising a large number (typically more than ten) of monosaccharides. They range in structure from linear to highly branched.

In one embodiment, the polysaccharide according to the present invention comprises more than ten monosaccharides (such as, e.g., 11, 12, 13, 14, 15, 16, 17, 18, 19, 20 or more) chosen among the monosaccharides disclosed hereinabove, including their derivatives. In a similar way as described above for oligosaccharides, polysaccharides can be homopolysaccharides or heteropolysaccharides.

Examples of polysaccharides include, but are not limited to, beta-glucans, lentinan, sizofiran, zymosan, cellulose, hemicellulose, chitin, chitosan, dextrins, dextran, fructan, inulin, galactan, glucan, glycogen, levan β2→6, lignin, mannan, pectin, starch, amylopectin, amylose and xanthan gum.

In one embodiment, the saccharide or derivative thereof according to the present invention is a monosaccharide, preferably a hexose. More preferably the saccharide or derivative thereof according to the present invention is mannose, galactose or N-acetylglucosamine.

In one embodiment, the saccharide or derivative thereof is mannose. In one embodiment, the saccharide or derivative thereof is galactose. In one embodiment, the saccharide or derivative thereof is N-acetylglucosamine.

In one embodiment, the saccharide or derivative thereof according to the present invention is a deoxymonosaccharide, preferably fucose.

In other embodiments, the saccharide or derivative thereof is a saccharide containing a non-hydroxyl group which is a dialkyl amino group, preferably a desosamine.

In one embodiment, the at least one surface-bound saccharide or a derivative thereof is covalently bound to the AAV vector. In one embodiment, the at least one surface-bound saccharide or a derivative thereof is not covalently bound to the AAV vector.

In one embodiment, the at least one surface-bound saccharide or a derivative thereof is covalently bound to the AAV vector through a linker or spacer. In one embodiment, the at least one surface-bound saccharide or a derivative thereof is not covalently bound to the AAV vector through a linker or spacer.

The present invention is not limited to any particular linker or spacer. The use of a variety of linkers or spacers is contemplated, including, but not limited to, alkyl, ether, polyether, alkyl amide or a combination thereof. The use of a variety of alkyls is contemplated, including, but not limited to, —$(CH_2)_n$—, wherein "n" is from about 2 to about 20 or more.

The use of a variety of ethers and polyethers is contemplated, including, but not limited to, —$(OCH_2CH_2)_n$—, wherein "n" is from about 1 to about 20 or more. The use of a variety of alkyl amides is contemplated, including, but not limited to, —$(CH_2)_m$—C(O)NH—$(CH_2)_n$— and —$(OCH_2CH_2)_m$—C(O)NH—$(OCH_2CH_2)_n$—, wherein "m" and "n" can be the same or different and "m" and "n" are from about 1 to about 20 or more. The use of a variety of amides having the linking units of alkyl or ether bonds is contemplated, including, but not limited to, —$R_1$—C(O)NH—$R_2$—, wherein "$R_1$" and "$R_2$" are alkyls, ethers, or polyethers.

Certain examples of suitable linkers or spacer are described in WO2017212019.

In one embodiment, the linker is a poly-ethylene glycol (PEG)-based linker, such as e.g. a linker comprising a PEG3 spacer of formula —$(OCH_2CH_2)_3$—, or a linker comprising a PEG5 spacer of formula —$(OCH_2CH_2)_5$—.

In some embodiments, the linker further comprises one or more aromatic group such as e.g. a phenyl. In one embodiment, the at least one surface-bound saccharide or a derivative thereof is covalently bound to at least one capsid protein of the AAV vector.

AAV vectors are composed of a mixture of three capsid proteins, named VP1, VP2 and VP3.

In one embodiment, the at least one surface-bound saccharide or a derivative thereof is covalently bound to at least one VP1 protein of the AAV vector. In one embodiment, the at least one surface-bound saccharide or a derivative thereof is covalently bound to at least one VP2 protein of the AAV vector. In one embodiment, the at least one surface-bound saccharide or a derivative thereof is covalently bound to at least one VP3 protein of the AAV vector.

In one embodiment, the at least one surface-bound saccharide or a derivative thereof is covalently bound to at least one surface-exposed amino acid residue of at least one capsid protein of the AAV vector.

As used herein, the term "surface-exposed" refers to an amino acid residue with a side chain that is at least partially exposed at the outer surface of the AAV vector.

In one embodiment, the at least one surface-bound saccharide or a derivative thereof is covalently bound to at least one surface-exposed amino acid residue containing a functional group of at least one capsid protein of the AAV vector.

As used herein, the term "amino acid residue containing a functional group" refers to amino acid residues comprising an amine group, a thiol group, an amide group, a hydroxyl group or the like.

In one embodiment, the amino acid residue containing a functional group is any one of arginine, asparagine, aspartic acid, cysteine, glutamic acid, glutamine, histidine, lysine, serine, threonine, tryptophan, tyrosine, and mixtures thereof.

In a preferred embodiment, the at least one surface-bound saccharide or a derivative thereof is covalently bound to at least one surface-exposed lysine residue of at least one capsid protein of the AAV vector.

Means and methods for covalently coupling a saccharide to an AAV vector, such as to a surface-exposed amino acid residue of a capsid protein of an AAV vector, are well known in the art. Such methods include, e.g., conjugation with activated esters, sulfonyl chlorides or isothiocyanates; reductive alkylation; aza-Michael addition; azetidinone chemistry; benzoyl fluoride-based plug-and-play chemistry; or click chemistry. Examples are given in, e.g., Sletten & Bertozzi, 2009. *Angew Chem Int Ed Engl.* 48(38):6974-98.

Non-limiting examples of coupling reactions are shown on FIG. 17A. To better illustrate said coupling reactions, non-limiting examples of coupling reactions between a saccharide moiety (such as e.g. mannose, herein taken as a non-limiting example of a saccharide moiety) and a AAV surface-exposed primary amine (such as e.g. NH2), are shown on FIG. 17B.

According to the present invention, the modified AAV vectors is to be administered directly to the CNS.

By "administered directly to the CNS", it is meant administered intraspinally or intracerebrally.

In one embodiment, the modified AAV vectors according to the present invention may be administered by intraspinal and/or intracerebral administration.

In one embodiment, the modified AAV vector according to the present invention is to be administrated intraspinally.

In one embodiment, intraspinal administration comprises or consists of intrathecal and epidural administration.

In one embodiment, intraspinal administration comprises or consists of intrathecal administration.

In one embodiment, the modified AAV vector according to the present invention is to be administrated intracerebrally.

In one embodiment, intracerebral administration is at a site selected from the group comprising or consisting of: striatum (such as, e.g., putamen, caudate nucleus, nucleus accumbens, olfactory tubercle, external globus pallidus and/or internal globus pallidus), thalamus, hypothalamus, epithalamus, subthalamus, parenchyma, cerebrum, medulla, deep cerebellar nuclei (such as, e.g., substantia nigra, dentate, emboliform, globose and/or fastigii nucleus), cerebrospinal fluid (CSF), meninges, dura mater, arachnoid mater, pia mater, subarachnoid cisterns (such as, e.g., cisterna magna, pontine cistern, interpeduncular cistern, chiasmatic cistern, cistern of lateral cerebral fossa, superior cistern and/or cistern of lamina terminalis), subarachnoid space, cortex, septum, pons, and cerebellum.

In one embodiment, the modified AAV vector according to the present invention is to be administrated intrastriatally (i.e., in the striatum, such as, e.g., in the putamen, caudate nucleus, nucleus accumbens, olfactory tubercle, external globus pallidus and/or internal globus pallidus), intrathalamically (i.e., in the thalamus), intracisternally (i.e., in the subarachnoid cisterns, such as, e.g., in the cisterna magna, pontine cistern, interpeduncular cistern, chiasmatic cistern, cistern of lateral cerebral fossa, superior cistern and/or cistern of lamina terminalis; preferably in the cisterna magna).

In one embodiment, the modified AAV vector according to the present invention is to be administered intraparenchymally.

In one embodiment, the modified AAV vector according to the present invention is to be administrated intrastriatally, intrathalamically, intracisternally or intrathecally.

In one embodiment, the modified AAV vector according to the present invention is to be administrated intrastriatally or intrathalamically.

According to the present invention, the modified AAV vector is not to be administered intracerebroventricularly (i.e., not in the ventricular system, such as, e.g., not in the right lateral ventricle, left lateral ventricle, third ventricle and/or fourth ventricle).

It is to be understood that the terms "administration" or "administered", as used herein, are meant to encompass injections and infusions, and any other means of administration known by the one skilled in the art.

In one embodiment, the modified AAV vectors according to the present invention specifically transduce any or several of the following cells: neurons (such as, e.g., pyramidal neurons, Purkinje neurons, spindle neurons, medium spiny neurons, and/or interneurons [e.g., Golgi cells, Lugaro cells, basket cells, stellate cells, candelabrum cells, unipolar brush cells, granule cells, Renshaw cells, 1a inhibitory neurons, 1b inhibitory neurons, parvalbumin-expressing interneurons, CCK-expressing interneurons, VIP-expressing interneurons, SOM-expressing interneurons, cholinergic interneurons, tyrosine hydroxylase-expressing interneurons, calretinin-expressing interneurons, or nitric oxide synthase-expressing interneurons]), oligodendrocytes, astrocytes, microglial cells, ependymal cells, radial glia cells and/or pituicytes.

In one embodiment, the modified AAV vectors according to the present invention specifically transduce any or several of the following cells: neurons (such as, e.g., pyramidal neurons, Purkinje neurons, spindle neurons, medium spiny neurons, and/or interneurons [e.g., Golgi cells, Lugaro cells, basket cells, stellate cells, candelabrum cells, unipolar brush cells, granule cells, Renshaw cells, 1a inhibitory neurons, 1b inhibitory neurons, parvalbumin-expressing interneurons, CCK-expressing interneurons, VIP-expressing interneurons, SOM-expressing interneurons, cholinergic interneurons, tyrosine hydroxylase-expressing interneurons, calretinin-expressing interneurons, or nitric oxide synthase-expressing interneurons]).

In one embodiment, the modified AAV vectors according to the present invention do not specifically transduce any or several of the following cells: oligodendrocytes, astrocytes, microglial cells, ependymal cells, radial glia cells and/or pituicytes.

The modified AAV vector described herein may be particularly useful in gene therapy.

Accordingly, the present invention also relates to the modified AAV vector according to the present invention, for use in gene therapy,
wherein said modified AAV vector comprises at least one surface-bound saccharide,
wherein said modified AAV vector is to be administered intracerebrally, and
wherein said modified AAV vector is not to be administered intracerebroventricularly.

The present invention also relates to a method of gene therapy in a subject in need thereof, comprising administering the modified AAV vector according to the present invention to said subject,
wherein said modified AAV vector comprises at least one surface-bound saccharide,
wherein said modified AAV vector is administered intracerebrally, and
wherein said modified AAV vector is not administered intracerebroventricularly.

In particular, the modified AAV vector described herein may be particularly useful for preventing and/or treating a CNS disease.

Accordingly, the present invention also relates to the modified AAV vector according to the present invention, for use in the prevention or treatment of a CNS disease,
wherein said modified AAV vector comprises at least one surface-bound saccharide,
wherein said modified AAV vector is to be administered intracerebrally, and
wherein said modified AAV vector is not to be administered intracerebroventricularly.

The present invention further relates to the use of the modified AAV vector according to the present invention, for the manufacture of a medicament for the prevention or treatment of a CNS disease,
wherein said modified AAV vector comprises at least one surface-bound saccharide,
wherein said modified AAV vector is to be administered intracerebrally, and
wherein said modified AAV vector is not to be administered intracerebroventricularly.

The present invention also relates to a method of preventing and/or treating a CNS disease in a subject in need thereof, comprising administering the modified AAV vector according to the present invention to said subject,
wherein said modified AAV vector comprises at least one surface-bound saccharide,
wherein said modified AAV vector is administered intracerebrally, and
wherein said modified AAV vector is not administered intracerebroventricularly.

As used herein, the terms "prevent", "preventing" and "prevention" refer to prophylactic and preventative measures, wherein the object is to reduce the chances that a subject will develop a given disease over a given period of time. Such a reduction may be reflected, e.g., in a delayed onset of at least one symptom of the CNS disease in the subject.

As used herein, the terms "treating" or "treatment" or "alleviation" refer to therapeutic treatment, excluding prophylactic or preventative measures; wherein the object is to slow down (lessen) a given disease. Those in need of treatment include those already with the disease as well those suspected to have the disease. A subject is successfully "treated" for a given disease if, after receiving a therapeutic amount of the modified AAV vector according to the present invention, said subject shows observable and/or measurable reduction in or absence of one or more of the following: one or more of the symptoms associated with the CNS disease; reduced morbidity and mortality; and/or improvement in quality of life issues. The above parameters for assessing successful treatment and improvement in the CNS disease are readily measurable by routine procedures familiar to a physician.

According to these embodiments, the modified AAV vector according to the present invention comprises at least one transgene.

The term "transgene", as used herein, refers to a polynucleotide that is introduced into a cell and is capable of being transcribed into RNA and optionally, translated and/or expressed under appropriate conditions. In one aspect, it confers a desired property to a cell into which it was introduced, or otherwise leads to a desired therapeutic or prophylactic outcome. In another aspect, the transgene may be incorporated, either entirely or partially, in the host cell's genome, such as, e.g., via corrective gene editing using a CRISPR/Cas-based method, TALEN-based method, ZFN-based method or the like, in presence of appropriate means. In still another aspect, it may be transcribed into a molecule that mediates RNA interference (i.e., gene silencing), such as into a miRNA, siRNA, shRNA, piRNA or the like.

In one embodiment, the at least one transgene comprises a cDNA encoding a protein or a fragment thereof.

As used herein, the term "cDNA" refers to complementary DNA and corresponds to a DNA molecule, usually synthesized from a single-stranded RNA (such as, e.g., a messenger RNA [mRNA] or a microRNA [miRNA] template in a reaction catalyzed by a reverse transcriptase. In particular, when a cDNA is obtained from reverse transcription of a mRNA, it does not comprise an entire gene coding from a protein, but only the coding sequence of said protein (i.e., exons without introns).

In particular, a fragment of a cDNA can comprise a part of said cDNA encoding the N-terminal part or the C-terminal part of a protein. Such fragment could be useful, e.g., in the case of large cDNAs which cannot be carried by a single AAV vector and would thus require the use of, e.g., dual AAV vectors.

Alternatively, a fragment of a cDNA can comprise a part of said cDNA encoding a functional and/or structural portion of a protein.

In some embodiments, a fragment of a cDNA can comprise a sequence encoding a functional and/or structural portion of an RNA molecule. In some embodiments, such an RNA molecule may be a ribosomal RNA, transfer RNA, small nuclear RNA, small nucleolar RNA, micro RNA, long non-coding RNA, short interfering RNA, guide RNA, and/or any functional RNA species.

In one embodiment, the cDNA is from a gene selected from the group comprising or consisting of 3R tau, 4R tau, AARS, ABCD1, ACOX1, ADGRV1, ADRA2B, AGA, AGER, ALDH7A1, ALG13, ALS2, ANG, ANXA11, APP, ARHGEF9, ARSA, ARSB, ARV1, ASAH1, ASPA, ATN1, ATP10A, ATP13A2, ATXN1, ATXN2, ATXN3, BAX, BCL-2, BDNF, BICD2, C9orf72, CACNA1A, CACNA1H, CACNB4, CASR, CCNF, CDKL5, CERS1, CFAP410, CHCHD10, CHD2, CHMP2B, CHRNA2, CHRNA4, CHRNA7, CHRNB2, CLCN2a, CLN1, CLN2, CLN3, CLN5, CLN6, CLN8, CNTN2, CPA6, CSTB, CTNS, CTSA, CTSD, DAO, DCTN1, DEPDC5, DMD, DNAJB2, DNM1, DOCK7, DRD2, DYNC1H1, EEF1A2, EFHC1, EGLN1, EPHA4, EPM2A, ERBB4, FGF12, FIG. 4, FRRS1L, FTL, FUCA1, FUS, FAXN, GAA, GABRA, GABRB1, GABRB3, GABRD, GABRG2, GAL, GALC, GALNS, GBA, GFAP, GLA, GLB1, GLE1, GLT8D1, GNAO1, GNS, GOSR2, GPR98, GRIA1, GRIA2, GRIK1, GRIN1, GRIN2A, GRIN2B, GRIN2D, GSTM1, GUF1, GUSB, HCN1, HGSNAT, HNRNPA1, HTT, HYAL1, IDS, IDUA, IGHMBP2, IL-1, IT15, ITPA, JPH3, KCNA2, KCNB1, KCNC1, KCNMA1, KCNQ2, KCNQ3, KCNT1, KCTD7, LAL, LAMP2, LGI1, LMNB2, LRRK2, MAN2B1, MAN2B2, MAN2C1, MANBA, MATR3, MBD5, MFSD8, NAGA, NAGLU, NECAP1, NEFH, NEK1, NEU1, NHLRC1, NPC1, NPC2, NR4A2, NTRK2, OCA2, OPTN, PARK2, PARK7, PCDH19, PEX1, PEX2, PEX3, PEX5, PEX6, PEX10, PEX11B, PEX12, PEX13, PEX14, PEX16, PEX19, PEX26, PFN1, PINK1, PLCB1, PNPO, PON1, PON2, PON3, PPARGC1A, PRDM8, PRICKLE1, PRKN, PRNP, PRPH, PRRT2, PSAP, S106β, SCARB2, SCN1A, SCN1B, SCN2A, SCN8A, SCN9A, SCN9Ab, SETX, SGSH, SIGMAR1, SK, SKP1, SLC1A1, SLC1A2, SLC2A1, SLC6A, SLC9A6, SLC12A5, SLC13A5, SLC25A12, SLC25A22, SLCA17A5, SMN1, SMPD1, SNCA, SNRPN, SOD1, SPG11, SPTAN1, SQSTM1, ST3GAL3, ST3GAL5, STX1B, STXBP1, SYP, SYT1, SZT2, TAF5, TARDBP, TBC1D24, TBCE, TBK1, TBP, TITF-1, TREM2, UBA5, UBE1, UBE3A, UBQLN2, UCH-L1, UNC13A, VAPB, VCP, VPS35, WWOX, and XBP1.

In one embodiment, the at least one transgene is under the control of at least one element which enhances the transgene target specificity and/or expression.

Examples of elements which enhance the transgene target specificity and/or expression include, but are not limited to, promoters, post-transcriptional regulatory elements (PREs), polyadenylation (poly A) signal sequences and upstream enhancers (USEs), CMV enhancers and introns.

In one embodiment, the at least one transgene is under the control of at least one promoter.

A person skilled in the art may recognize that expression of transgenes in a target cell may require a specific promoter, including, but not limited to, a promoter that is species-specific, inducible, tissue-specific, or cell cycle-specific.

In one embodiment, the promoter is a promoter having a tropism for the cell being targeted.

In one embodiment, the promoter drives expression of the transgene for a period of time in targeted tissues.

Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years.

In one embodiment, the promoter is a weak promoter for sustained expression of the transgene.

Promoters may be naturally occurring or non-naturally occurring. Non-limiting examples of promoters include, but are not limited to, viral promoters, plant promoters and mammalian promoters. In one embodiment, the promoter may be a human promoter.

In one embodiment, the promoter may be truncated or mutated.

Promoters which drive or promote expression in most tissues include, but are not limited to, human elongation factor 1a-subunit (EF1a), cytomegalovirus (CMV) immediate-early enhancer and/or promoter, chicken β-actin (CBA) and its derivative CAG, β-glucuronidase (GUSB), and ubiquitin C (UBC).

Tissue- or cell-specific expression elements can be used to restrict expression to certain cell types, such as CNS promoters which can be used to restrict expression to neurons, subtypes of neurons, or glial cells such as astrocytes or oligodendrocytes.

Suitable examples of tissue- or cell-specific expression elements for neurons include, but are not limited to, neuron-specific enolase (NSE) promoter, platelet-derived growth factor (PDGF) promoter, platelet-derived growth factor B-chain (PDGF-β) promoter, synapsin (Syn) promoter, methyl-CpG binding protein 2 (MeCP2) promoter, $Ca^{2+}$/calmodulin-dependent protein kinase II (CaMKII) promoter, metabotropic glutamate receptor 2 (mGluR2) promoter, neurofilament light (NFL) promoter, neurofilament heavy (NFH) promoter, β-globin minigene ηβ2 promoter, preproenkephalin (PPE) promoter, enkephalin (Enk) promoter and excitatory amino acid transporter 2 (EAAT2) promoter.

Suitable examples of tissue- or cell-specific expression elements for astrocytes include, but are not limited to, glial fibrillary acidic protein (GFAP) promoter and EAAT2 promoter.

Suitable examples of tissue- or cell-specific expression elements for oligodendrocytes include, but are not limited to, myelin basic protein (MBP) promoter.

In one embodiment, the promoter is a ubiquitous promoter.

Suitable examples of ubiquitous promoters include, but are not limited to, CMV, CBA (including its derivatives CAG, CBh, and the like), EF-1a, PGK, UBC, GUSB (hGBp), and UCOE.

In one embodiment, the promoter is not tissue- or cell-specific.

In one embodiment, the promoter is an engineered promoter.

In one embodiment, the promoter is a promoter from a naturally-expressed protein.

In a preferred embodiment, the promoter is a CAG promoter (CMV immediate early enhancer and chicken β-actin promoter).

In one embodiment, the CNS disease is a CNS infectious disease, a CNS degenerative disease, a CNS auto-immune disease, a CNS tumor disease, a cerebrovascular disease, a CNS injury or a CNS structural defect.

In one embodiment, the CNS disease is selected from the group comprising or consisting of acid lipase disease, acid maltase deficiency, acid storage disease, acquired epileptiform aphasia, acute disseminated encephalomyelitis, attention deficit hyperactivity disorder (ADHD), Adie's pupil, Adie's syndrome, adrenoleukodystrophy, agnosia, Aicardi syndrome, Aicardi-Goutieres syndrome disorder, Alexander disease, Alpers' disease, alternating hemiplegia, Alzheimer's disease, amyotrophic lateral sclerosis (ALS), anencephaly, aneurysm, Angelman syndrome, angiomatosis, anoxia, antiphospholipid syndrome, aphasia, apraxia, arachnoiditis, Arnold-Chiari malformation, aromatic L-amino acid decarboxylase deficiency (AADC deficiency), aspartylglucosaminuria, Asperger syndrome, ataxia, ataxia telangiectasia (Louis-Bar syndrome), ataxias and cerebellar or spinocerebellar degeneration, attention deficit-hyperactivity disorder, autism, autonomic dysfunction, Barth syndrome, Batten disease, Becker's myotonia, Behcet's disease, Bell's palsy, Bernhardt-Roth syndrome, Binswanger's disease, Bloch-Sulzberger syndrome, Bradbury-Eggleston syndrome, Brown-Sequard syndrome, bulbospinal muscular atrophy, CADASIL, Canavan's disease, causalgia, cavernomas, cavernous angioma, central cervical cord syndrome, central cord syndrome, central pontine myelinolysis, ceramidase deficiency, cerebellar degeneration, cerebellar hypoplasia, cerebral beriberi, cerebral gigantism, cerebral palsy, cerebro-oculo-facio-skeletal syndrome (COFS), cholesterol ester storage disease, chorea, choreoacanthocytosis, chronic inflammatory demyelinating polyneuropathy (CIDP), chronic orthostatic intolerance, chronic pain, Cockayne syndrome type II, Coffin-Lowry syndrome, colpocephaly, congenital myasthenia, corticobasal degeneration, cranial arteritis, cree encephalitis, Creutzfeldt-Jakob disease, Cushing's syndrome, cystinosis, cytomegalic inclusion body disease, dancing eyes-dancing feet syndrome, Dandy-Walker syndrome, Danon disease, Dawson disease, De Morsier's syndrome, Dejerine-Klumpke palsy, dementia, dentate cerebellar ataxia, dentatorubral atrophy, dermatomyositis, developmental dyspraxia, Devic's syndrome, diffuse sclerosis, dysautonomia, dysgraphia, dyslexia, dysphagia, dyspraxia, dyssynergia cerebellaris myoclonica, dyssynergia cerebellaris progressiva, epilepsy (such as, e.g., Amish infantile epilepsy syndrome [AIES], benign familial infantile seizures [BFIS], benign familial neonatal seizures [BFNS], childhood absence epilepsy [CAE], childhood-onset epileptic encephalopathy [COEE], Dravet syndrome [DS], early infantile epileptic encephalopathy [EIEE], familial adult myoclonic epilepsy [FAME], familial febrile seizures [FFS], familial focal epilepsy with variable foci [FFEVF], familial infantile myoclonic epilepsy [FIME], familial temporal lobe epilepsy [FTLE], focal epilepsy and speech disorder [FESD] with or without mental retardation, generalized epilepsy and paroxysmal dyskinesia [GEPD], generalized epilepsy with febrile seizures plus [GEFS+], idiopathic generalized epilepsy [IGE], juvenile absence epilepsy [JAE], juvenile myoclonic epilepsy [JME], myoclonic-atonic epilepsy [MAE], nocturnal frontal lobe epilepsy [NFLE], progressive myoclonic epilepsy [PME], pyridoxamine 5'-phosphate oxidase deficiency [PNPOD], pyridoxine-dependent epilepsy [EPD] and severe myoclonic epilepsy of infancy [SMEI]), Fabry disease, Fahr's syndrome, familial dysautonomia, familial hemangioma, familial idiopathic basal ganglia calcification, familial periodic paralyses, familial spastic paralysis, Farber's disease, fibromuscular dysplasia, Fisher syndrome, floppy infant syndrome, Friedreich's ataxia, frontotemporal dementia, fucosidosis, galactosialidosis, Gaucher disease, generalized gangliosidosis, Gerstmann's syndrome, Gerstmann-Straussler-Scheinker disease, giant axonal neuropathy, giant cell arteritis, giant cell inclusion disease, globoid cell leukodystrophy, glossopharyngeal neuralgia, glycogen storage disease, GM1 gangliosidosis, GM2 gangliosidosis (Tay-Sachs disease), Guillain-Barre syndrome, Hallervorden-Spatz disease, hemicrania continua, hemiplegia alterans, hereditary spastic paraplegia, heredopathia atactica polyneuritiformis, Holmes-Adie syndrome, holoprosencephaly, Hughes syndrome, Huntington's disease, hydranencephaly, hydromyelia, hypercortisolism, immune-mediated encephalomyelitis, inclusion body myositis, incontinentia pigmenti, infantile hypotonia, infantile neuroaxonal dystrophy, iniencephaly, Isaac's syndrome, Joubert syndrome, Kearns-Sayre syndrome, Kennedy's disease, Kinsbourne syndrome, Kleine-Levin syndrome, Klippel-Feil syndrome, Klippel-Trenaunay syndrome (KTS), Kliiver-Bucy syndrome, Korsakoff's amnesic syndrome, Krabbe disease, Kugelberg-Welander disease, Lambert-Eaton myasthenic syndrome, Landau-Kleffner syndrome, lateral femoral cutaneous nerve entrapment, lateral medullary syndrome, Leigh's disease, Lennox-Gastaut syndrome, Lesch-Nyhan syndrome, Levine-Critchley syndrome, Lewy body dementia, lipoid proteinosis, lissencephaly, locked-in syndrome, Lou Gehrig's disease, lupus, Lyme disease, Machado-Joseph disease, macrencephaly, alpha-mannosidosis, beta-mannosidosis, Melkersson-Rosenthal syndrome, Menkes disease, meralgia paresthetica, metachromatic leukodystrophy, microcephaly, Miller Fisher syndrome, Moebius syndrome, mucopolysaccharidosis type I-H (Hurler syndrome), mucopolysaccharidosis type I-H/S (Hurler-Scheie syndrome), mucopolysaccharidosis type IS (Scheie syndrome), mucopolysaccharidosis type II (Hunter syndrome), mucopolysaccharidosis type III-A (Sanfilippo syndrome A), mucopolysaccharidosis type III-B (Sanfilippo syndrome B), mucopolysaccharidosis type III-C(Sanfilippo syndrome C), mucopolysaccharidosis type III-D (Sanfilippo syndrome D), mucopolysaccharidosis type IV-B (Morquio syndrome B), mucopolysaccharidosis type VI (Maroteaux-Lamy syndrome), mucopolysaccharidosis type VII (Sly syndrome), mucopolysaccharidosis type IX (Natowicz syndrome), multiple sclerosis, muscular dystrophy, myasthenia gravis, myelinoclastic diffuse sclerosis, narcolepsy, neuroacanthocytosis, neurofibromatosis, neuroleptic malignant syndrome, neurosarcoidosis, Niemann-Pick disease, Ohtahara syndrome, olivopontocerebellar atrophy, opsoclonus myoclonus, O'Sullivan-McLeod syndrome, pantothenate kinase-associated neurodegeneration, paraneoplastic syndromes, paresthesia, Parkinson's disease, paroxysmal choreoathetosis, paroxysmal hemicrania, Parry-Romberg syndrome, Pelizaeus-Merzbacher disease, Pena Shokeir II syndrome, periventricular leukomalacia, phytanic acid storage disease, Pick's disease, piriformis syndrome, polymyositis, Pompe disease, post-polio syndrome, posterior cortical atrophy, primary dentatum atrophy, primary lateral sclerosis, primary progressive aphasia, prion diseases, progressive hemifacial atrophy, progressive locomotor ataxia, progressive multifocal leukoencephalopathy, progressive sclerosing poliodystrophy, progressive supranuclear palsy, prosopagnosia, Ramsay Hunt syndrome I, Ramsay Hunt syndrome II, Rasmussen's encephalitis, Refsum disease, Rett syndrome, Reye's syndrome, Riley-Day syndrome, Sandhoff disease, Schilder's disease, Seitelberger disease, Shy-Drager syndrome, Sjogren's syndrome, spasticity, spina bifida, spinal muscular atrophy, spinocerebellar ataxia, spinocerebellar atrophy, spinocerebellar degeneration, Steele-Richardson-Olszewski syndrome, striatonigral degeneration, Sturge-Weber syndrome, tardive dyskinesia, tauopathy, Tay-Sachs disease, thoracic outlet syndrome, thyrotoxic myopathy, tic douloureux, Todd's paralysis, trigeminal neuralgia, tropical spastic paraparesis, Troyer syndrome, vascular dementia, Von Economo's disease, Von Hippel-Lindau disease (VHL), Von Recklinghausen's disease, Wallenberg's syndrome, Werdnig-Hoffman disease, Wernicke-Korsakoff syndrome, West syndrome, Whipple's disease, Williams syndrome, Wilson disease, Wolman's disease, X-linked spinal and bulbar muscular atrophy, Zellweger syndrome, multiple sclerosis atrophy, Lewis body dementia (LBD), and Angelman syndrome.

As shown in the Examples, the inventors have shown that the modified adeno-associated virus (AAV) vectors of the invention are capable of effectively transducing certain areas of the brain, including the striatum, the thalamus, the substantia nigra, the parietal cortices, the hippocampus and/or the globus pallidus. Thus, the modified adeno-associated virus (AAV) vectors of the invention are of great interest for targeting the striatum, the thalamus, the substantia nigra, the parietal cortices, the hippocampus and the globus pallidus, and/or for treating diseases affecting the striatum, the thalamus, the substantia nigra, the parietal cortices, the hippocampus and the globus pallidus.

For instance, diseases affecting the striatum, the substantia nigra, the thalamus, the substantia nigra, the globus pallidus, the parietal cortices, and/or the hippocampus include, but are not limited to, Huntington's disease, Parkinson's disease, multiple sclerosis atrophy, Lewis Body Dementia (LBD), progressive supranuclear palsy and Angelman syndrome. In some embodiments, the CNS disease is selected from the group consisting of Huntington's disease, Parkinson's disease, multiple sclerosis atrophy, Lewis body dementia (LBD), progressive supranuclear palsy, frontotemporal dementia and Angelman syndrome.

The inventors have shown that the modified adeno-associated virus (AAV) vectors of the invention are capable of effectively transducing neurons.

Thus, in an embodiment, the CNS disease is a neurological disease or a disease affecting neurons.

The inventors have also shown that the modified adeno-associated virus (AAV) vectors of the invention are capable of effectively transducing neurons involved in the control of motor function. Thus, in an embodiment, the CNS disease is a motor neuron disease or syndrome.

Non-limiting examples of motor neuron diseases or syndrome include, but are not limited to, movement disorders, such as hypokinetic movement disorders and hyperkinetic movement disorders.

Non-limiting examples of hypokinetic movement disorders include, but are not limited to, Parkinson's disease (primary or idiopathic Parkinsonism), secondary Parkinsonism, Parkinson plus syndromes, Hallevorden-Spatz disease, progressive supranuclear ophthalmoplegia and striatonigral deneneration.

Non-limiting examples of hyperkinetic movement disorders include, but are not limited to, dystonia, drug induced dystonia, idiopathic familial dystonia, idiopathic nonfamilial dystonia, spasmodic torticollis, ideopathic orofacial dystonia, blepharospasm, extrapyramidal movement disorders, tremor, essential tremor, drug induced tremor, myoclonus, opsoclonus, chorea, drug induced chorea, rheumatic chorea (Sydenham's chorea), Huntington's chorea, ballismus, hemiballismus, athetosis, dyskinesia, tardive dyskinesia, tic disorders, Tourette's syndrome, drug-induced tics and tics of organic origin, stereotypic movement disorder, paroxysmal nocturnal limb movement, painful legs (or arms), moving toes (or fingers) syndrome, sporadic restless leg syndrome, familial restless leg syndrome, stiff-person syndrome, abnormal head movements, cramp, spasm and fasciculation.

In one embodiment, the CNS disease is Alzheimer's disease and the at least one transgene comprises a cDNA of a gene selected from the group comprising or consisting of 3R tau, 4R tau, AGER, APP, BAX, BCL-2, CHRNA7, DRD2, GFAP, GRIA1, GRIA2, GRIK1, GRIN1, IL-1, SLC1A1, SYP and SYT1.

In one embodiment, the CNS disease is Parkinson's disease and the at least one transgene comprises a cDNA of a gene selected from the group comprising or consisting of ATP13A2, BDNF, EGLN1, GBA, GSTM1, LRRK2, NR4A2, NTRK2, PARK2, PARK7, PINK1, PRKN, S106β, SKP1, SNCA, VPS35 and UCH-L1.

In one embodiment, the CNS disease is Huntington's disease and the at least one transgene comprises a cDNA of a gene selected from the group comprising or consisting of ATN1, ATXN1, ATXN2, ATXN3, FTL, HTT, IT15, JPH3, PRNP, SLC2A3, TBP, TITF-1 and XBP1.

In one embodiment, the CNS disease is Friedreich's ataxia and the at least one transgene comprises the cDNA of the FXN gene.

In one embodiment, the CNS disease is Canavan's Disease and the at least one transgene comprises the cDNA of the ASPA gene.

In one embodiment, the CNS disease is muscular dystrophy and the at least one transgene comprises the cDNA of the DMD gene.

In one embodiment, the CNS disease is spinal muscular atrophy and the at least one transgene comprises a cDNA of a gene selected from the group comprising or consisting of BICD2, CHCHD10, DNAJB2, DYNC1H1, IGHMBP2, SIGMAR1, SMN1, TBCE, VAPB and UBE1.

In one embodiment, the CNS disease is amyotrophic lateral sclerosis (ALS) and the at least one transgene comprises a cDNA of a gene selected from the group comprising or consisting of ALS2, ANG, ANXA11, ATXN2, C9orf72, CHMP2B, CFAP410, CHCHD10, CCNF, DAO, DCTN1, EPHA4, ERBB4, FIG4, FUS, GLE, GLT8D1, HNRNPA1, MATR3, NEFH, NEK1, OPTN, PFN1, PON1, PON2, PON3, PPARGC1A, PRPH, SETX, SIGMAR1, SMN1, SOD1, SPG11, SQSTM1, TAF15, TARDBP, TBK1, TREM2, UBQLN2, UNC13A, VAPB and VCP.

In one embodiment, the CNS disease is alpha-mannosidosis and the at least one transgene comprises a cDNA of a gene selected from the group comprising or consisting of MAN2B1, MAN2B2 and MAN2C1.

In one embodiment, the CNS disease is aspartylglucosaminuria and the at least one transgene comprises the cDNA of the AGA gene.

In one embodiment, the CNS disease is Batten disease and the at least one transgene comprises a cDNA of a gene selected from the group comprising or consisting of CLN1, CLN2, CLN3, CLN5, CLN6, CLN8, CTSD and MFSD8.

In one embodiment, the CNS disease is beta-mannosidosis and the at least one transgene comprises the cDNA of the MANBA gene.

In one embodiment, the CNS disease is cystinosis and the at least one transgene comprises the cDNA of the CTNS gene.

In one embodiment, the CNS disease is Danon disease and the at least one transgene comprises the cDNA of the LAMP2 gene.

In one embodiment, the CNS disease is Fabry disease and the at least one transgene comprises the cDNA of the GLA gene.

In one embodiment, the CNS disease is Farber disease and the at least one transgene comprises the cDNA of the ASAH1 gene.

In one embodiment, the CNS disease is fucosidosis and the at least one transgene comprises the cDNA of the FUCA1 gene.

In one embodiment, the CNS disease is galactosialidosis and the at least one transgene comprises the cDNA of the CTSA gene.

In one embodiment, the CNS disease is Gaucher disease and the at least one transgene comprises the cDNA of the GBA gene.

In one embodiment, the CNS disease is Krabbe disease and the at least one transgene comprises a cDNA of a gene selected from the group comprising or consisting of GALC and PSAP.

In one embodiment, the CNS disease is metachromic leukodystrophy and the at least one transgene comprises the cDNA of the ARSA gene.

In one embodiment, the CNS disease is a mucopolysaccharidosis (such as any of Hurler syndrome, Hurler-Scheie syndrome, Scheie syndrome, Hunter syndrome, Sanfilippo syndrome A, B, C or D, Morquio syndrome B, Maroteaux-Lamy syndrome, Sly syndrome or Natowicz syndrome) and the at least one transgene comprises a cDNA of a gene selected from the group comprising or consisting of ARSB, GAA, GALNS, GLB1, GNS, GUSB, HGSNAT, HYAL1, IDS, IDUA, LAL, NAGA, NAGLU, NEU1, NPC1, NPC2, SGSH, SLCA17A5 and SMPD1.

In one embodiment, the CNS disease is spinocerebellar ataxia and the at least one transgene comprises a cDNA of a gene selected from the group comprising or consisting of ATXN1, ATXN2 and ATN3.

In one embodiment, the CNS disease is adrenoleukodystrophy and the at least one transgene comprises a cDNA of a gene selected from the group comprising or consisting of ABCD1, ACOX1, PEX1, PEX2, PEX3, PEX5, PEX6, PEX10, PEX11B, PEX12, PEX13, PEX14, PEX16, PEX19 and PEX26.

In one embodiment, the CNS disease is Angelman syndrome and the at least one transgene comprises a cDNA of a gene selected from the group comprising or consisting of ATP10A, MBD5, OCA2, SLC9A6, SNRPN and UBE3A.

In one embodiment, the CNS disease is epilepsy and the at least one transgene comprises a cDNA of a gene selected from the group comprising or consisting of AARS, ADGRV1, ADRA2B, ALDH7A, ALG13, ARHGEF9, ARV1, CACNA1A, CACNA1H, CACNB4, CASR, CDKL5, CERS1, CHD2, CHRNA2, CHRNA4, CHRNB2, CLCN2a, CNTN2, CPA6, CSTB, DEPDC5, DNM1, DOCK7, EEF1A2, EFHC1, EPM2A, FGF12, FRRS1L, GABRA1, GABRB1, GABRB3, GABRD, GABRG2, GAL, GNAO1, GOSR2, GPR98, GRIN2A, GRIN2B, GRIN2D, GUF1, HCN1, ITPA, KCNA2, KCNB1, KCNC1, KCNMA1, KCNQ2, KCNQ3, KCNT1, KCTD7, LGI1, LMNB2, NECAP1, NHLRC1, PCDH19, PLCB1, PNPO, PRDM8, PRICKLE1, PRRT2, SCARB2, SCN1A, SCN1B, SCN2A, SCN8A, SCN9A, SCN9Ab, SIK1, SLC12A5, SLC13A5, SLC1A2, SLC25A12, SLC25A22, SLC2A1, SLC6A, SPTAN1, ST3GAL3, ST3GAL5, STX1B, STXBP1, SZT2, TBC1D24, UBA5, and WWOX.

One skilled in the art will recognize that a gene may have multiple transcriptional and/or translational isoforms, and that a transgene comprising a cDNA of a gene described herein encompasses the potential use of transcriptional variants and/or splice variants of a target gene.

In one embodiment, the modified AAV vectors according to the present invention is to be administered directly to the CNS.

By "administered directly to the CNS", it is meant administered intraspinally or intracerebrally.

In one embodiment, the modified AAV vectors according to the present invention may be administered by intraspinal and/or intracerebral administration.

In one embodiment, the modified AAV vector according to the present invention is to be administrated intraspinally.

In one embodiment, intraspinal administration comprises or consists of intrathecal and epidural administration.

In one embodiment, intraspinal administration comprises or consists of intrathecal administration.

In one embodiment, the modified AAV vector according to the present invention is to be administrated intracerebrally.

In one embodiment, intracerebral administration is at a site selected from the group comprising or consisting of: striatum (such as, e.g., putamen, caudate nucleus, nucleus accumbens, olfactory tubercle, external globus pallidus and/or internal globus pallidus), thalamus, hypothalamus, epithalamus, subthalamus, parenchyma, cerebrum, medulla, deep cerebellar nuclei (such as, e.g., substantia nigra, dentate, emboliform, globose and/or fastigii nucleus), cerebrospinal fluid (CSF), meninges, dura mater, arachnoid mater, pia mater, subarachnoid cisterns (such as, e.g., cisterna magna, pontine cistern, interpeduncular cistern, chiasmatic cistern, cistern of lateral cerebral fossa, superior cistern and/or cistern of lamina terminalis), subarachnoid space, cortex, septum, pons, and cerebellum.

In one embodiment, the modified AAV vector according to the present invention is to be administrated intrastriatally (i.e., in the striatum, such as, e.g., in the putamen, caudate nucleus, nucleus accumbens, olfactory tubercle, external globus pallidus and/or internal globus pallidus), intrathalamically (i.e., in the thalamus), intracisternally (i.e., in the subarachnoid cisterns, such as, e.g., in the cisterna magna, pontine cistern, interpeduncular cistern, chiasmatic cistern, cistern of lateral cerebral fossa, superior cistern and/or cistern of lamina terminalis; preferably in the cisterna magna).

In one embodiment, the modified AAV vector according to the present invention is to be administered intraparenchymally.

In one embodiment, the modified AAV vector according to the present invention is to be administrated intrastriatally, intrathalamically, intracisternally or intrathecally.

In one embodiment, the modified AAV vector according to the present invention is to be administrated intrastriatally or intrathalamically.

In one embodiment, the modified AAV vector according to the present invention is not to be administered intracerebroventricularly (i.e., not in the ventricular system, such as, e.g., not in the right lateral ventricle, left lateral ventricle, third ventricle and/or fourth ventricle).

It is to be understood that the terms "administration" or "administered", as used herein, are meant to encompass injections, infusions, and any other means of administration known by the one skilled in the art.

In one embodiment, the modified AAV vector according to the present invention is to be administered to the subject in need thereof in a therapeutically effective amount.

In one embodiment, the modified AAV vector according to the present invention is to be administered at a dose ranging from about $10^8$ viral genomes (vg) to about $10^{15}$ vg, such as from about $10^8$ vg to about $10^{14}$ vg, from about $10^8$ vg to about $10^{13}$ vg, from about $10^8$ vg to about $10^{12}$ vg, from about $10^8$ vg to about $10^{11}$ vg, from about $10^8$ vg to about $10^{10}$ vg, from about $10^8$ vg to about $10^9$ vg, from about $10^9$ vg to about $10^{15}$ vg, from about $10^9$ vg to about $10^{14}$ vg, from about $10^9$ vg to about $10^{13}$ vg, from about $10^9$ vg to about $10^{12}$ vg, from about $10^9$ vg to about $10^{11}$ vg, from about $10^9$ vg to about $10^{10}$ vg, from about $10^{10}$ vg to about $10^{15}$ vg, from about $10^{10}$ vg to about $10^{14}$ vg, from about $10^{10}$ vg to about $10^{13}$ vg, from about $10^{10}$ vg to about $10^{12}$ vg, from about $10^{10}$ vg to about $10^{11}$ vg, from about $10^{11}$ vg to about $10^{15}$ vg, from about $10^{11}$ vg to about $10^{14}$ vg, from about $10^{11}$ vg to about $10^{13}$ vg, from about $10^{11}$ vg to about $10^{12}$ vg, from about $10^{12}$ vg to about $10^{15}$ vg, from about $10^{12}$ vg to about $10^{14}$ vg, from about $10^{12}$ vg to about $10^{13}$ vg, from about $10^{13}$ vg to about $10^{15}$ vg.

The term "vector genome", abbreviated as "vg", refers to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques (e.g., a transgene). In some embodiments, the nucleic acid titer of a viral vector may be measured in terms of vg/mL. Methods suitable for measuring this titer are known in the art, and include, e.g., quantitative PCR.

As used herein, the term "about", when set in front of a numerical value, means that said numerical value is approximate and small variations would not significantly affect the practice of the disclosed embodiments. Such small variations are, e.g., of ±1%, +2%, +3%, 4%,±5% 6%,±7% 8%,±9% 10% or more.

In one embodiment, the modified AAV vector according to the present invention is to be administered at a dose of about $1\times10^8$ vg±$0.5\times10^8$, about $2\times10^8$ vg±$0.5\times10^8$, about $2.75\times10^8$ vg±$0.5\times10^8$, about $3\times10^8$ vg±$0.5\times10^8$, about $4\times10^8$ vg±$0.5\times10^8$, about $5\times10^8$ vg±$0.5\times10^8$, about $6\times10^8$ vg±$0.5\times10^8$, about $7\times10^8$ vg±$0.5\times10^8$, about $8\times10^8$ vg±$0.5\times10^8$, about $9\times10^8$ vg±$0.5\times10^8$, about $1\times10^9$ vg±$0.5\times10^9$, about $2\times10^9$ vg±$0.5\times10^9$, about $3\times10^9$ vg±$0.5\times10^9$, about $4\times10^9$ vg±$0.5\times10^9$, about $5\times10^9$ vg±$0.5\times10^9$, about $6\times10^9$ vg±$0.5\times10^9$, about $7\times10^9$ vg±$0.5\times10^9$, about $8\times10^9$ vg±$0.5\times10^9$, about $9\times10^9$ vg±$0.5\times10^9$, about $1\times10^{10}$ vg±$0.5\times10^{10}$, about $2\times10^{10}$ vg±$0.5\times10^{10}$, about $3\times10^{10}$ vg±$0.5\times10^{10}$, about $4\times10^{10}$ vg±$0.5\times10^{10}$, about $5\times10^{10}$ vg±$0.5\times10^{10}$, about $6\times10^{10}$ vg±$0.5\times10^{10}$, about $7\times10^{10}$ vg±$0.5\times10^{10}$, about $8\times10^{10}$ vg±$0.5\times10^{10}$, about $9\times10^{10}$ vg±$0.5\times10^{10}$, about $1\times10^{11}$ vg±$0.5\times10^{11}$, about $2\times10^{11}$ vg±$0.5\times10^{11}$, about $3\times10^{11}$ vg±$0.5\times10^{11}$, about $4\times10^{11}$ vg±$0.5\times10^{11}$, about $5\times10^{11}$ vg±$0.5\times10^{11}$, about $6\times10^{11}$ vg±$0.5\times10^{11}$, about $7\times10^{11}$ vg±$0.5\times10^{11}$, about $8\times10^{11}$ vg±$0.5\times10^{11}$, about $9\times10^{11}$ vg±$0.5\times10^{11}$, about $1\times10^{12}$ vg±$0.5\times10^{12}$, about $2\times10^{12}$ vg±$0.5\times10^{12}$, about $3\times10^{12}$ vg±$0.5\times10^{12}$, about $4\times10^{12}$ vg±$0.5\times10^{12}$, about $5\times10^{12}$ vg±$0.5\times10^{12}$, about $6\times10^{12}$ vg±$0.5\times10^{12}$, about $7\times10^{12}$ vg±$0.5\times10^{12}$, about $8\times10^{12}$ vg±$0.5\times10^{12}$, about $9\times10^{12}$ vg±$0.5\times10^{12}$, about $1\times10^{13}$ vg±$0.5\times10^{13}$, about $2\times10^{13}$ vg±$0.5\times10^{13}$, about $3\times10^{13}$ vg±$0.5\times10^{13}$, about $4\times10^{13}$ vg±$0.5\times10^{13}$, about $5\times10^{13}$ vg±$0.5\times10^{13}$, about $6\times10^{13}$ vg±$0.5\times10^{13}$, about $7\times10^{13}$ vg±$0.5\times10^{13}$, about $8\times10^{13}$ vg±$0.5\times10^{13}$, about $9\times10^{13}$ vg±$0.5\times10^{13}$, about $1\times10^{14}$ vg±$0.5\times10^{14}$, about $2\times10^{14}$ vg±$0.5\times10^{14}$, about $3\times10^{14}$ vg±$0.5\times10^{14}$, about $4\times10^{14}$ vg±$0.5\times10^{14}$, about $5\times10^{14}$ vg±$0.5\times10^{14}$, about $6\times10^{14}$ vg±$0.5\times10^{14}$, about $7\times10^{14}$ vg±$0.5\times10^{14}$, about $8\times10^{14}$ vg±$0.5\times10^{14}$, about $9\times10^{14}$ vg±$0.5\times10^{14}$, about $1\times10^{15}$ vg±$0.5\times10^{15}$, about $2\times10^{15}$ vg±$0.5\times10^{15}$, about $3\times10^{15}$ vg±$0.5\times10^{15}$, about $4\times10^{15}$ vg±$0.5\times10^{15}$, about $5\times10^{15}$ vg±$0.5\times10^{15}$, about $6\times10^{15}$ vg±$0.5\times10^{15}$, about $7\times10^{15}$ vg±$0.5\times10^{15}$, about $8\times10^{15}$ vg±$0.5\times10^{15}$, about $9\times10^{15}$ vg±$0.5\times10^{15}$.

In one embodiment, the modified AAV vector according to the present invention is to be administered at a dose of about $1\times10^6$ vg/kg±$0.5\times10^6$, about $2\times10^6$ vg/kg±$0.5\times10^6$, about $3\times10^6$ vg/kg±$0.5\times10^6$, about $4\times10^6$ vg/kg±$0.5\times10^6$, about $5\times10^6$ vg/kg±$0.5\times10^6$, about $6\times10^6$ vg/kg±$0.5\times10^6$, about $7\times10^6$ vg/kg±$0.5\times10^6$, about $8\times10^6$ vg/kg±$0.5\times10^6$, about $9\times10^6$ vg/kg±$0.5\times10^6$, about $1\times10^7$ vg/kg±$0.5\times10^7$, about $2\times10^7$ vg/kg±$0.5\times10^7$, about $3\times10^7$ vg/kg±$0.5\times10^7$, about $4\times10^7$ vg/kg±$0.5\times10^7$, about $5\times10^7$ vg/kg±$0.5\times10^7$, about $6\times10^7$ vg/kg±$0.5\times10^7$, about $7\times10^7$ vg/kg±$0.5\times10^7$, about $8\times10^7$ vg/kg±$0.5\times10^7$, about $9\times10^7$ vg/kg±$0.5\times10^7$, about $1\times10^8$ vg/kg±$0.5\times10^8$, about $2\times10^8$ vg/kg±$0.5\times10^8$, about $3\times10^8$ vg/kg±$0.5\times10^8$, about $4\times10^8$ vg/kg±$0.5\times10^8$, about $5\times10^8$ vg/kg±$0.5\times10^8$, about $6\times10^8$ vg/kg±$0.5\times10^8$, about $7\times10^8$ vg/kg±$0.5\times10^8$, about $8\times10^8$ vg/kg±$0.5\times10^8$, about $9\times10^8$ vg/kg±$0.5\times10^8$, about $1\times10^9$ vg/kg±$0.5\times10^9$, about $2\times10^9$ vg/kg±$0.5\times10^9$, about $3\times10^9$ vg/kg±$0.5\times10^9$, about $4\times10^9$ vg/kg±$0.5\times10^9$, about $5\times10^9$ vg/kg±$0.5\times10^9$, about $6\times10^9$ vg/kg±$0.5\times10^9$, about $7\times10^9$ vg/kg±$0.5\times10^9$, about $8\times10^9$ vg/kg±$0.5\times10^9$, about $9\times10^9$ vg/kg±$0.5\times10^9$, about $1\times10^{10}$ vg/kg±$0.5\times10^{10}$, about $2\times10^{10}$ vg/kg±$0.5\times10^{10}$, about $3\times10^{10}$ vg/kg±$0.5\times10^{10}$, about $4\times10^{10}$ vg/kg±$0.5\times10^{10}$, about $5\times10^{10}$ vg/kg±$0.5\times10^{10}$, about 6×10^{10} vg/kg±0.5×10^{10}, about 7×10^{10} vg/kg±0.5×10^{10}, about 8×10^{10} vg/kg±0.5×10^{10}, about 9×10^{10} vg/kg±0.5×10^{10}, about 1×10^{11} vg/kg±0.5×10^{11}, about 2×10^{11} vg/kg±0.5×10^{11}, about 3×10^{11} vg/kg±0.5×10^{11}, about 4×10^{11} vg/kg±0.5×10^{11}, about 5×10^{11} vg/kg±0.5×10^{11}, about 6×10^{11} vg/kg±0.5×10^{11}, about 7×10^{11} vg/kg±0.5×10^{11}, about 8×10^{11} vg/kg±0.5×10^{11}, about 9×10^{11} vg/kg±0.5×10^{11}, about 1×10^{12} vg/kg±0.5×10^{12}, about 2×10^{12} vg/kg±0.5×10^{12}, about 3×10^{12} vg/kg±0.5×10^{12}, about 4×10^{12} vg/kg±0.5×10^{12}, about 5×10^{12} vg/kg±0.5×10^{12}, about 6×10^{12} vg/kg±0.5×10^{12}, about 7×10^{12} vg/kg±0.5×10^{12}, about 8×10^{12} vg/kg±0.5×10^{12}, about 9×10^{12} vg/kg±0.5×10^{12}, about 1×10^{13} vg/kg±0.5×10^{13}, about 2×10^{13} vg/kg±0.5×10^{13}, about 3×10^{13} vg/kg±0.5×10^{13}, about 4×10^{13} vg/kg±0.5×10^{13}, about 5×10^{13} vg/kg±0.5×10^{13}, about 6×10^{13} vg/kg±0.5×10^{13}, about 7×10^{13} vg/kg±0.5×10^{13}, about 8×10^{13} vg/kg±0.5×10^{13}, about 9×10^{13} vg/kg±0.5×10^{13}, about 1×10^{14} vg/kg±0.5×10^{14}.

The dose of modified AAV vectors required to achieve a desired effect or a therapeutic effect will vary based on several factors including, but not limited to, the specific route of administration, the level of gene, RNA or protein expression required to achieve a therapeutic effect, the specific disease being treated, and the stability of the gene, RNA or protein product. The one skilled in the art can readily determine a dose range to treat a subject having a particular disease based on the aforementioned factors, as well as other factors that are well known in the art.

The volume of modified AAV vectors administered to a subject will also depend, among other things, on the size of the subject, the dose of the modified AAV vector, and the route of administration. For example, for intracerebral administration, a volume ranging from about 1 μL to about 10 μL or from about 10 μL to about 100 μL or from about 100 μL to about 1000 μL or from about 1 mL to about 10 mL may be used.

In one embodiment, the volume of modified AAV vectors administered to a subject is of about 1 μL±0.5 μL, about 2 μL±0.5 μL, about 3 μL±0.5 μL, about 4 μL±0.5 μL, about 5 μL±0.5 μL, about 6 μL±0.5 μL, about 7 μL±0.5 μL, about 8 μL±0.5 μL, about 9 μL±0.5 μL, about 10 μL±0.5 μL, about 15 μL±5 μL, about 20 μL±5 μL, about 25 μL±5 μL, about 30 μL±5 μL, about 35 μL±5 μL, about 40 μL±5 μL, about 45 μL±5 μL, about 50 μL±5 μL, about 55 μL±5 μL, about 60 μL±5 μL, about 65 μL±5 μL, about 70 μL±5 μL, about 75 μL±5 μL, about 80 μL±5 μL, about 85 μL±5 μL, about 90 μL±5 μL, about 95 μL±5 μL, about 100 μL±5 μL, about 150 μL±50 μL, about 200 μL±50 μL, about 250 μL±50 μL, about 300 μL±50 μL, about 350 μL±50 μL, about 400 μL±50 μL, about 450 μL±50 μL, about 500 μL±50 μL, about 550 μL±50 μL, about 600 μL±50 μL, about 650 μL±50 μL, about 700 μL±50 μL, about 750 μL±50 μL, about 800 μL±50 μL, about 850 μL±50 μL, about 900 μL±50 μL, about 950 μL±50 μL, about 1000 μL±50 μL, about 1.5 mL±250 μL, about 2 mL±250 μL, about 2.5 mL±250 μL, about 3 mL±250 μL, about 3.5 mL±250 μL, about 4 mL±250 μL, about 4.5 mL±250 μL, about 5 mL±250 μL, about 5.5 mL±250 μL, about 6 mL±250 μL, about 6.5 mL±250 μL, about 7 mL±250 μL, about 7.5 mL±250 μL, about 8 mL±250 μL, about 8.5 mL±250 μL, about 9 mL±250 μL, about 9.5 mL±250 μL, about 10 mL±250 μL.

The rate of administration of modified AAV vectors administered to a subject will also depend, among other things, on the size of the subject, the dose of the modified AAV vector, the volume of the modified AAV vector, and the route of administration. For example, for intracerebral administration, a rate of administration ranging from about 0.1 μL/min to about 1 μL/min or from about 1 μL/min to about 5 μL/min or from about μL/min to about 10 μL/min may be used.

In one embodiment, the rate of administration of modified AAV vectors administered to a subject is of about 0.1 μL/min±0.05 μL/min, about 0.2 μL/min±0.05 μL/min, about 0.3 μL/min±0.05 μL/min, about 0.4 μL/min±0.05 μL/min, about 0.5 μL/min±0.05 μL/min, about 0.6 μL/min±0.05 μL/min, about 0.7 μL/min±0.05 μL/min, about 0.8 μL/min±0.05 μL/min, about 0.9 μL/min±0.05 μL/min, 1 μL/min±0.5 μL/min, about 2 μL/min±0.5 μL/min, about 3 μL/min±0.5 μL/min, about 4 μL/min±0.5 μL/min, about 5 μL/min±0.5 μL/min, about 6 μL/min±0.5 μL/min, about 7 μL/min±0.5 μL/min, about 8 μL/min±0.5 μL/min, about 9 μL/min±0.5 μL/min, about 10 μL/min±0.5 μL/min.

In one embodiment, the total dose or total volume of modified AAV vectors may be administered continuously (i.e., wherein the total dose or total volume of modified AAV vectors is injected in a single shot or infusion); or discontinuously (i.e., wherein fractions of the total dose or total volume of modified AAV vectors are injected with intermittent periods between each shot, preferably with short intermittent periods such as periods of time of 15 seconds, 30 seconds, 45 seconds, 1 minute, 2 minutes, 3 minutes, 4 minutes, or 5 minutes between each shot or infusion).

The present invention also relates to a modified adeno-associated virus (AAV) vector comprising at least one transgene.

In one embodiment, the modified AAV vector according to the present invention comprises at least one surface-bound saccharide or a derivative thereof, as described hereinabove.

In one embodiment, the at least one transgene comprises a cDNA encoding a protein or a fragment thereof.

In particular, a fragment of a cDNA can comprise a part of said cDNA encoding the N-terminal part or the C-terminal part of a protein. Such fragment could be useful, e.g., in the case of large cDNAs which cannot be carried by a single AAV vector and would thus require the use of dual AAV vectors.

Alternatively, a fragment of a cDNA can comprise a part of said cDNA encoding a functional and/or structural portion of a protein.

In one embodiment, the cDNA is from a gene selected from the group comprising or consisting of 3R tau, 4R tau, AARS, ABCD1, ACOX, ADGRV1, ADRA2B, AGA, AGER, ALDH7A1, ALG13, ALS2, ANG, ANXA1, APP, ARHGEF9, ARSA, ARSB, ARV1, ASAH1, ASPA, ATN1, ATP10A, ATP13A2, ATXN1, ATXN2, ATXN3, BAX, BCL-2, BDNF, BICD2, C9orf72, CACNA1A, CACNA1H, CACNB4, CASR, CCNF, CDKL5, CERS1, CFAP410, CHCHD10, CHD2, CHMP2B, CHRNA2, CHRNA4, CHRNA7, CHRNB2, CLCN2a, CLN1, CLN2, CLN3, CLN5, CLN6, CLN8, CNTN2, CPA6, CSTB, CTNS, CTSA, CTSD, DAO, DCTN1, DEPDC5, DMD, DNAJB2, DNM1, DOCK7, DRD2, DYNC1H1, EEF1A2, EFHC1, EGLN1, EPHA4, EPM2A, ERBB4, FGF12, FIG. 4, FRRS1L, FTL, FUCA1, FUS, FAXN, GAA, GABRA, GABRB1, GABRB3, GABRD, GABRG2, GAL, GALC, GALNS, GBA, GFAP, GLA, GLB1, GLE1, GLT8D1, GNAO1, GNS, GOSR2, GPR98, GRIA1, GRIA2, GRIK1, GRIN1, GRIN2A, GRIN2B, GRIN2D, GSTM1, GUF1, GUSB, HCN1, HGSNAT, HNRNPA1, HTT, HYAL1, IDS, IDUA, IGHMBP2, IL-1, IT15, ITPA, JPH3, KCNA2, KCNB1, KCNC1, KCNMA1, KCNQ2, KCNQ3, KCNT1, KCTD7, LAL, LAMP2, LGI1, LMNB2, LRRK2, MAN2B1, MAN2B2, MAN2C1, MANBA, MATR3, MBD5, MFSD8, NAGA, NAGLU, NECAP1, NEFH, NEK1, NEU1, NHLRC1, NPC1, NPC2, NR4A2, NTRK2, OCA2, OPTN, PARK2, PARK7, PCDH19, PEX1, PEX2, PEX3, PEX5, PEX6, PEX10, PEX11B, PEX12, PEX13, PEX14, PEX16, PEX19, PEX26, PFN1, PINK1, PLCB1, PNPO, PON1, PON2, PON3, PPARGC1A, PRDM8, PRICKLE1, PRKN, PRNP, PRPH, PRRT2, PSAP, S106β, SCARB2, SCN1A, SCN1B, SCN2A, SCN8A, SCN9A, SCN9Ab, SETX, SGSH, SIGMAR1, SIK1, SKP1, SLC1A1, SLC1A2, SLC2A1, SLC6A, SLC9A6, SLC12A5, SLC13A5, SLC25A12, SLC25A22, SLCA17A5, SMN1, SMPD1, SNCA, SNRPN, SOD1, SPG11, SPTAN1, SQSTM1, ST3GAL3, ST3GAL5, STX1B, STXBP1, SYP, SYT1, SZT2, TAF5, TARDBP, TBC1D24, TBCE, TBK1, TBP, TITF-1, TREM2, UBA5, UBE1, UBE3A, UBQLN2, UCH-L1, UNC13A, VAPB, VCP, VPS35, WWOX, and XBP1.

In one embodiment, the at least one transgene is under the control of at least one element which enhances the transgene target specificity and/or expression.

Examples of such elements which enhances the transgene target specificity and/or expression have been described hereinabove, and apply mutatis mutandis.

In one embodiment, the modified AAV vector comprising at least one transgene according to the present invention is part of a composition. The invention thus relates to a composition comprising the modified AAV vector comprising at least one transgene according to the present invention.

In one embodiment, the modified AAV vector comprising at least one transgene according to the present invention is part of a medicament. The invention thus relates to a medicament comprising the modified AAV vector comprising at least one transgene according to the present invention.

In one embodiment, the composition is a pharmaceutical composition and further comprises at least one pharmaceutically acceptable excipient, carrier, and/or preservative.

The invention thus relates to a pharmaceutical composition comprising the modified AAV vector comprising at least one transgene according to the present invention, and at least one pharmaceutically acceptable excipient, carrier, and/or preservative.

The term "pharmaceutically acceptable", when referring to excipients, carriers, and/or preservatives, is meant to define molecular entities and compositions that do not produce an allergic or similar untoward reaction when administered to a subject, preferably a human. For human administration, pharmaceutical compositions should meet sterility, pyrogenicity, and general safety and purity standards as required by regulatory offices, such as, for example, FDA Office or EMA.

Pharmaceutically acceptable excipients, carriers and preservatives that may be used in these compositions include, but are not limited to, ion exchangers, alumina, aluminum stearate, lecithin, proteins (such as, e.g., serum albumin, gelatin, immunoglobulins and the like), buffer substances (such as, e.g., phosphates, citrates or other organic acids, and the like), amino acids (such as, e.g., glycine, glutamine, asparagine, arginine, lysine and the like), antioxidants (such as, e.g., ascorbic acid and the like), chelating agents (such as, e.g., EDTA), sorbic acid, potassium sorbate, partial glyceride mixtures of saturated vegetable fatty acids, water, salts or electrolytes (such as, e.g., protamine sulfate, disodium hydrogen phosphate, potassium hydrogen phosphate, sodium chloride, zinc salts, colloidal silica, magnesium trisilicate and the like), hydrophilic polymers (such as, e.g., polyvinylpyrrolidone, polyethylene-polyoxypropylene block polymers and the like), cellulose-based substances (such as, e.g., sodium carboxymethylcellulose), polyacrylates, waxes, nonionic surfactants (such as, e.g., Tween, pluronics, polyethylene glycol and the like) and wool fat.

In one embodiment, the pharmaceutical composition according to the present invention comprise vehicles which are pharmaceutically acceptable for a formulation capable of being injected to a subject. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

In one embodiment, the pharmaceutical composition according to the present invention comprise one or more agents that promote the entry of the modified AAV vector described herein into a mammalian cell, such as, e.g., natural and/or synthetic polymers, such as poloxamer, chitosan, cyclodextrins, dendrimers, poly(lactic-co-glycolic acid) polymers, and the like.

The present invention also relates to kits and kits-of-parts, for:
  transducing a cell in the central nervous system (CNS) of a subject; and/or
  delivering a transgene to the central nervous system (CNS) of a subject; and/or
  preventing and/or treating a central nervous system (CNS) disease in a subject.

In one embodiment, the kits or kits-of-parts comprise the modified AAV vectors or the composition according to the present invention.

In one embodiment, the kits or kits-of-parts comprise a device for CNS delivery of the modified AAV vectors or the composition according to the present invention.

Devices for CNS delivery are known in the art and may employ a pump (e.g., an osmotic and/or infusion pump, as described below) and/or an injection device (e.g., a catheter, a cannula, a needle, a syringe, and the like).

Optionally, an imaging technique may be used to guide the injection device and/or monitor delivery of the composition. CNS delivery may include delivery by stereotaxic injection, or by convection enhanced delivery (CED). The injection device may be inserted into the CNS tissue in the subject. The one skilled in the art is able to determined suitable coordinates for positioning the injection device in the target CNS tissue. In one embodiment, positioning is accomplished through an anatomical map obtained, e.g., by CT and/or MRI imaging of the subject's brain to guide the injection device to the target CNS tissue.

In one embodiment, intraoperative magnetic resonance imaging (iMRI) and/or real-time imaging of the delivery may be performed. In one embodiment, the device is used to administer the modified AAV vectors as described herein. iMRI is known in the art as a technique for MRI-based imaging of a subject during surgery, which helps confirm a successful surgical procedure (e.g., to deliver the modified AAV vectors to the CNS) and reduces the risk of damaging other parts of the tissue. In one embodiment, a tracing agent (such as, e.g., an MRI contrast enhancing agent) may be co-delivered with the modified AAV vectors to provide for real-time monitoring of tissue distribution of the vectors. Use of a tracing agent may inform the cessation of delivery. Other tracing and imaging means known in the art may also be used to follow modified AAV vector distribution.

In one embodiment, the modified AAV vectors according to the present invention may be administered by standard stereotaxic injection using devices and methods known in the art for delivery of AAV vectors. Generally, these methods may use an injection device, a planning system for translating a region of the tissue targeted for delivery into a series of coordinates (e.g., parameters along the latero-lateral, dorso-ventral, and rostro-caudal axes), and a device for stereotaxic localization according to the planned coordinates (e.g., a stereotaxic device, optionally including the probe and a structure for fixing the head in place in alignment with the coordinate system). A non-limiting example of a system that may be useful for MRI-guided surgery and/or stereotaxic injection is the ClearPoint® system (MRI Interventions, Memphis, Tenn.).

Another exemplary and non-limiting method for delivering the modified AAV vectors according to the present invention to the CNS is convection enhanced delivery. As used herein, the term "convection enhanced delivery" or "CED" may refer to delivery of a therapeutic agent to the CNS by infusion at a rate in which hydrostatic pressure leads to convective distribution. Any suitable flow rate can be used such that the intracranial pressure is maintained at suitable levels so as not to injure the brain tissue. CED may be accomplished, for example, by using a suitable catheter or cannula (e.g., a step-design reflux-free cannula) through positioning the tip of the cannula at least in close proximity to the target CNS tissue (e.g., the tip is inserted into the CNS tissue). After the cannula is positioned, it is connected to a pump which delivers the therapeutic agent through the cannula tip to the target CNS tissue. A pressure gradient from the tip of the cannula may be maintained during infusion. In one embodiment, infusion may be monitored by a tracing agent detectable by an imaging method such as intraoperative MRI (iMRI) or another real-time MRI technique.

CED is based on pumping an infusate (e.g., the composition comprising the modified AAV vectors according to the present invention) into the CNS under pressure in which the hydrostatic pressure of the interstitial fluid is overcome. This brings the infusate into contact with the CNS perivasculature, which is utilized like a pump to distribute the infusate through convection and enhance the extent of its delivery.

In one embodiment, the kits further include instructions for CNS delivery of the modified AAV vectors or the composition according to the present invention. In one embodiment, the kits comprise instructions for preventing and/or treating a CNS disease as described herein, using the uses and methods described herein.

The kits described herein may further include other materials desirable from a commercial and user standpoint, including buffers, diluents, filters, needles, syringes, and package inserts with instructions for performing any methods described herein.

BRIEF DESCRIPTION OF THE DRAWINGS

FIG. 2 is a set of three immunohistochemistry photographs (in color), showing the GFP staining of mouse brain slices from the G1 [Vehicle], G2 [AAV2-GFP] and G3 [mannose AAV2-GFP] group, 48 days after intrastriatal injection.

FIG. 3 is a set of two graphs showing the statistical analyses of the volume of GFP transduction in the striatum (injection site) and substantia nigra in mouse brains from the G1 [Vehicle], G2 [wt AAV2], and G3 [man AA V2] group, 48 days after intrastriatal injection. Bars represent the group mean; dots represent the individual animal values. The data were analyzed with one-way ANOVA followed by Tukey's multiple comparisons. *$p<0.05$, *$p<0.001$, **$p<0.0001$ cf. group G1; and ##$p<0.01$, ####$p<0.0001$ cf. group G2.

FIG. 4 is a set of three immunohistochemistry photographs (in color), showing the GFP staining of mouse brain slices from the G4 [Vehicle], G5 [AAV2-GFP] and G6 [mannose AAV2-GFP] group, 48 days after intrathalamic injection.

FIG. 5 is a set of two graphs showing the statistical analyses of the volume of GFP transduction in the thalamus (injection site) and substantia nigra in mouse brains from the G4 [Vehicle], G5 [wt AAV2], and G6 [man AAV2] group, 48 days after intrathalamic injection. Bars represent the group mean; dots represent the individual animal values. The data were analyzed with one-way ANOVA followed by Tukey's multiple comparisons. $p<0.01$, **$p<0.0001$ cf. group G4; and ####$p<0.0001$ cf. group G5.

FIG. 6 is a set of three immunohistochemistry photographs (in color), showing the GFP staining of mouse brain slices from the G7 [Vehicle], G8 [AAV2-GFP] and G9 [mannose AAV2-GFP] group, 48 days after intracerebroventricular injection.

FIG. 9A: immunohistochemistry photograph (in color) of mouse thalamus slices from the G1 [Vehicle] group.

FIG. 9B: immunohistochemistry photograph (in color) of mouse thalamus slices from the G2 [mannose AAV2-GFP] group.

FIG. 9C: immunohistochemistry photograph (in color) of mouse thalamus slices from the G3 [AAV2-GFP] group.

FIG. 11C: immunohistochemistry photograph (in color) of mouse striatum slices from the G3 [mannose AAV2-GFP] group.

FIG. 11D: immunohistochemistry photograph (in color) of mouse striatum slices from the G4 [galactose AAV2-GFP] group.

FIG. 11E: immunohistochemistry photograph (in color) of mouse striatum slices from the G5 [N-acetyGlucosamine AAV2-GFP] group.

EXAMPLE 1: EVALUATION OF THE TRANSDUCTION CAPABILITY OF TWO AAV VECTORS IN MOUSE BRAIN

The objective of the study was to investigate the potential of two recombinant AAV (rAAV) vectors ("unmodified rAAV2" and "mannosylated rAAV2") to transduce large brain areas in mouse.

Materials

Animals

Twenty-four (24) male C57 BL/6 mice (*Mus musculus*), purchased from Janvier Labs.

Test Items

"Unmodified rAAV2", a recombinant AAV2 vector comprising an unmodified capsid carrying an eGFP cDNA under control of a CAG promoter.

Figure 1:
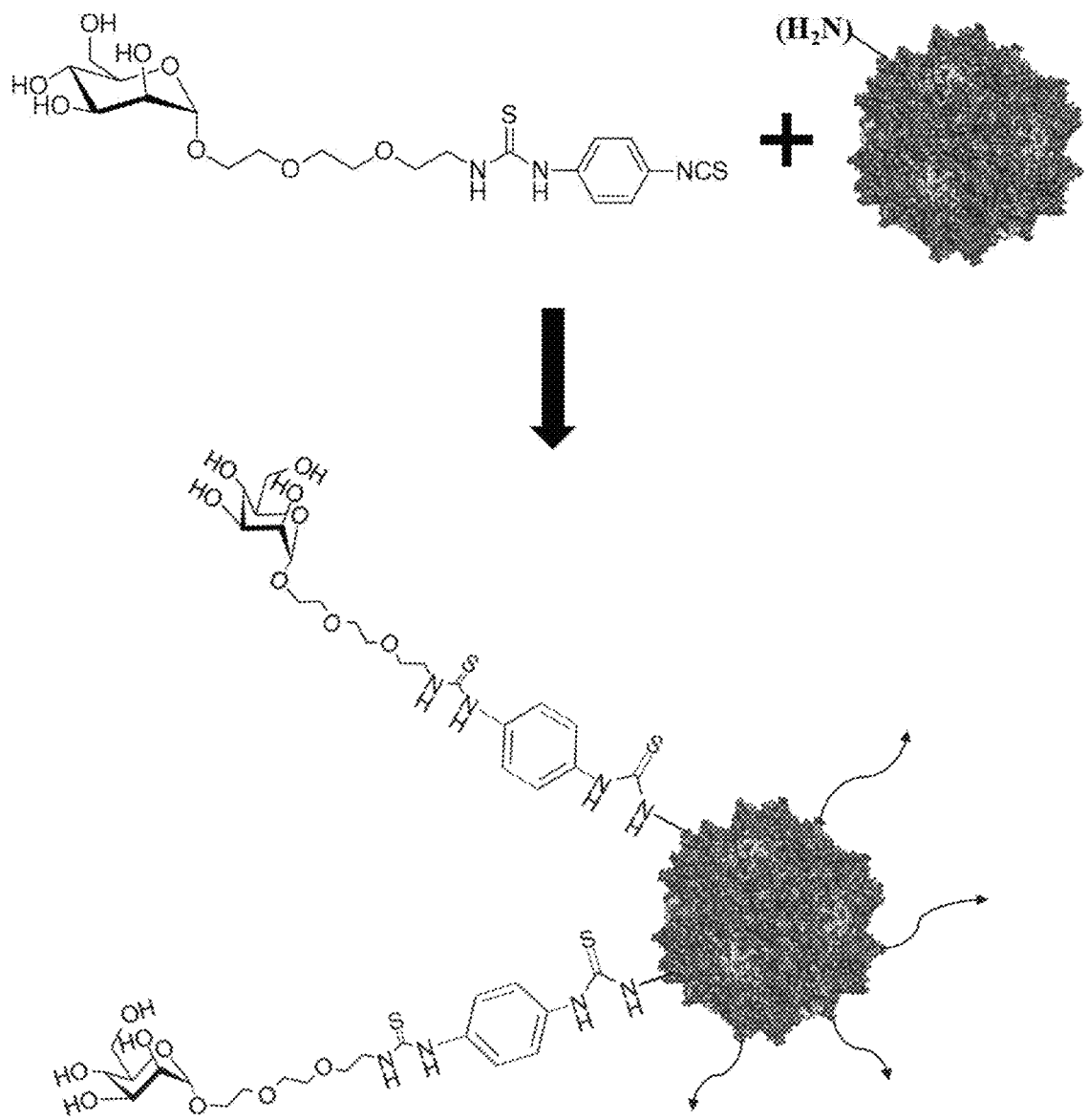
FIG. 1 is a schematic view of one suitable way to synthetize mannosylated rAAV2 vectors. ($H_2N$)— represents a surface-exposed primary amine reacting with the isothiocyanate (N=C=S) reactive group to couple the mannose moiety. For the purposes of this illustration, only two mannose residues are shown bound to the AAV capsid. Black arrows schematically indicate other mannose moieties.

"Mannosylated rAAV2", a recombinant AAV2 vector comprising a modified capsid with surface-bound mannose residues, and carrying an eGFP cDNA under control of a CAG promoter. Mannose residues were covalently bound to primary amines of lysine residues exposed at the surface of the AAV2 capsid. FIG. 1 provides a visual representation of mannosylated rAAV2.

"Vehicle", a lactate Ringer's solution (LRS), as negative control.

Methods

Test Items

Mannosylated rAAV2 was produced as previously described in International patent publication WO2017212019 and illustrated in FIG. 1. Briefly, unmodified rAAV2 were mixed in Tris buffer pH 9.3 with isothiocyanate-linker-mannose molecules, and incubated during 4 hours at 20° C. The mix was then dialyzed against buffered saline sterile solution (BSSS)+0.001% Pluronic® F68 remove free molecules that did not bind to the AAV capsid.

Study Design

Twenty-four (24) mice underwent stereotactic surgery and were injected unilaterally with the test items into the right striatum, the right thalamus or the right lateral ventricle.

The animals were randomly assigned to 9 groups, names G1 to G9, according to Table 1.

TABLE 1

Treatment schedule.

| Group | n | Treatment | Target |
|---|---|---|---|
| G1 | 2 | Vehicle | Right striatum |
| G2 | 3 | Unmodified rAAV2 | Right striatum |
| G3 | 3 | Mannosylated rAAV2 | Right striatum |
| G4 | 1* | Vehicle | Right thalamus |
| G5 | 3 | Unmodified rAAV2 | Right thalamus |
| G6 | 3 | Mannosylated rAAV2 | Right thalamus |
| G7 | 2 | Vehicle | Right lateral ventricle |
| G8 | 3 | Unmodified rAAV2 | Right lateral ventricle |
| G9 | 3 | Mannosylated rAAV2 | Right lateral ventricle |

*In group G4, one mouse was found dead before termination of the experiment.

Surgical Procedures

Buprenorphine (0.1 mg/kg; 10 mL/kg, s.c.) was given as an analgesic before and after surgery. The animal was placed in an anesthetic chamber supplied with a continuous flow of oxygen (1.5 L/min) and 3% isoflurane. Following loss of consciousness, the animal was placed in a stereotactic frame (Kopf) and its head was fixed into position using ear bars. The skin of the skull was incised.

Each mouse received unilateral injections (2 for striatum, 2 for thalamus, 1 for ventricle) of one of the test items using a glass pipette, at the coordinates described in Table 2. For an atlas of the mouse brain, see Paxinos & Franklin, 2019. The mouse brain in stereotaxic coordinates (5$^{th}$ ed.). San Diego, Calif.: Elsevier Science Publishing Co Inc.

TABLE 2

Injection coordinates.

| Target | AP (mm) | ML (mm) | DV (mm) | Volume/target (μL) | Titer/target (vg/mL) |
|---|---|---|---|---|---|
| Right striatum | +1.0 | 2.1 | −2.6 | 0.5 | $5.5 \times 10^{11}$ |
|  | +0.3 | 2.3 | −2.6 | 0.5 | $5.5 \times 10^{11}$ |
| Right thalamus | −1.8 | 1.8 | −3.4 | 0.5 | $5.5 \times 10^{11}$ |
|  | −2.5 | 1.8 | −3.4 | 0.5 | $5.5 \times 10^{11}$ |
| Right ventricle | −0.5 | 1.0 | −2.4 | 4 | $3.6 \times 10^{11}$ |

AP: anterior-posterior;
ML: medial-lateral;
DV: dorsal-ventral.

Animals were allowed to recover for 48 days before euthanasia was carried out.

Ex Vivo Analysis

Euthanasia and Tissue Processing

At the end of the in vivo phase, animals were euthanized and tissue were collected. Euthanasia was performed in accordance with accepted European Veterinary Medical Association guidelines.

At termination, the brain of each animal was quickly removed and fixed in paraformaldehyde (PFA; 4%). After 3 days, the tissues were cryoprotected in 20% sucrose solution (in 0.1 M PBS) at 4° C. overnight and then frozen.

The whole brain was cut into 50 m thick coronal sections using a cryostat. Free-floating sections were placed in PBS azide and stored at 4° C.

GFP Immunohistochemistry

Definition of the percentage of transduced brain volume in the regions of interest was made based upon GFP immunohistochemistry. One in every four sections was used for immunohistochemistry.

Tissue sections were taken from the refrigerator and left to adjust to room temperature. After thorough rinsing with PBS, endogenous peroxidase was inhibited with peroxidase-blocking solution (Dako, S2023) for 10 minutes.

After thorough rinsing with PBS, non-specific labelling was prevented by blocking antigenic sites with PBS containing 2% BSA, 0.3% Triton X-100 and 0.01% thimerosal for 30 minutes.

Sections were incubated overnight in primary antibody (rabbit anti-GFP, polyclonal antibody, Ab3080, Merck) diluted at 1/1000 in PBS containing 0.2% BSA, 0.3% Triton X-100 and 0.01% thimerosal.

After thorough rinsing with PBS, sections were incubated for 30 minutes with Dako Envision labelled polymer HRP anti-rabbit (Dako, K4011).

After thorough rinsing with PBS, revelation was obtained with Dako DAB. After approximately 30 seconds, revelation was stopped with several PBS washes.

Sections were then mounted onto slides and counterstained with a Nissl stain. The slides were digitized using a PannoramicScan II (3DHISTECH, Hungary) at a ×20 magnification with an extended mode in which 5-layer focus is automatically acquired and then flatten.

The striatum, the thalamus, and the substantia nigra were drawn using the MERCATOR software (Mercator, Explora Nova, La Rochelle, France) on 10, 10 and 6 sections, respectively.

Using the whole transduced area (with artifacts excluded), the surface of GFP staining was obtained using a threshold detection method. The volume was calculated using the formula $$V = \Sigma S t d$$

where "ΣS" is the sum of surface areas; "t" is the average section thickness; and "d" is the number of slices between two consecutives analyzed sections measured.

The percentage of transduced brain volume in the regions of interest was then calculated.

Data Analysis

A one-way ANOVA was performed to assess the difference between the treatment groups followed by Tukey's multiple comparison (Graphpad Prism version 8.0.2).

Results

Injection in the Striatum

Figures 2A, 2B:
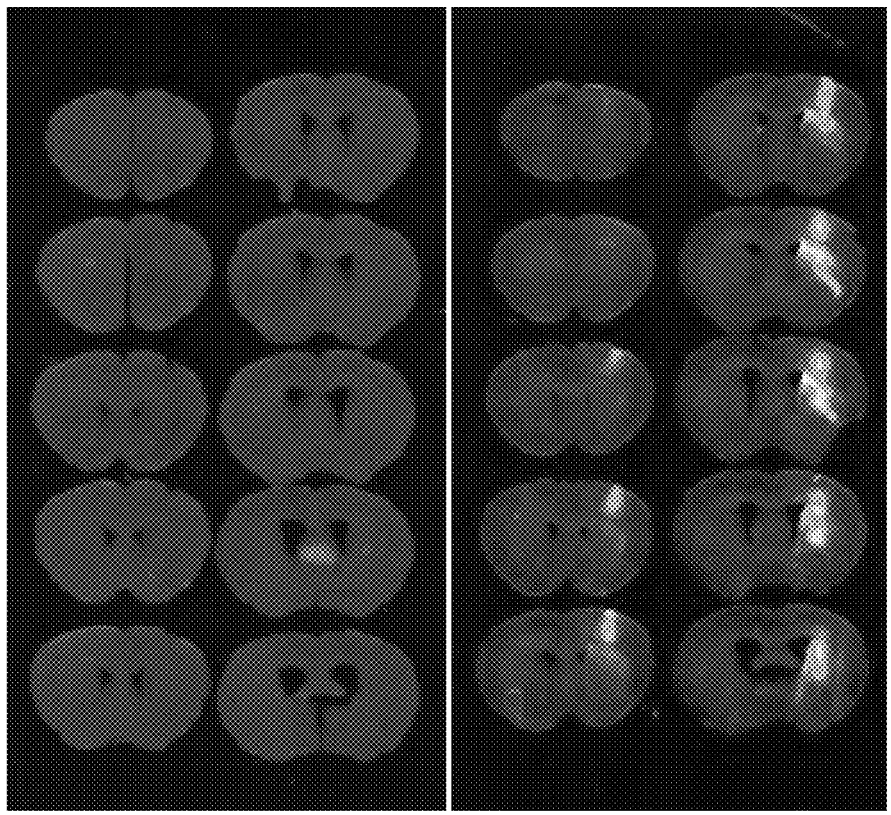
FIG. 2A: immunohistochemistry photograph (in color) of mouse brain slices from the G1 group.
FIG. 2B: immunohistochemistry photograph (in color) of mouse brain slices from the G2 group.
Figure 2C:
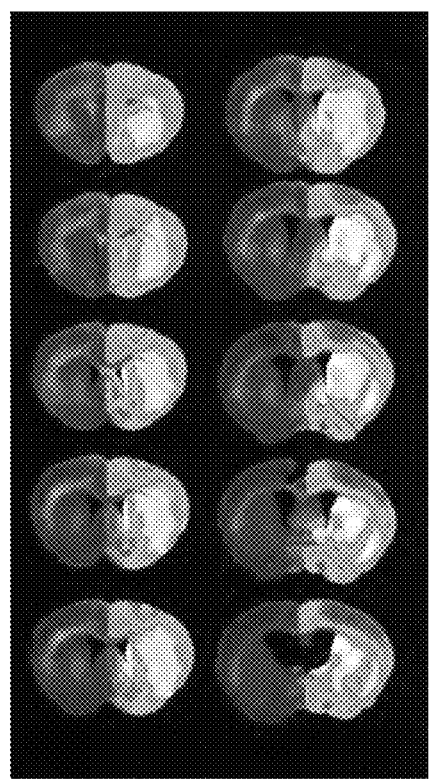
FIG. 2C: immunohistochemistry photograph (in color) of mouse brain slices from the G3 group.

Immunohistochemically stained brain slices of mouse from the G1, G2 and G3 group are shown in FIG. 2A, FIG. 2B and FIG. 2C, respectively. The percentage of GFP staining area is given in Table 3.

TABLE 3

GFP staining area after intrastriatal injection.

| Location | Group G1 | Group G2 | Group G3 |
|---|---|---|---|
| Striatum | 0% | 12.90% | 45.44% |
| Substantia nigra | 0% | 9.98% | 50.21% |

Figure 3A:
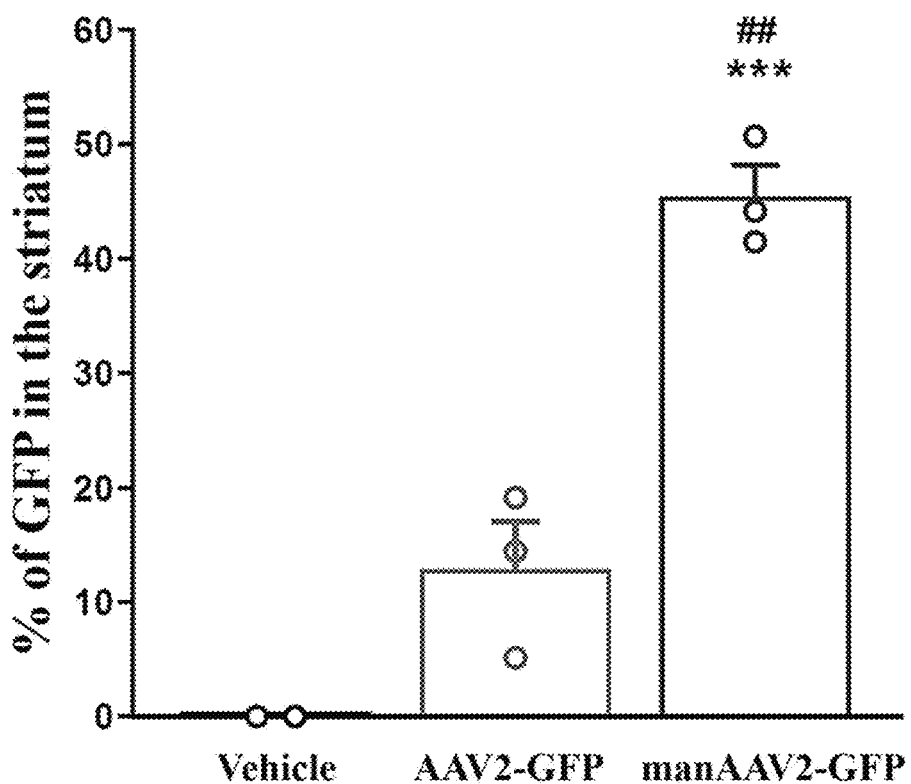
FIG. 3A: statistical analyses of the volume of GFP transduction in the striatum.
Figure 3B:
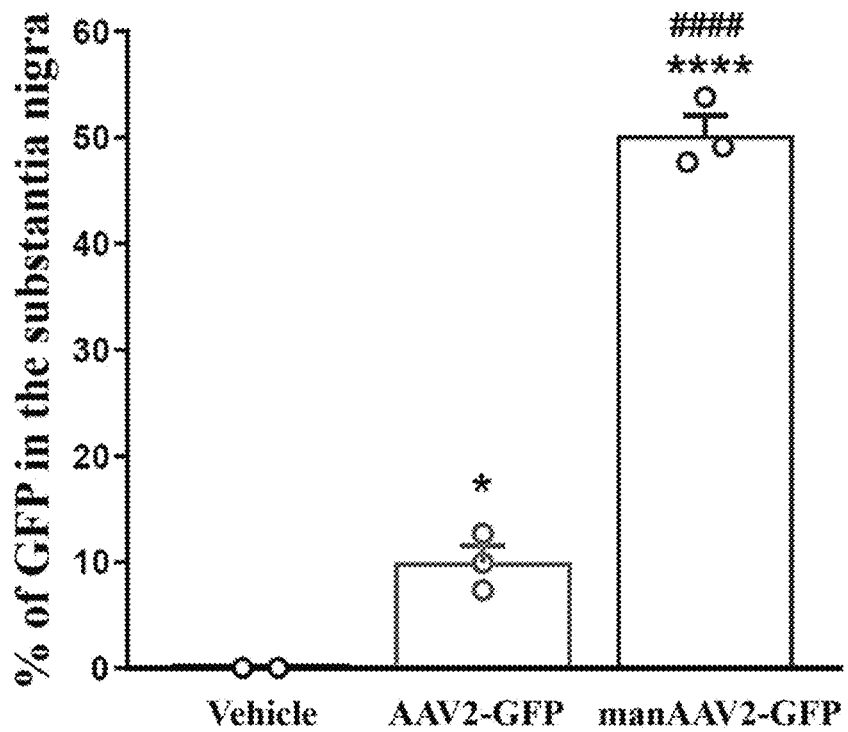
FIG. 3B: statistical analyses of the volume of GFP transduction in the substantia nigra.

Statistical analyses of the GFP transduction in the striatum (FIG. 3A) and substantia nigra (FIG. 3B), 48 days after intrastriatal injection, are summarized in Table 4.

TABLE 4

GFP transduction after intrastriatal injection.

| Location | One-way ANOVA | p value |
|---|---|---|
| Striatum | $F\ (2, 5) = 48.82$ | 0.0005 |
| Substantia nigra | $F\ (2, 5) = 271.9$ | <0.0001 |

The significant differences between treatment groups following Tukey's multiple comparison test for % of GFP transduction in the striatum are summarized in Table 5.

TABLE 5

Difference between treatment groups after intrastriatal injection.

| Tukey's multiple comparison | p value |
|---|---|
| G1 vs G3 | 0.0006 |
| G2 vs G3 | 0.0017 |

The significant differences between treatment groups following Tukey's multiple comparison test for % of GFP transduction in the substantia nigra are summarized in Table 6.

TABLE 6

Difference between treatment groups after intrastriatal injection.

| Tukey's multiple comparison | p value |
|---|---|
| G1 vs G2 | 0.0203 |
| G1 vs G3 | <0.0001 |
| G2 vs G3 | <0.0001 |

Injection in the Thalamus

Figures 4A, 4B:
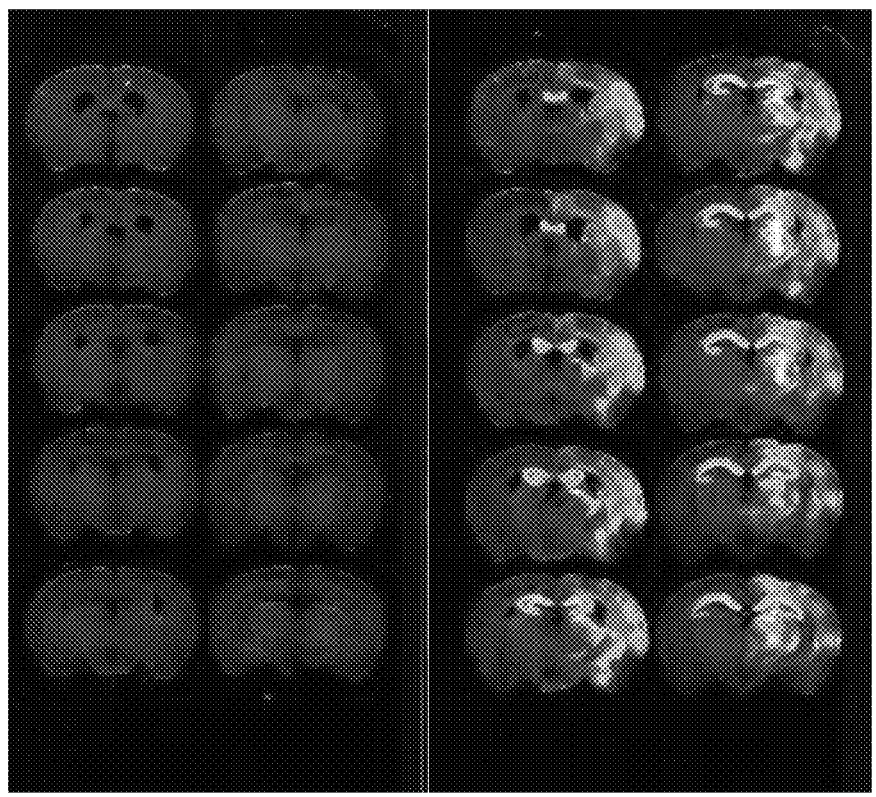
FIG. 4A: immunohistochemistry photograph (in color) of mouse brain slices from the G4 group.
FIG. 4B: immunohistochemistry photograph (in color) of mouse brain slices from the G5 group.
Figure 4C:
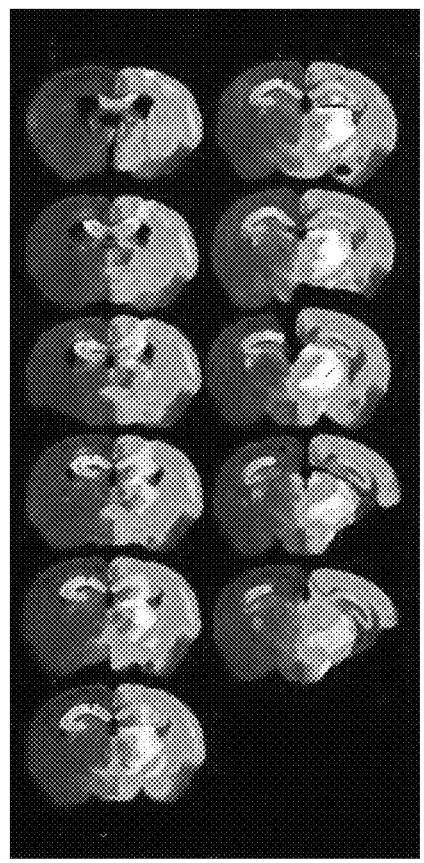
FIG. 4C: immunohistochemistry photograph (in color) of mouse brain slices from the G6 group.

Immunohistochemically stained brain slices of mouse from the G4, G5 and G6 group are shown in FIG. 4A, FIG. 4B and FIG. 4C, respectively. The percentage of GFP staining area is given in Table 7.

TABLE 7

GFP staining area after intrathalamic injection.

| Location | Group G4 | Group G5 | Group G6 |
|---|---|---|---|
| Thalamus | 0% | 8.67% | 37.85% |
| Substantia nigra | 0% | 0% | 1.67% |

Figure 5A:
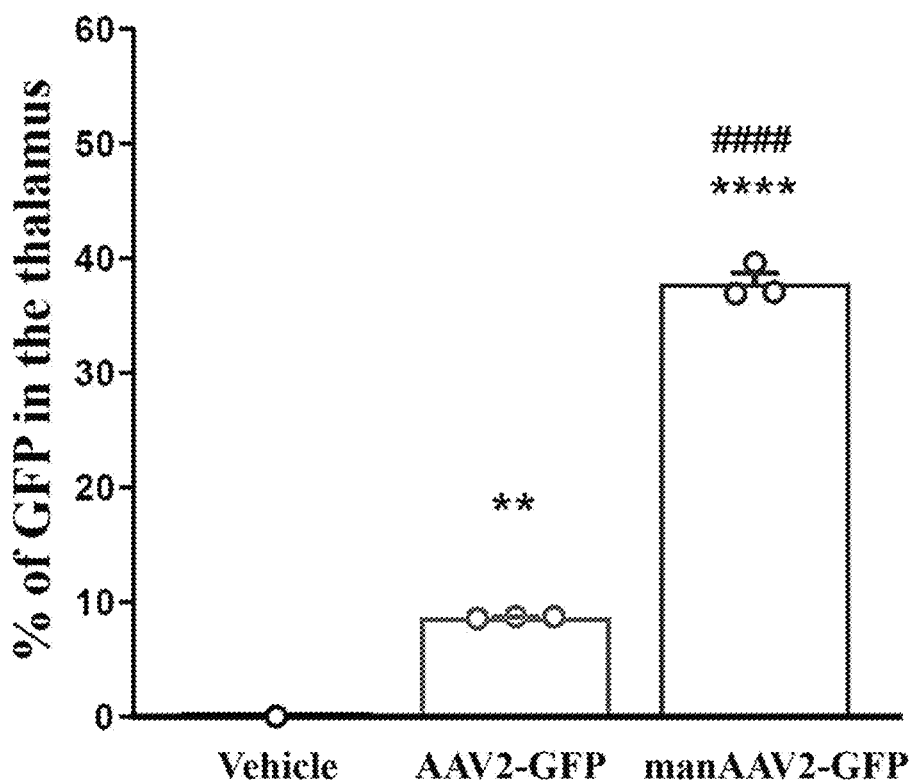
FIG. 5A: statistical analyses of the volume of GFP transduction in the thalamus.
Figure 5B:
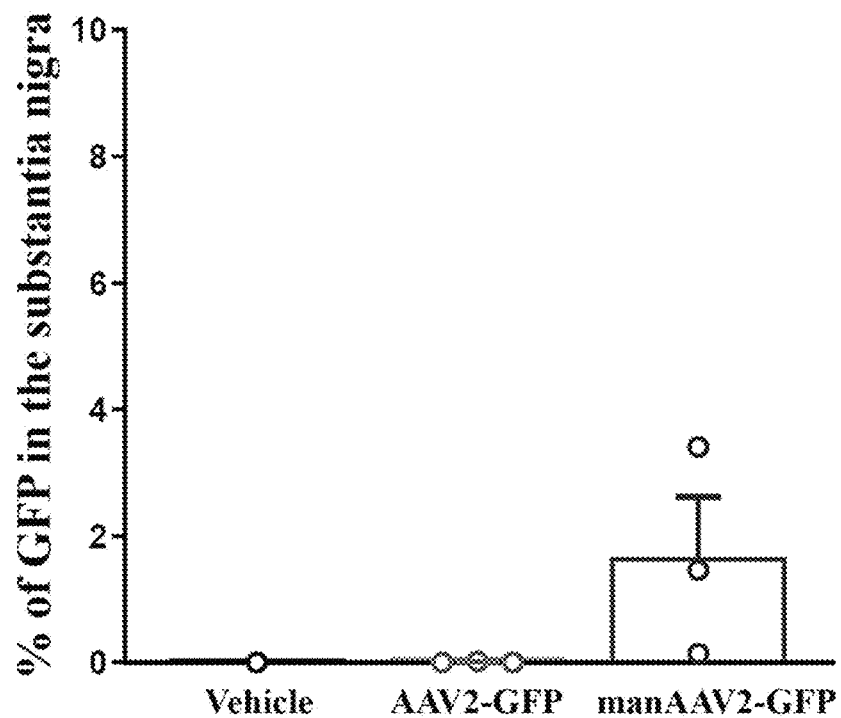
FIG. 5B: statistical analyses of the volume of GFP transduction in the substantia nigra.

Statistical analyses of the GFP transduction in the thalamus (FIG. 5A) and substantia nigra (FIG. 5B), 48 days after intrathalamic injection, are summarized in Table 8.

TABLE 8

GFP transduction after intrathalamic injection.

| Location | One-way ANOVA | p value |
|---|---|---|
| Thalamus | F (2, 4) = 744.4 | <0.0001 |
| Substantia nigra | F (2, 4) = 1.756 | 0.2835 |

The significant differences between treatment groups following Tukey's multiple comparison test for % of GFP transduction in the thalamus are summarized in Table 9.

TABLE 9

Difference between treatment groups after intrathalamic injection.

| Tukey's multiple comparison | p value |
|---|---|
| G4 vs G5 | 0.005 |
| G4 vs G6 | <0.0001 |
| G5 vs G6 | <0.0001 |

Injection in the Ventricle

Figures 6A, 6B:
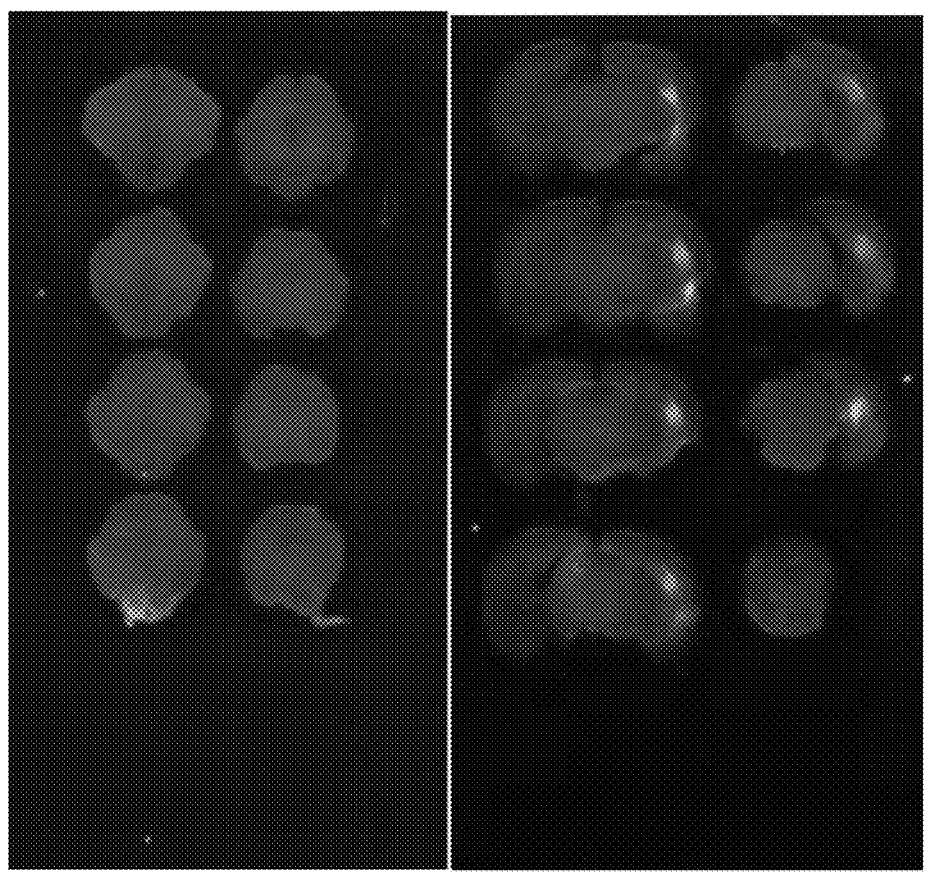
FIG. 6A: immunohistochemistry photograph (in color) of mouse brain slices from the G7 group.
FIG. 6B: immunohistochemistry photograph (in color) of mouse brain slices from the G8 group.
Figure 6C:
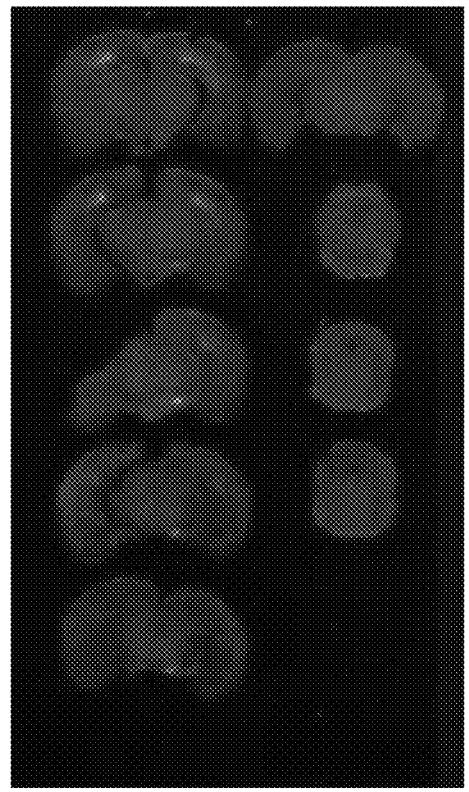
FIG. 6C: immunohistochemistry photograph (in color) of mouse brain slices from the G9 group.

Immunohistochemically stained brain slices of mouse from the G7, G8 and G9 group are shown in FIG. 6A, FIG. 6B and FIG. 6C, respectively. The percentage of GFP staining area is given in Table 10.

TABLE 10

GFP staining area after intrathalamic injection.

| Location | Group G7 | Group G8 | Group G9 |
|---|---|---|---|
| Substantia nigra | 0% | 0.01% | 0.22% |

Figure 7:
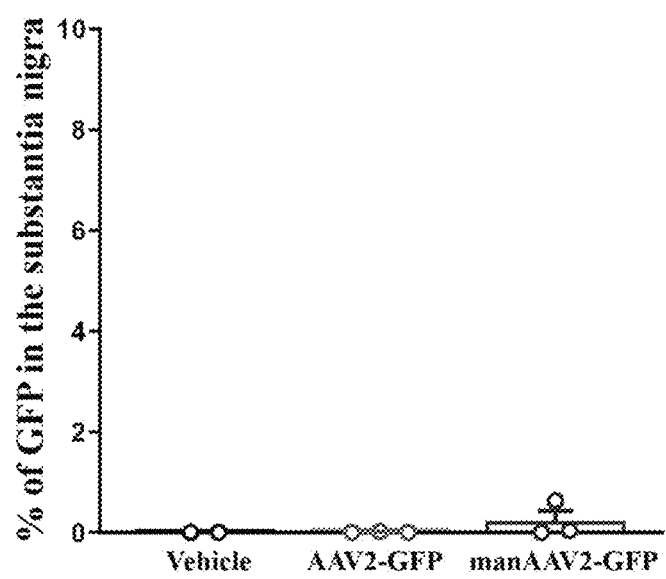
FIG. 7 is a graph showing the statistical analyses of the volume of GFP transduction in the substantia nigra (injection in the ventricle) in mouse brains from the G7 [Vehicle], G8 [AAV2-GFP], and G9 [mannose AAV2-GFP] group, 48 days after intracerebroventricular injection. Bars represent the group mean; dots represent the individual animal values. The data were analyzed with one-way ANOVA.

Statistical analyses of the GFP transduction in the substantia nigra (FIG. 7), 48 days after intracerebroventricular injection, are summarized in Table 11.

TABLE 11

GFP transduction after intracerebroventricular injection.

| Location | One-way ANOVA | p value |
|---|---|---|
| Substantia nigra | F (2, 5) = 0.9057 | 0.4617 |

No significant differences between treatment groups in the % of GFP transduction were observed.

Conclusion

The objective of the study was to investigate the potential of two AAV vectors ("unmodified rAAV2" and "mannosylated rAAV2") to transduce large brain areas in mouse.

Both AAV vectors drove the expression of GFP and the surface of the GFP staining in specific brain areas was used to assess the capability of each vector to transduce brain cells.

When the injection was made in the striatum, the percentage of GFP staining in the striatum was 12.90% for unmodified rAAV2 and 45.44% for mannosylated rAAV2; in the substantia nigra, it was 9.98% for unmodified rAAV2 and 50.21% for the mannosylated rAAV2.

When the injection was made in the thalamus, the percentage of GFP in the thalamus was 8.67% for the unmodified rAAV2 and 37.85% for the mannosylated rAAV2; in the substantia nigra, it was 0% for the unmodified rAAV2 and 1.67% for the mannosylated rAAV2.

When the injection was made in the ventricle, the percentage of GFP in the substantia nigra was of 0.01% for the unmodified rAAV2 and 0.22% for the mannosylated rAAV2.

The mannosylated rAAV2 achieved a larger coverage of expression than unmodified rAAV2, when administered in the brain parenchyma (striatum or thalamus). Anterograde as well as retrograde transportation of the mannosylated rAAV2 is observed.

Besides the actual measurements in dedicated brain areas, the general aspect is clearly in favor of mannosylated rAAV2 since a single administration in the brain parenchyma (striatum or thalamus) led to a whole hemisphere transduction. In particular, immunohistochemical analyses showed that GFP expression is also located in the cortex following both intrastriatal and intrathalamic injections.

EXAMPLE 2: EVALUATION OF THE TRANSDUCTION CAPABILITY OF TWO AAV VECTORS IN MOUSE CISTERNA MAGNA

The objective of this study was to compare brain distribution of GFP following injection of a modified recombinant AAV2-GFP (also referred to as Mannose-AAV2-GFP) vs. unmodified AAV2-GFP via the cisterna magna route in mice. The extent of labelling, as a proxy of the area of transduction, was performed by GFP staining on one series of section of striatum, thalamus, substantia nigra (SN) for all groups of animals.

Materials

Animals

Eight (8) male C57 BL/6 mice (*Mus musculus*) were purchased from Janvier Labs.

Test Items

"Mannose-AAV2-GFP" is a recombinant AAV2 vector comprising a modified capsid with surface-bound mannose residues, and carrying an eGFP cDNA under control of a CAG promoter. Mannose residues were covalently bound to primary amines of lysine residues exposed at the surface of the AAV2 capsid, as described in Example 1.

"Vehicle" is buffered saline sterile solution (BSSS)+ 0.001% Pluronic® F68, as a negative control.

Methods

Test Items

Mannosylated rAAV2s were produced as previously described in International patent publication WO2017212019 and illustrated in FIG. 1. Briefly, unmodified rAAV2 were mixed in Tris buffer pH 9.3 with isothiocyanate-linker-mannose molecules, and incubated during 4 hours at 20° C. The mix was then dialyzed against buffered saline sterile solution (BSSS)+0.001% Pluronic® F68 to remove free molecules that did not bind to the AAV capsid.

Study Design

Eight (8) mice underwent stereotactic surgery and were injected unilaterally with the test items into the cisterna magna.

The animals were randomly assigned to 3 groups, names G1 to G3, according to Table 12.

TABLE 12

Treatment schedule.

| Group | n | Treatment | Target |
|---|---|---|---|
| G1 | 2 | Vehicle | Cisterna magna |
| G2 | 3 | Mannose-AAV2-GFP | Cisterna magna |
| G3 | 3 | AAV2-GFP | Cisterna magna |

Surgical Procedure

Buprenorphine (0.1 mg/kg; 10 mL/kg, s.c.) was given as an analgesic before and after surgery. The animal was placed in an anesthetic chamber supplied with a continuous flow of oxygen (1.5 L/min) and 3% isoflurane. Following loss of consciousness, the animal was placed in a stereotactic frame (Kopf) and its head was fixed into position using ear bars. The skin of the skull was incised.

Each mouse received a cisterna magna injection of 1.3 10E9 vg/brain (or vehicle).

Ex Vivo Analysis

Euthanasia and Tissue Processing

At the end of the in vivo phase (42 days following injection), animals were euthanized and tissue were collected, as described in Example 1.

GFP Immunohistochemistry

GFP immunohistochemistry was performed as described in Example 1.

Results

Figure 8A:
FIG. 8A: immunohistochemistry photograph (in color) of mouse striatum slices from the G1 [Vehicle] group.
Figure 8B:
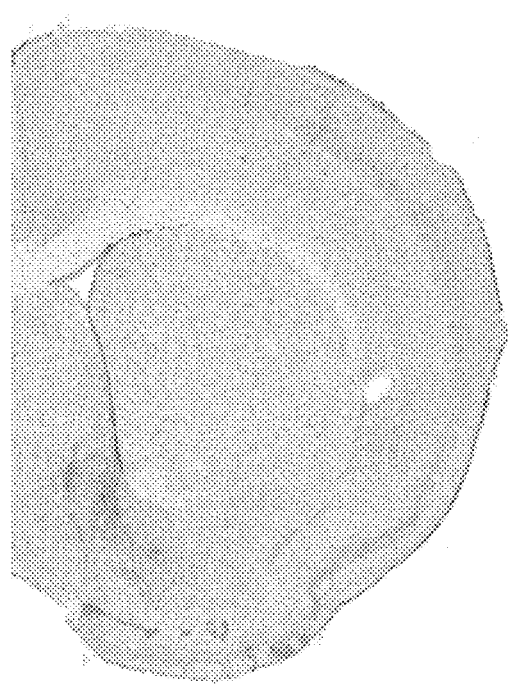
FIG. 8B: immunohistochemistry photograph (in color) of mouse striatum slices from the G2 [mannose AAV2] group.
Figure 8C:
FIG. 8C: immunohistochemistry photograph (in color) of mouse striatum slices from the G3 [AAV2-GFP] group.

GFP staining in the striatum Representative immunohistochemically stained striatum slices of mouse from the G1, G2 and G3 group are shown in FIG. 8A, FIG. 8B and FIG. 8C respectively.

GFP Staining in the Thalamus

Representative immunohistochemically stained thalamus slices of mouse from the G1, G2 and G3 group are shown in FIG. 9A, FIG. 9B and FIG. 9C respectively.

GFP Staining in the Substantia Nigra

Figure 10A:
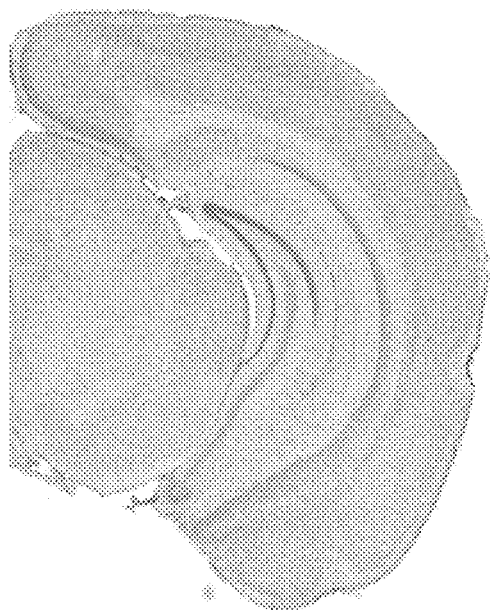
FIG. 10A: immunohistochemistry photograph (in color) of mouse substantia nigra slices from the G1 [Vehicle] group.
Figure 10B:
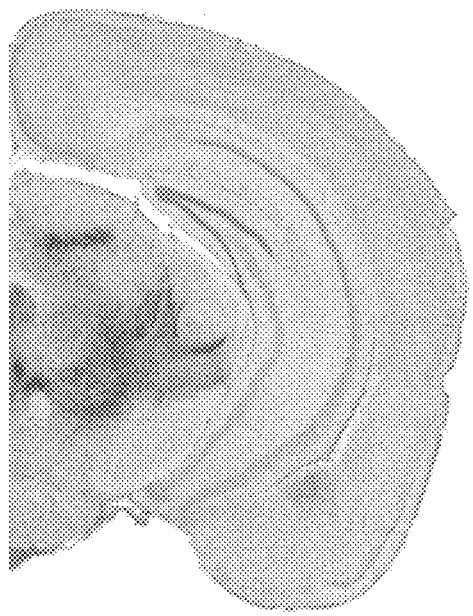
FIG. 10B: immunohistochemistry photograph (in color) of mouse substantia nigra slices from the G2 [mannoseAAV2-GFP] group.
Figure 10C:
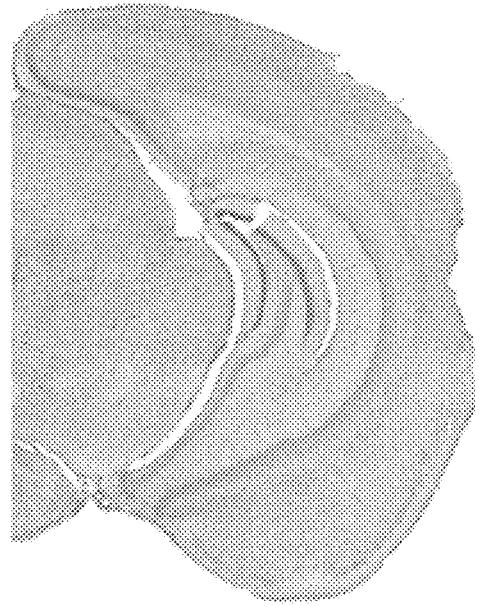
FIG. 10C: immunohistochemistry photograph (in color) of mouse substantia nigra slices from the G3 [AAV2-GFP] group.
Figure 11A:
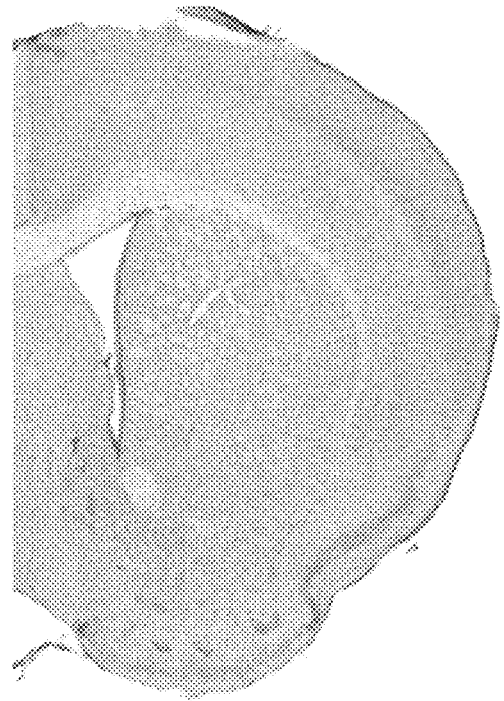
FIG. 11A: immunohistochemistry photograph (in color) of mouse striatum slices from the G1 [Vehicle] group.
Figure 11B:
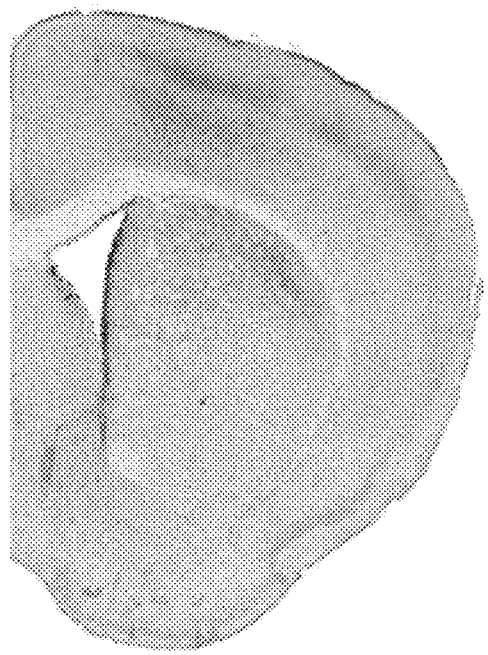
FIG. 11B: immunohistochemistry photograph (in color) of mouse striatum slices from the G2 [AAV2-GFP] group.
Figure 12A:
FIG. 12A: immunohistochemistry photograph (in color) of mouse thalamus slices from the G1 [Vehicle] group.
Figure 12B:
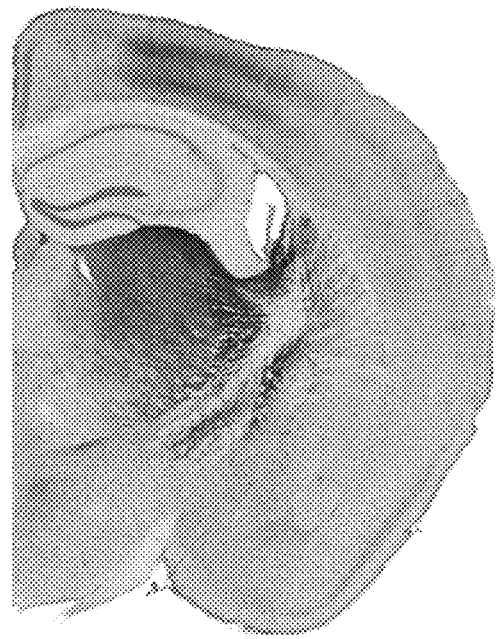
FIG. 12B: immunohistochemistry photograph (in color) of mouse thalamus slices from the G2 [AAV2-GFP] group.
Figure 12C:
FIG. 12C: immunohistochemistry photograph (in color) of mouse thalamus slices from the G3 [mannose AAV2-GFP] group.
Figure 12D:
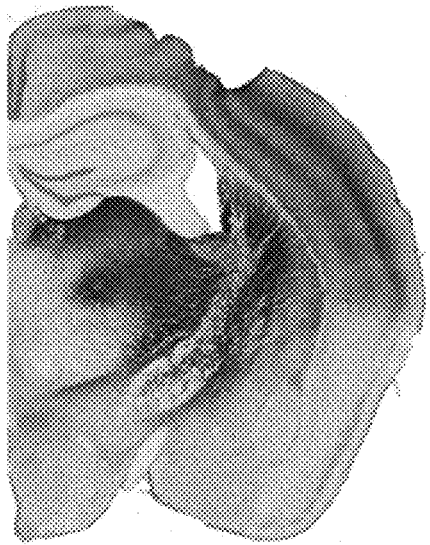
FIG. 12D: immunohistochemistry photograph (in color) of mouse thalamus slices from the G4 [galactose AAV2-GFP] group.
Figure 12E:
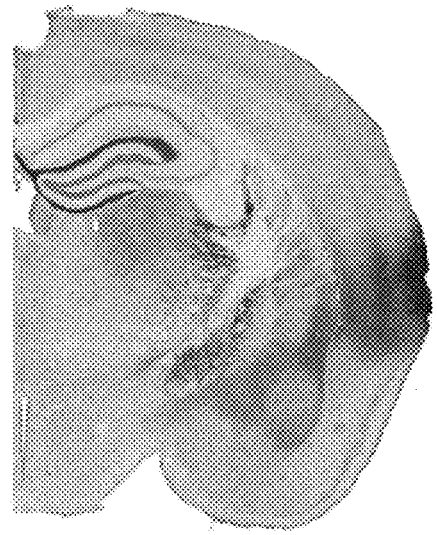
FIG. 12E: immunohistochemistry photograph (in color) of mouse thalamus slices from the G5 [NacetylGlucosamine AAV2] group.
Figure 13A:
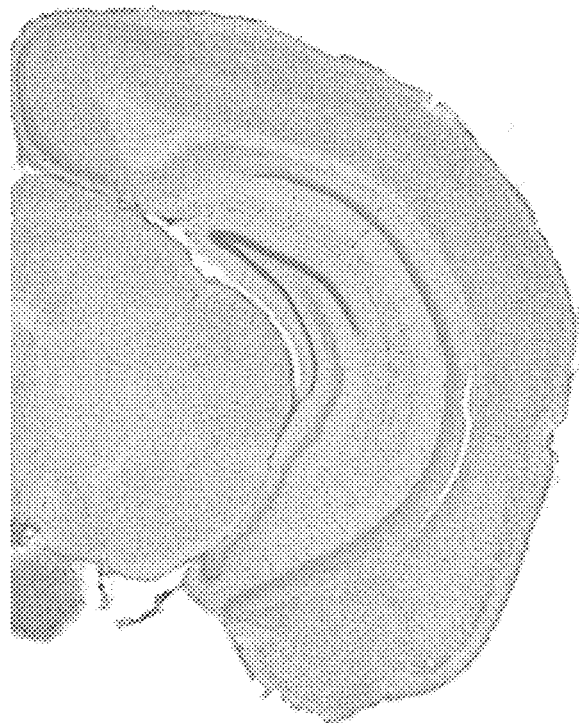
FIG. 13A: immunohistochemistry photograph (in color) of mouse substantia nigra slices from the G1 [Vehicle] group.
Figure 13B:
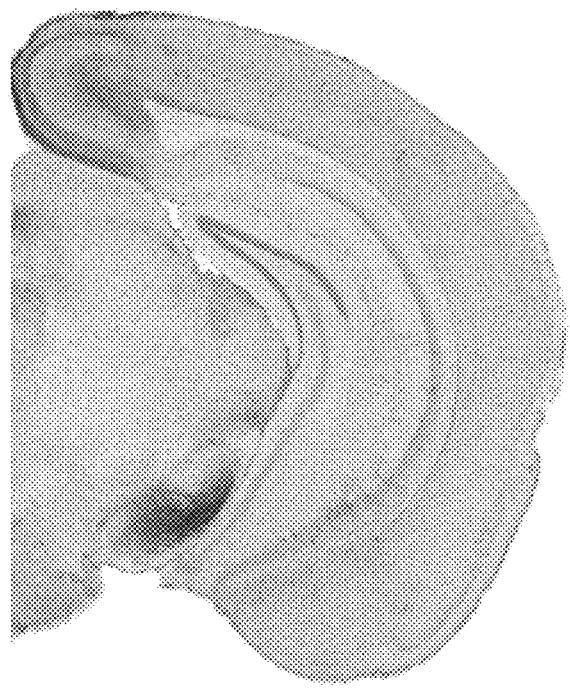
FIG. 13B: immunohistochemistry photograph (in color) of mouse substantia nigra slices from the G2 [AAV2-GFP] group.
Figure 13C:
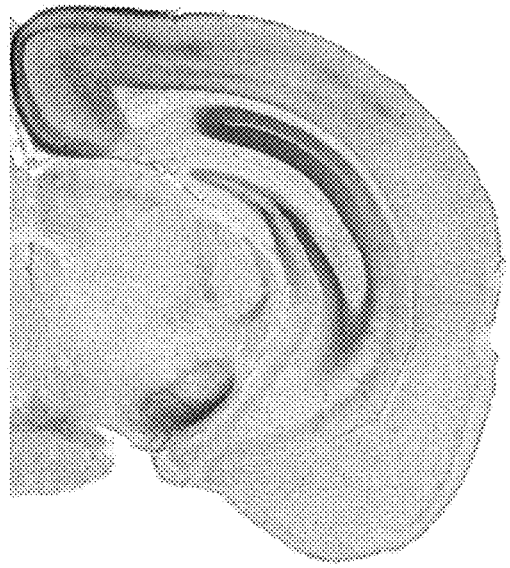
FIG. 13C: immunohistochemistry photograph (in color) of mouse substantia nigra slices from the G3 [mannose AAV2-GFP] group.
Figure 13D:
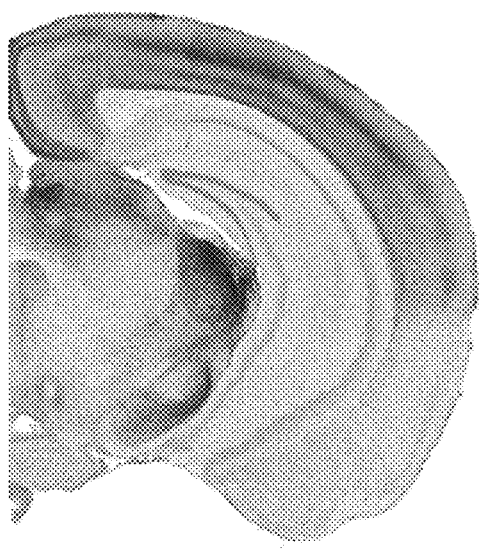
FIG. 13D: immunohistochemistry photograph (in color) of mouse substantia nigra slices from the G4 [galactose AAV2-GFP] group.
Figure 13E:
FIG. 13E: immunohistochemistry photograph (in color) of mouse substantia nigra slices from the G5 [NacetylGlucosamine AAV2] group.

Representative immunohistochemically stained substantia nigra slices of mouse from the G1, G2 and G3 group are shown in FIG. 10A, FIG. 10B and FIG. 10C respectively.

Conclusion

The objective of the study was to investigate the potential of two AAV vectors ("unmodified AAV2-GFP" and "Mannose-AAV2-GFP") to transduce large brain areas in mouse.

Neither the striatum nor the hippocampus appears to be transduced after cisterna magna injection of both AAV2 vectors.

In contrast, each AAV vectors drove the expression of GFP in the thalamus and the substantia nigra but to a different extent.

However, the mannosylated rAAV2 appears to induce a stronger GPF expression than the unmodified rAAV2 in the thalamus and the substantia nigra. Moreover, the mannosylated rAAV2 achieved a greater bilateral coverage of expression of thalamic nuclei and the substantia nigra than the unmodified AVV2, when administered through the cisterna magna. Thus, a single administration of the mannosylated rAAV2 in the cisterna magna led to a bilateral thalamus and substantia nigra transduction.

EXAMPLE 3: EVALUATION OF THE TRANSDUCTION CAPABILITY OF THREE MODIFIED AAV VECTORS IN MOUSE RIGHT STRIATUM

The objective of this study was to compare brain distribution of GFP following injection of 3 modified rAAV2-GFP (Mannose-AAV2-GFP, Galactose-AAV2-GFP, a N-AcetylGlucosamine-AAV2-GFP) vs. unmodified AAV2-GFP via the intrastriatal route in mice. The extent of labelling, as a proxy of the area of transduction, was performed by GFP staining on one series of section of striatum, thalamus, substantia nigra (SN) for all groups of animals.

Materials

Animals

Fourteen (14) male C57 BL/6 mice (*Mus musculus*) were purchased from Janvier Labs.

Test Items

"Modified rAAV2-GFP" is a recombinant AAV2 vector comprising a modified capsid with surface-bound saccharide residues (either mannose, galactose or N-acetyl-glucosamine), and carrying an eGFP cDNA under control of a CAG promoter. Mannose, galactose and N-acetyl-glucosamine residues were covalently bound to primary amines of lysine residues exposed at the surface of the AAV2 capsid, as described in Example 1.

"Vehicle" is DPBS Ca2+, Mg2+, 0.001% Pluronic® F68, as a negative control.

Methods

Test Items

Modified rAAV2s were produced as previously described in International patent publication WO2017212019 and illustrated in FIG. 1. Briefly, unmodified rAAV2 were mixed in Tris buffer pH 9.3 with isothiocyanate-linker-saccharide molecules, and incubated during 4 hours at 20° C. The mix was then buffer-exchanged against DPBS, Ca2+, Mg2+ supplemented with 0.001% Pluronic® F68 to remove free molecules that did not bind to the AAV capsid.

Study Design

Fourteen (14) mice underwent stereotactic surgery and were injected unilaterally with the test items into the right striatum.

The animals were randomly assigned to 5 groups, names G1 to G5, according to Table 13.

TABLE 13

Treatment schedule.

| Group | n | Treatment | Target |
|---|---|---|---|
| G1 | 2 | Vehicle | Right striatum |
| G2 | 3 | AAV2-GFP | Right striatum |
| G3 | 3 | Mannose-AAV2-GFP | Right striatum |
| G4 | 3 | Galactose-AAV2-GFP | Right striatum |
| G5 | 3 | N-acetyl-glucosamine-AAV2-GFP | Right striatum |

Surgical Procedure

Buprenorphine (0.1 mg/kg; 10 mL/kg, s.c.) was given as an analgesic before and after surgery. The animal was placed in an anesthetic chamber supplied with a continuous flow of oxygen (1.5 L/min) and 3% isoflurane. Following loss of consciousness, the animal was placed in a stereotactic frame (Kopf) and its head was fixed into position using ear bars. The skin of the skull was incised.

Each mouse received two unilateral injections into the right striatum of one of test items (or vehicle), corresponding to a total dose of 5.5 10E8 vg/brain of the test item. This was performed using a glass pipette coupled to a picosprizer, at the coordinates of Table 14.

TABLE 14

Injection coordinates.

| Target | AP (mm) | ML (mm) | DV (mm) | Volume/target (µL) |
|---|---|---|---|---|
| Right striatum | +1.0 | 2.1 | −2.6 | 0.5 |
|  | +0.3 | 2.3 | −2.6 | 0.5 |

AP: anterior-posterior;
ML: medial-lateral;
DV: dorsal-ventral.

Ex Vivo Analysis
Euthanasia and Tissue Processing

At the end of the in vivo phase (6 weeks following injection), animals were euthanized and tissue were collected, as described in Example 1.

GFP Immunohistochemistry

GFP immunohistochemistry was performed as described in Example 1.

Results

GFP Staining in the Right Striatum

Representative immunohistochemically stained striatum slices of mouse from the G1, G2, G3, G4 and G5 group are shown in FIG. 11A, FIG. 11B, FIG. 11C, FIG. 11D and FIG. 11E respectively.

GFP Staining in the Thalamus

Representative immunohistochemically stained thalamus slices of mouse from the G1, G2, G3, G4 and G5 group are shown in FIG. 12A, FIG. 12B, FIG. 12C, FIG. 12D and FIG. 12E respectively.

GFP Staining in the Substantia Nigra

Immunohistochemically stained substantia nigra slices of mouse from the G1, G2, G3, G4 and G5 group are shown in FIG. 13A, FIG. 13B, FIG. 13C, FIG. 13D and FIG. 13E respectively.

Conclusion

The objective of the study was to investigate the potential of three modified AAV vectors compared to an unmodified AAV2 vector to transduce large brain areas in mouse:
unmodified AAV2-GFP
Mannose-AAV2-GFP
Galactose-AAV2-GFP
N-acetyl-glucosamine-AAV2-GFP Every AAV vectors drove the expression of GFP.

Animals that were injected into the striatum were stained for back to back comparison. The parent AAV2-GFP leads to ipsilateral GFP staining in the striatum, thalamus, and substantia nigra.

The other three modified vectors presented a similar pattern of immunostaining in the striatum, thalamus, and substantia nigra.

Parietal cortices and hippocampus area appeared to be widely transduced with the three modified rAAV2s.

Although some cortical areas, mostly parietal, might present differences between vectors, both Mannose-AAV2-GFP and N-acetylglucosamine-AAV2-GFP injected animals presented a strong immunostaining in the ispislateral and contralateral hippocampus. N-acetylglucosamine-AAV2-GFP injection induced a stronger GFP staining in the dentate gyrus compared to Mannose-AAV2-GFP injection.

EXAMPLE 4: EVALUATION OF THE TRANSFECTION CAPABILITY OF SEVERAL AAV VECTORS IN MACAQUE MONKEY STRIATUM

The objective of this proposal was to investigate the potential of three viral vectors, an unmodified AAV2-GFP, an unmodified AAV5-GFP and a modified recombinant AAV2-GFP (also referred to as Mannose-AAV2-GFP), to transfect large brain areas in the macaque monkey.

Materials
Animals

Seven (7) male Cynomolgus monkeys (*Macaca fascicularis*) were purchased from BioPrim, France.

Test Items

"modified rAAV2-GFP" is a recombinant AAV2 vector comprising a modified capsid with surface-bound mannose residues wherein said residues were covalently bound to primary amines of lysine residues exposed at the surface of the AAV2 capsid, and carrying an eGFP cDNA under control of a CAG promoter.

"Vehicle" is buffered saline sterile solution (BSSS)+ 0.001% Pluronic® F68, as a negative control.

Methods
Test Items

Mannosylated rAAV2s were produced as previously described in International patent publication WO2017212019 and illustrated in FIG. 1. Briefly, unmodified rAAV2 were mixed in Tris buffer pH 9.3 with isothiocyanate-linker-mannose molecules, and incubated during 4 hours at 20° C. The mix was then dialyzed against buffered saline sterile solution (BSSS)+0.001% Pluronic® F68 to remove free molecules that did not bind to the AAV capsid.

Study Design

Seven (7) macaques underwent stereotactic surgery and receives unilateral injections into the right striatum by stereotactic surgery.

The animals are randomly assigned to 4 groups, names 1 to 4, according to Table 15.

TABLE 15

Treatment schedule.

| Group | n | Treatment | Target |
|---|---|---|---|
| 1 | 1 | Vehicle | Striatum |
| 2 | 2 | AAV2-GFP | Striatum |
| 3 | 2 | AAV5-GFP | Striatum |
| 4 | 2 | Mannose-AAV2-GFP | Striatum |

Preoperative Procedure

Anesthesia and Antibiotic and Analgesic Therapy

On the day prior to surgery animals were given Duphamox at 15 mg/kg subcutaneously (s.c.) for infection prophylaxis.

On the day of surgery, each animal was given atropine SO4 at 0.04 mg/kg, intra-muscularly (i.m.) prior to preparation for surgery. The non-steroidal anti-inflammatory drug Ketophen was then given at 2 mg/kg subcutaneously (s.c.). At least 10 minutes later, each animal was initially anaesthetized with Ketamine HCl at 10 mg/kg, i.m.

Xylocaine cream was then be applied topically as an anesthetic lubricant. The animal was then intubated and maintained in anesthesia with isoflurane inhalant anesthetic delivered through a volume-regulated respirator. The heart rate and oxygen saturation were monitored and recorded at intervals of at least 30 minutes throughout surgery. A temperature probe was placed rectally to allow for monitoring of core body temperature at intervals of at least 30 minutes throughout surgery. Animals were placed on a heating pad with a second pad placed on top of the animals if required as indicated by a drop in the animal's core body temperature.

Surgical Preparation

An ophthalmic ointment was administered to each eye (Liposic ophthalmic gel). The hair was clipped from the cranium and cranio-dorsal portion of the neck and sides.

Each animal was positioned for surgery in a stereotactic apparatus.

The surgical site was prepared for aseptic surgery by initially wiping the area with sponges soaked in 70% isopropyl alcohol scrub, which was allowed to dry, followed by application of DuraPrep™ (or similar solution), which will also be allowed to dry. The animals were appropriately draped for strict aseptic surgery.

Surgical Procedures

Location of Injections Sites

As individual macaques differ greatly with regard to specific intracerebral sites, the standard Horsley-Clarke stereotactic technique has been improved by using sagittal and frontal ventriculography to locate with accuracy the borders of the third ventricles and the edges of the anterior and posterior commissures.

After making a small craniotomy, without damaging the dura matter, a ventriculographic cannula mounted on a glass syringe was introduced into the anterior horn of the lateral ventricle and a contrast medium (Omnipaque, Nycomed, Norway) injected.

A stereotactic atlas was used for precise adjustment before insertion into the skull. The precise position of the anterior commissure was determined from ventriculography. The actual position of the left and right putamen was defined by combining the ventriculography-defined position of the anterior commissure and a stereotactic population-based historical atlas of the basal ganglia. Placement of the infusion cannula for delivery of the test item was then performed as described hereinbelow.

Test Item Administration

The area of the craniotomy was cleaned with sterile saline. Each animal then received unilateral injections of test items, corresponding to a total dose of 7.7 10E10 vg/brain of the test item.

The injections were made at two different depths, along three tracks within the putamen at Anterior Commissure (AC): AC+1, AC-2 and AC-5 mm.

The injections were made using a Hamilton 1701N syringe (100 µl, 30 Ga/51 mm/PST3) coupled to an automatic injector UMP-3 linked to Micro-4 controller (WPI), at a rate of 3 µl/min, with a total volume injected per animal of 90 µl.

The needle was left in place for 1 min after the deepest deposit of each track and 5 min after the second deposit of each track before being slowly withdrawn from the brain.

Once all injections had been completed the wound was closed in layers with a continuous pattern of absorbable suture material. The skin was closed with an appropriate size of absorbable suture material, placed in a subcuticular pattern. The animal was then allowed to recover from anesthesia.

Postoperative Monitoring

Checks on the condition of the animals were performed twice daily (a.m. and p.m.). Observers particularly focused on limb movements, offering pieces of fruits or sweets to the animals for enabling proper assessment of quality of limb movements.

The surgical incisions were observed for signs of infection, inflammation, and general integrity at least once daily (until incisions were healed).

Animals were assessed daily according to established humane end-point criteria. Appropriate veterinary support was given if necessary. Any animal showing signs of severe pain or distress, which is likely to endure, was to be promptly euthanized.

Ex Vivo Analysis

Euthanasia and Tissue Processing

On day 56 following injections, the animals were humanely euthanised by barbiturate overdose in accordance with European Veterinary Medical Association guidelines and then perfused with saline containing heparin followed by a 4% paraformaldehyde solution.

A comprehensive necropsy was performed and the following organs were removed: brain, heart, kidneys, liver, lungs, mesenteric lymph nodes, spleen, spinal cord (with a focus on dorsal root ganglion). A necropsy report for each individual was done.

The brain was fixed by immersion in paraformaldehyde (PFA: 4%). The tissue was then cryoprotected in 20% sucrose solution (in 0.1 M PBS) at 4° C. and then frozen. 50 µm sections (in coronal orientation for one hemisphere of the brain) was cut using a cryostat. Free-floating sections will be placed in cryoprotectant solution and stored at −20° C.

GFP Immunohistochemistry

GFP immunohistochemistry was performed as described in Example 1.

GFAP-NeuN—GFP Double Fluorescence Staining

The cell tropism in the striatum, substantia nigra and globus pallidus were defined using double immunostaining for GFP and neuronal (NeuN), astroglial (GFAP/S100), oligodendroglial (Olig2) or microglial (Iba1) markers.

GFP and NeuN/GFAP/Olig2/Iba1 immunohistochemistry were performed together in one section per structure of interest per animal.

After thorough rinsing with PBS, non-specific labelling was prevented by blocking antigenic sites in PBS containing 2% BSA, 0.3% triton X-100 and 0.01% thimerosal, for 30 minutes.

Sections were then incubated overnight at room temperature in primary antibodies mix (anti-Iba1 Abcam ab5076 1/1000; anti-GFAP-S10 Dako Z0334-Z0311, 1/1000 and 1/2000; anti-Olig2 EPR2676 Abcam, 1/100; anti-NeuN MAB377 Merck, 1/500) in PBS containing 0.2% BSA, 0.3% triton X-100 and 0.01% thimerosal.

On the next day, sections were rinsed with PBS and incubated for 30 minutes incubation with antibody, conjugated with a Dylight®488 fluorophore diluted at 1:500 in PBS.

After thorough rinsing with PBS between each step, one antibody was revealed with polymer-HRP anti-rabbit (Dako EnVision+™ Kit, K4011) for 30 minutes followed by a 30 minutes incubation with an anti-HRP antibody conjugated with a Dylight®549 fluorophore diluted at 1:1000 in PBS.

After thorough rinsing with PBS, nuclear Hoechst staining was performed on sections (Hoechst solution diluted at 1:5000) for 30s and stopped with several PBS washes.

Sections were then mounted onto gelatin-coated slides, cover-slipped in aqueous Fluoromount™ mounting media and stored at 4° C. until analysis.

Fluorescence images were acquired for both staining with the same exposure parameters among all sections on an Olympus epifluorescence microscope (Olympus BX63) coupled with a CCD camera (Hamamatsu ORCA Flash 4.0LT). Three fields of view were acquired at ×40 magnification for each area and section. 16 bites image files were saved and treated in ImageJ software.

Histopathology

In addition to the macroscopic analysis of brain, heart, kidneys, liver, lungs, mesenteric lymph nodes, spleen, spinal cord (with a focus on dorsal root ganglion), these tissues were subject to hispathological analysis. The organs/tissues were sampled and put in cassettes for paraffin-embedding. Three blocks per organ were prepared and at least 4 sections per block were examined.

Results

GFP Staining in the Striatum

Figures 14A, 14B, 14C:
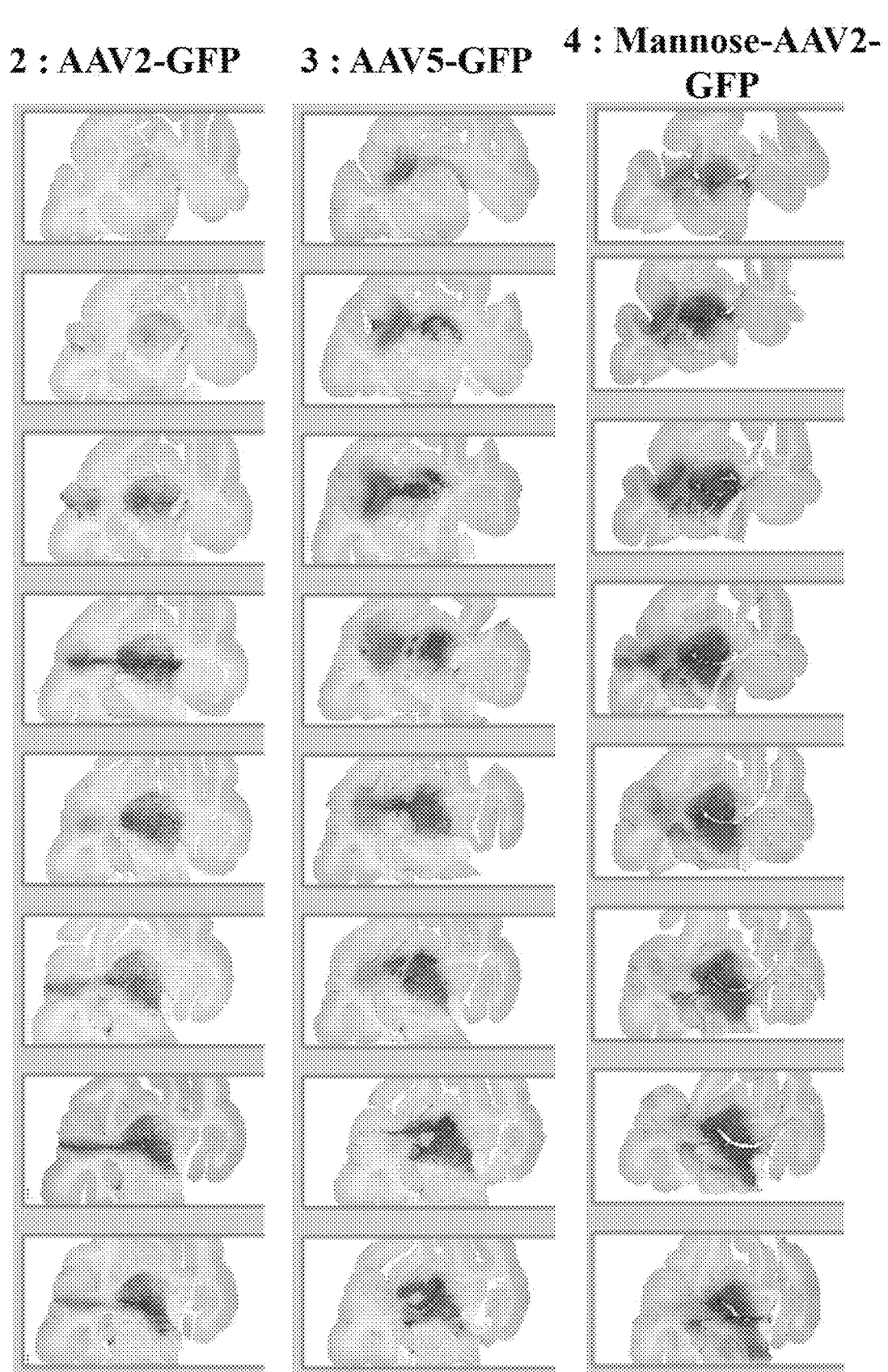
FIG. 14A: immunohistochemistry photograph (in color) of macaque striatum slices from the G2 [AAV2-GFP] group.
FIG. 14B: immunohistochemistry photograph (in color) of macaque striatum slices from the G3 [AAV5-GFP] group.
FIG. 14C: immunohistochemistry photograph (in color) of macaque striatum slices from the G4 [mannose AAV2-GFP] group.

Representative immunohistochemically stained striatum slices of macaques from the G2, G3 and G4 groups are shown in FIG. 14A, FIG. 14B and FIG. 14C respectively.

GFP Staining in the Substantia Nigra

Figure 15A:
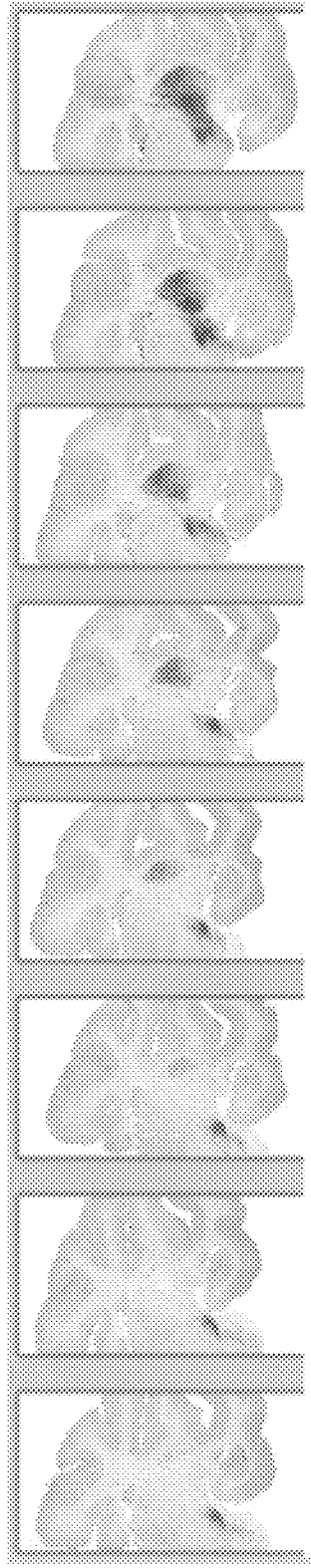
FIG. 15A: immunohistochemistry photograph (in color) of macaque substantia nigra slices from the G2 [AAV2-GFP] group.
Figure 15B:
FIG. 15B: immunohistochemistry photograph (in color) of macaque substantia nigra slices from the G3 [AAV5-GFP] group.
Figure 15C:
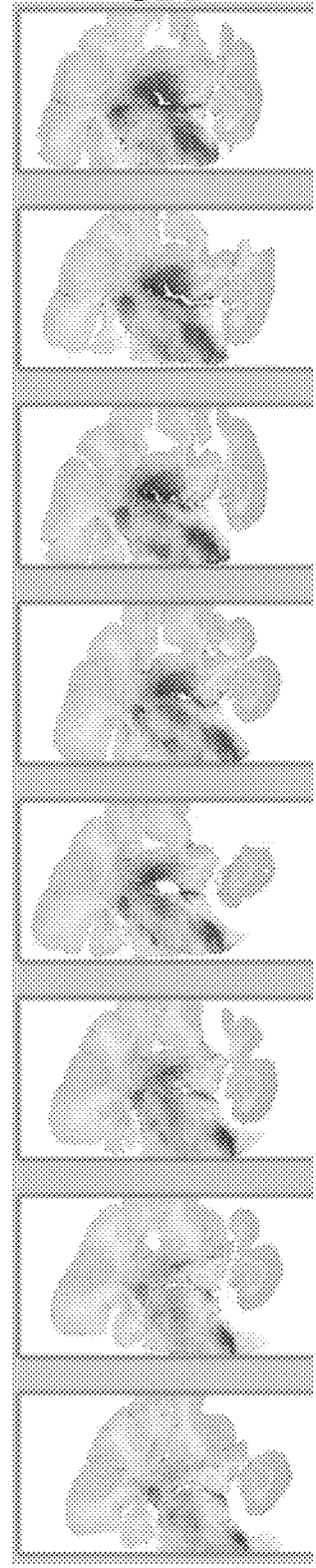
FIG. 15C: immunohistochemistry photograph (in color) of macaque substantia nigra slices from the G4 [mannose AAV2-GFP] group.

Representative immunohistochemically stained substantia nigra slices of macaques from the G2, G3 and G4 groups are shown in FIG. 15A, FIG. 15B and FIG. 15C respectively.

Figure 16A:
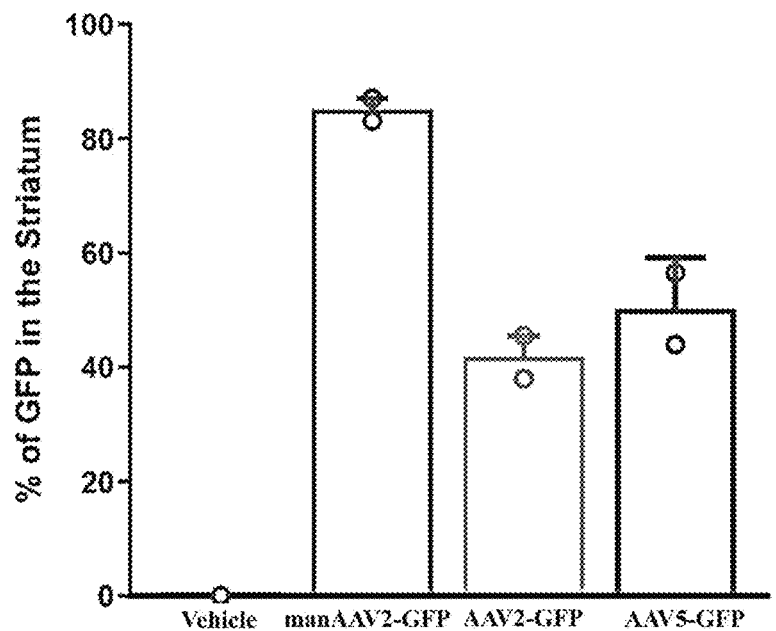
FIG. 16A: Percentage of GFP transduction in the striatum. Bars represent the group mean; dots represent the individual animal values.
Figure 16B:
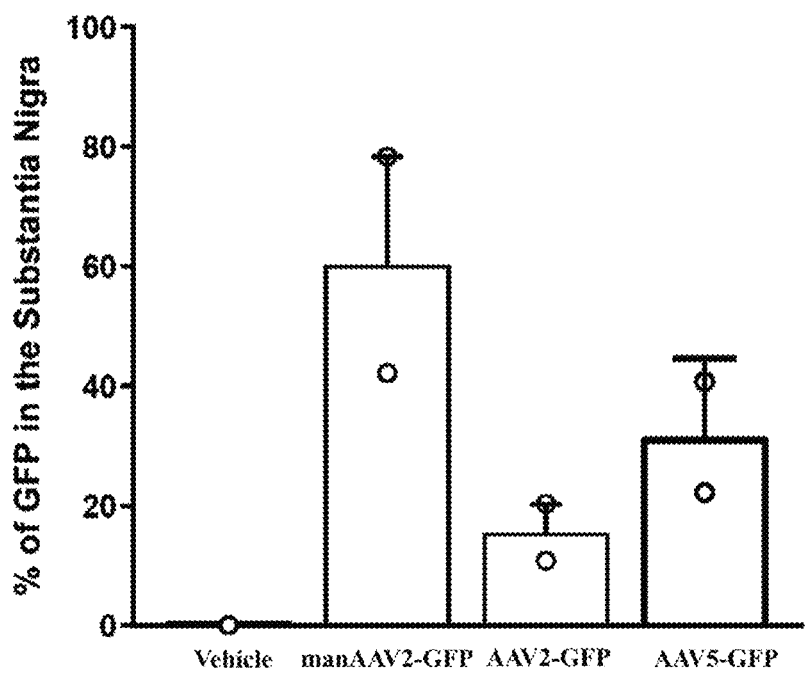
FIG. 16B: Percentage of GFP transduction in the substantia nigra. Bars represent the group mean; dots represent the individual animal values.
Figure 17A:
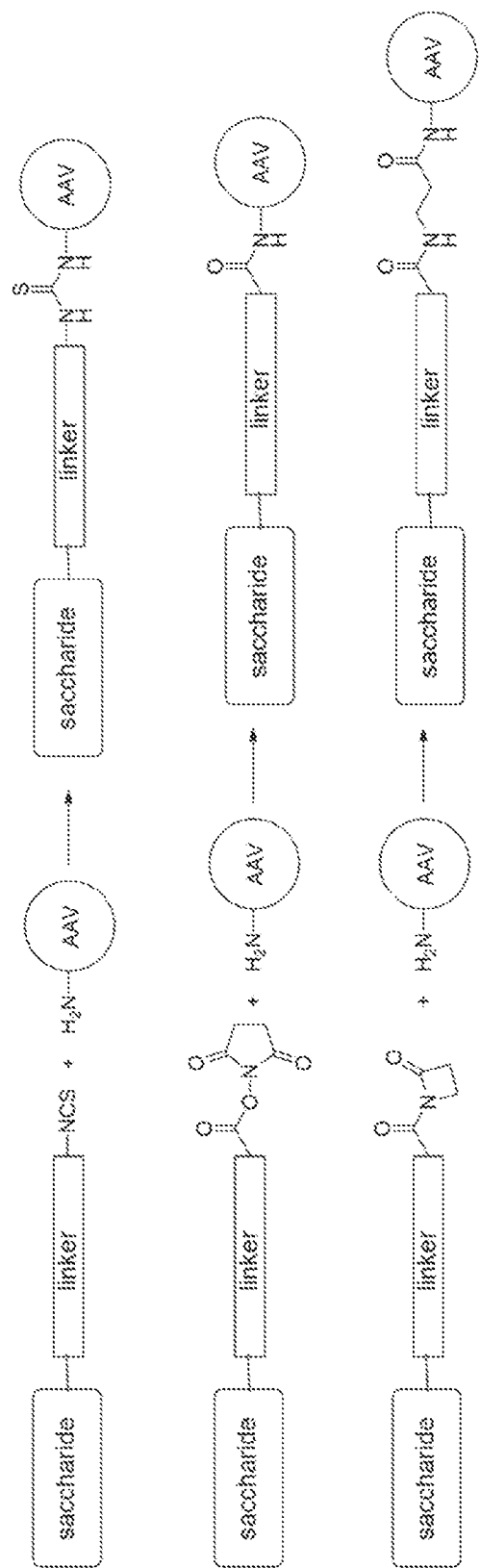
FIG. 17A: Schematic representation of the illustrating coupling reactions between a saccharide moiety and a AAV surface-exposed primary amine (FIG. 17A: general case; 17B: illustrating example with a mannose moiety).
Figure 17B:
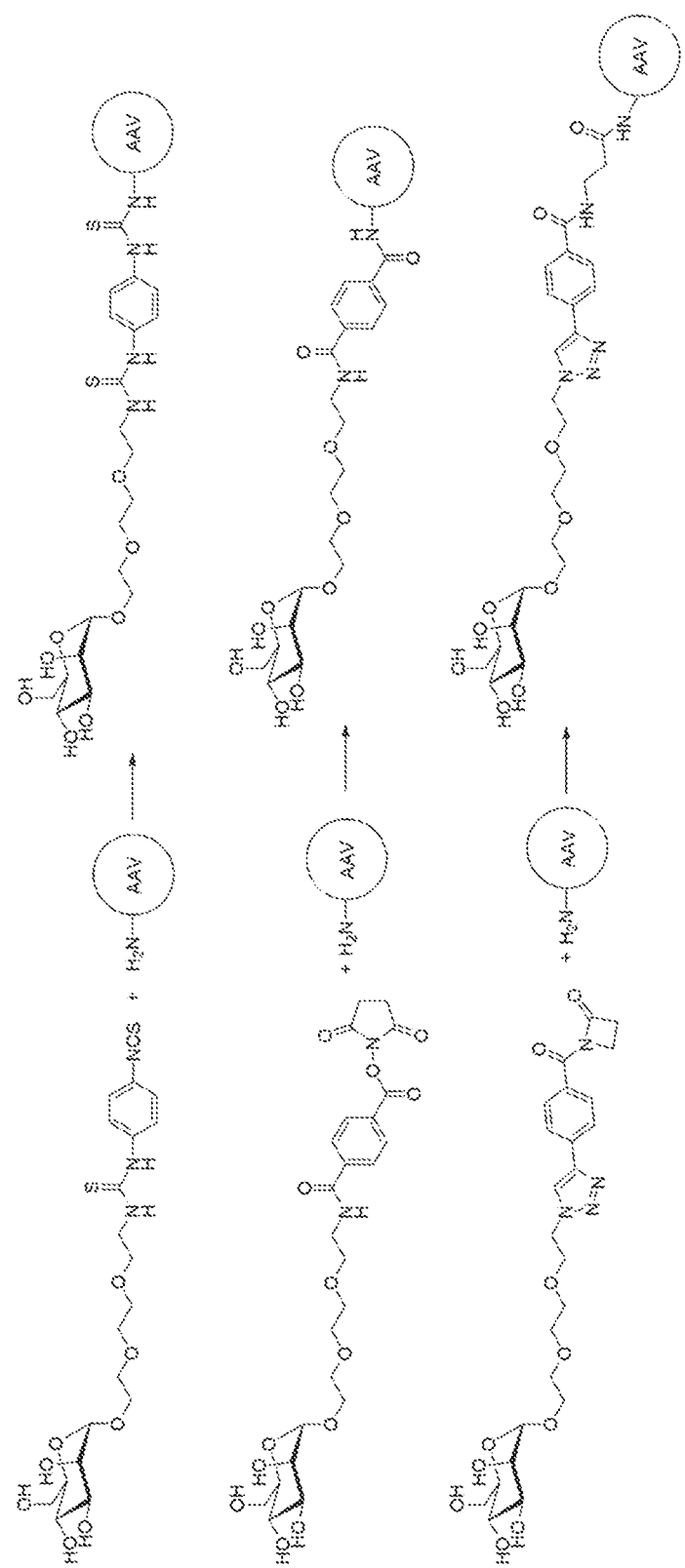

The percentages of GFP transduction in the striatum and in the substantia nigra, 56 days after intrastriatal injection, are respectively shown on FIG. 16A and FIG. 16B.

Cellular Tropism

External Globus Pallidus (GPe) and internal Globus Pallidus (GPi) slices of macaques from the G, G2, G3 and G4 groups are immunofluorescently co-stained for:

Iba1 and GFP
GFAP/S100 and GFP
Olig2 and GFP
NeuN and GFP.

Iba1 antibody allows staining of microglia, NeuN antibody allows staining of neuronal cells, GFAP/S100 antibody allows staining of astroglial cells and Olig2 antibody allows staining of oligodendroglial cells.

Conclusion

Seven macaque monkeys were used in this study and assigned to 4 groups. Vectors or vehicle were administered within the putamen part of the striatum. The vector Mannose-AAV2-GFP transduced over 80% of the striatum and over 60% of the substantia nigra, while unmodified AAV2-GFP and AAV5-GFP both only achieved under 50% of the striatum and 40% of the substantia nigra.

Histopathology did not show any sign of toxicity in major organs, including dorsal root ganglions (DRG).

Double fluorescence staining was performed for GFP on one hand (index of transduction) and for a phenotypic cellular marker (NeuN for neuron, GFAP-S100 for astrocytes, Olig2 for oligodendrocytes and Iba1 for microglial cells).

In the striatum, all three vectors were expressed in medium spiny neurons, while no obvious GFP expression was detected in astrocytes, oligodendrocytes or microglial cells (data not shown).

In the substantia nigra, all three vectors were expressed in terminals, with a distinctive fibrillar pattern, and none showed a cell body expression of GFP (data not shown), i.e. no obvious GFP expression was detected in neurons, astrocytes, oligodendrocytes or microglial cells of the substantia nigra. Those fibres present into the substantia nigra are most likely the GABAergic projections of the medium spiny neurons that project from the striatum to the substantia nigra (neuronal cytoplasmic staining in the striatum, fibres in the substantia nigra).

The pallidal complex may be divided into GPe and GPi. While the GPe appears to be crossed by a huge GFP-positive fibres network with no cellular co-staining (whatever the cell type), the GPi, besides a beautiful fibre network consistent with the striatofugal neurons might present some neuronal transduction by the three vectors.

Altogether these results show that Mannose-AAV2-GFP transduced striatal medium spiny neurons with a great efficiency, largely superior to the two other vectors. The cellular tropism in the analyzed brain regions was comparable between the 3 vectors.

The observed transduction patterns suggest that Mannose-AAV2-GFP holds a therapeutic profile of great interest for gene therapy targeting the striatum and the substantia nigra.

Until today, all gene therapy approaches for neurological disorders tested in human have not reached a clinical significance, mainly because of a lack of solid expression at the target site and/or at the afference level.

The inventors have surprisingly shown that their modified AAV vectors are capable of effectively transducing certain areas of the brain, including the striatum, the thalamus, the substantia nigra, the parietal cortices, the hippocampus and the globus pallidus. Thus, these modified AAV vectors are of great interest for targeting these areas, and/or for treating diseases affecting these areas.

The invention claimed is:

1. A method for transducing one or more cells within a plurality of brain tissues of a primate subject, comprising:
    administering a modified adeno-associated virus (AAV) vector, wherein
        the modified AAV vector comprises at least one surface-bound saccharide, and
        the modified AAV vector is administered directly to an intraparenchymal site; and
    wherein the plurality of brain tissues comprises at least one brain tissue that is distant from the site of administration.

2. The method according to claim 1, wherein the modified AAV vector comprises at least one transgene.

3. The method according to claim 1, wherein administering is to a subject suffering from a CNS disease.

4. The method according to claim 3, wherein the CNS disease is selected from a CNS infectious disease, a CNS degenerative disease, a CNS auto-immune disease, a CNS tumor disease, a cerebrovascular disease, a CNS injury, a CNS structural defect, and combinations thereof.

5. The method according to claim 3, wherein the CNS disease is selected from the group comprising Huntington's disease, Parkinson's disease, multiple sclerosisatrophy, Lewis body dementia (LBD), progressive supranuclear palsy, frontotemporal dementia and Angelman syndrome.

6. The method according to claim 1, wherein the modified AAV vector is administered directly to a single intraparenchymal site.

7. The method according to claim 6, wherein the modified AAV vector is administered directly to a single intrathalamic or intrastriatal site.

8. The method according to claim 7, wherein the step of administering comprises administering by a single injection.

9. The method according to claim 6, wherein the intraparenchymal site is the striatum.

10. The method according to claim 7, wherein the intraparenchymal site is the thalamus.

11. The method according to claim 1, wherein the modified AAV vector is selected from AAV1, AAV2, AAV3, AAV4, AAV5, AAV6, AAV7, AAV8, AAV9, AAV10, AAV11 and AAV12; or pseudotypes, and chimeras thereof.

12. The method according to claim 11, wherein the modified AAV vector is an AAV2 vector.

13. The method according to claim 1, wherein the surface-bound saccharide is selected from the group consisting of monosaccharides, oligosaccharides, polysaccharides and combinations thereof.

14. The method according to claim 1, wherein the surface-bound saccharide is a hexose.

15. The method according to claim 14, wherein the hexose is selected from the group consisting of mannoses, galactoses, N-acetylglucosamines, and combinations thereof.

16. The method according to claim 1, wherein the surface-bound saccharide is covalently bound to a capsid protein of the AAV vector.

17. The method according to claim 16, wherein the surface-bound saccharide is covalently bound to a surface-exposed amino acid residue of the capsid protein.

18. The method according to claim 1, wherein the saccharide is conjugated to the surface via a linker.

19. The method according to claim 16, wherein the surface-bound saccharide is covalently bound through a linker.

20. The method according to claim 1, wherein the step of administering comprises administering to a human subject.

21. The method according to claim 1, wherein the brain tissue that is distant from the site of administration and where one or more cells are transduced comprises the substantia nigra, the parietal cortices, the hippocampus, the globus pallidus, or combinations thereof.

22. The method according to claim 21, wherein the brain tissue that is distant from the site of administration and where one or more cells are transduced comprises the substantia nigra.

23. A method for transducing one or more cells within the substantia nigra, the parietal cortices, the hippocampus, or the globus pallidus, or combinations thereof, of a primate subject, comprising:
    administering a modified adeno-associated virus (AAV) vector, wherein
        the modified AAV vector comprises at least one surface-bound saccharide, and
        the modified AAV vector is administered directly to the striatum or the thalamus.

24. The method according to claim 23, wherein the modified AAV vector is administered to a single site within the striatum.

25. The method according to claim 24, wherein the step of administering comprises administering by a single injection.

26. A method for transducing one or more cells within at least one brain tissue distant from the site of administration of a primate subject, comprising:
    administering a modified adeno-associated virus (AAV) vector, wherein
        the modified AAV vector comprises at least one surface-bound saccharide, and
        the modified AAV vector is administered directly to an intraparenchymal site.

* * * * *